US006911321B2

(12) United States Patent
Presta et al.

(10) Patent No.: US 6,911,321 B2
(45) Date of Patent: Jun. 28, 2005

(54) NON-HUMAN PRIMATE FC RECEPTORS AND METHODS OF USE

(75) Inventors: Leonard G. Presta, San Francisco, CA (US); Angela K. Namenuk, Oakland, CA (US)

(73) Assignee: Genentech, Inc., South San Francisco, CA (US)

( * ) Notice: Subject to any disclaimer, the term of this patent is extended or adjusted under 35 U.S.C. 154(b) by 283 days.

(21) Appl. No.: 10/027,736

(22) Filed: Dec. 19, 2001

(65) Prior Publication Data

US 2003/0190614 A1 Oct. 9, 2003

(51) Int. Cl.[7] .......................... C12P 21/06; C12N 1/120; C12N 15/01; C07H 21/04
(52) U.S. Cl. ................... 435/69.1; 435/320.1; 435/455; 435/252.3; 536/23.5
(58) Field of Search ............................... 435/69.1, 455, 435/252.3, 320.1; 536/23.5

(56) References Cited

U.S. PATENT DOCUMENTS

| | | | |
|---|---|---|---|
| 4,518,584 A | 5/1985 | Mark et al. |
| 4,737,462 A | 4/1988 | Mark et al. |
| 5,189,014 A | 2/1993 | Cowan, Jr. |
| 5,824,487 A | 10/1998 | Ravetch et al. |
| 5,877,396 A | 3/1999 | Ravetch et al. |
| 6,194,551 B1 | 2/2001 | Idusogie et al. |
| 6,676,927 B1 | 1/2004 | Ravetch |

OTHER PUBLICATIONS

Simister, N. et al., "The structure and evolution of FcRn", *Non–Polymorphic Antigen Presentation Molecules*, pp. 333–337.
Norsworthy, P. et al., "Overrepresentation of the FCγ Receptor Type IIA R131/R131 Genotype in Caucasoid Systemic Lupus Erythematosus Patients with Autoantibodies to C1q and Glomerulonephritis", *Arthritis & Rheumatism*, vol. 42, No. 9, pp. 1828–1832 (Sep. 1999).
Namenuk A. et al., "Binding of Human IgG to Cynomolgus FcR,", *GenEmbl Database, National Center for Biotechnology Information, National Library of Medicine, NIH*, Accession No. AF485812 (Mar. 2002).
NCBI database, Accession No. L03418 (Porges et al., May 8, 1993).
Benincosa, L. et al., "Pharmacokinetics and Pharmacodynamics of a Humanized Monoclonal Antibody to Factor IX in Cynomolgus Monkeys", *The Journal of Pharmacology and Experimental Therapeutics*, vol. 292, No. 2, pp. 810–816 (Feb. 2000).
Brok, H. et al., "Prophylactic and therapeutic effects of a humanized monoclonal antibody against the IL–2 receptor (DACLIZUMAB) on collagen–induced arthritis (CIA) in rhesus monkeys", *Clinical and Experimental Immunology*, 124:134–141 (2001).

Clynes, R. et al., "Fc receptors are required in passive and active immunity to melanoma", *Proc. Natl. Acad. Sci. USA*, vol. 95, No. 2, pp. 652–656 (Jan. 20, 1998).
Fishwild, D. et al., "Differential Effects of Administration of a Human Anti–CD4 Monoclonal Antibody, HM6G, in Non-human Primates", *Clinical Immunology*, vol. 92, No. 2, pp. 138–152 (1999).
Ghetie, V. et al., "Multiple Roles for the Major Histocompatibility Complex Class I–Related Receptor FcRn", *Annual Review of Immunology*, 18:739–766 (2000).
Glennie, M. et al., "Clinical trials of antibody therapy", *Immunology Today*, vol. 21, No. 8, pp. 403–411 (Aug. 2000).
Gobburu, J. et al., "Pharmacokinetics/Dynamics of 5c8, a Monoclonal Antibody to CD154 (CD40 Ligand) Suppression of an Immune Response in Monkeys", *The Journal of Pharmacology and Experimental Therapeutics*, vol. 286, No. 2, pp. 925–930 (1998).
Hamawy, M. et al., "Immunotoxin FN18–CRM9 Induces Stronger T Cell Signaling Than Unconjugated Monoclonal Antibody FN18", *Transplantation*, vol. 72, No. 3, pp. 496–503 (Aug. 15, 2001
Hart, T. et al., "Preclinical efficacy and safety of mepolizumab (SB–240563), a humanized monoclonal antibody to IL–5, in cynomolgus monkeys", *The Journal of Allergy and Clinical Immunology*, vol. 108, No. 2, pp. 250–257 (Aug. 2001).
Kao, F. et al., "Genetics of Somatic Mammalian cells, VII. Induction and Isolation of Nutritional Mutants in Chinese Hamster Cells", *Proc. Natl. Acad. Sci. USA*, vol. 60, No. 4, pp. 1275–1281 (Aug. 1968).
Kim, J. et al., "Mapping the site on human IgG for binding of the MHC class I–related receptor, FcRn", *European Journal of Immunology*, 29:2819–2825 (1999).
Küester, H. et al., "Characterization and Expression of the Gene for the Human Fc Receptor γ Subunit", *The Journal of Biological Chemistry*, vol. 265, No. 11, pp. 6448–6452 (Apr. 15, 1990).
Kurucz, I. et al., "Bacterially expressed FcγRIIb is soluble and functionally actie after in vitro refolding", *Immunology Letters*, 75:33–40 (2000).
Lehrnbecher, T. et al., "Variant Genotypes of the Low–Affinity Fcγ Receptors in Two Control Populations and a Review of Low–Affinity Fcγ Receptor Polymorphisms in Control and Disease Populations", *Blood*, vol. 94, No. 12, pp. 4220–4232 (Dec. 15, 1999).

(Continued)

*Primary Examiner*—Christina Chan
*Assistant Examiner*—Michali A Belyavskyi
(74) *Attorney, Agent, or Firm*—Merchant & Gould, P.C.

(57) ABSTRACT

The invention provides isolated non-human primate Fc receptor polypeptides, the nucleic acid molecules encoding the Fc receptor polypeptides, and the processes for production of recombinant forms of the Fc receptor polypeptides, including fusions, variants, and derivatives thereof. The invention also provides methods for evaluating the safety, efficacy and biological properties of Fc region containing molecules using the non-human primate Fc receptor polypeptides.

14 Claims, 14 Drawing Sheets

OTHER PUBLICATIONS

Figure 1A:
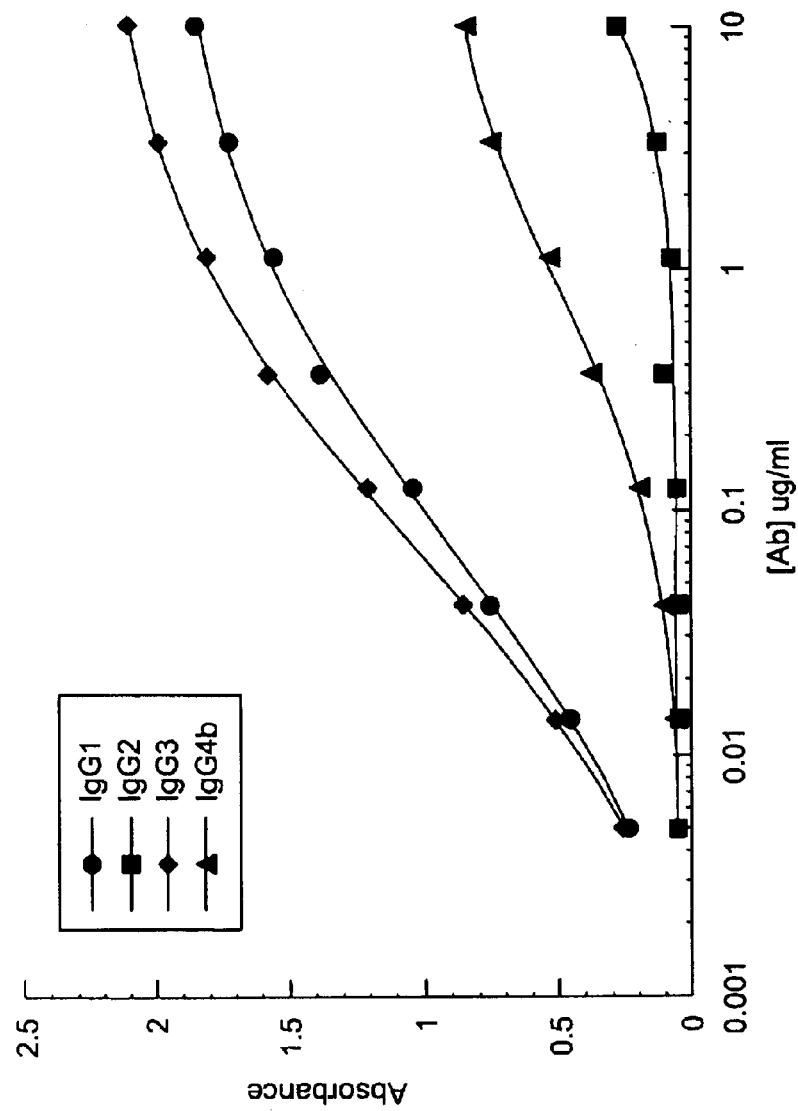

Lin, Y. et al., "Preclinical Pharmacokinetics, Interspecies Scaling, and Tissue Distribution of a Humanized Monoclonal Antibody against Vascular Endothelial Growth Factors", *The Journal of Pharmacology and Experimental Therapeutics*, vol. 288, No. 1, pp. 371–378 (1999).

Maxwell, K. et al., "Crystal structure of the human leukocyte Fc receptor, FcγRIIa", *Nature Structural Biology*, vol. 6, No. 5, pp. 437–442 (May 1999).

Mihara, M. et al., "Humanized Antibody to Human Interleukin–6 Receptor Inhibits the Development of Collagen Arthritis in Cynomolgus Monkeys", *Clinical Immunology*, vol. 98, No. 3, pp. 319–326 (Mar. 2001).

Mordenti, J. et al., "Comparisons of the Intraocular Tissue Distribution, Pharmacokinetics, and Safety of $^{125}$I–Labelled Full–Length and Fab Antibodies in Rhesus Monkeys Following Intravitreal Administration", *Toxicologic Pathology*, vol. 27, No. 5, pp. 536–544 (Sep.–Oct. 1999).

Mourad, G. et al., "Humanized IgG1 and IgG4 Anti–CD4 Monoclonal Antibodies", *Transplantation*, vol. 65, No. 5, pp. 632–641 (Mar. 15, 1998).

Ory, P. et al., "Characterization of Polymorphic Forms of Fc Receptor III on Human Neutrophils", *The Journal of Clinical Investigation*, vol. 83, No. 5, pp. 1676–1681 (May 1989).

Ory, P. et al., "Sequences of Complementary DNAs that Encode the NA1 and NA2 Forms of Fc Receptor III on Human Neutrophils", *The Journal of Clinical Investigation*, vol. 84, No. 5, pp. 1688–1691 (Nov. 1989).

Poston, R. et al., "Effects of Humanized Monoclonal Antibody to Rhesus CD11a in Rhesus Monkey Cardiac Allograft Recipients", *Transplantation*, vol. 69, No. 10, pp. 2005–2013 (May 27, 2000).

Radaev, S. et al., "The Structure of a Human Type III Fcγ Receptor in Complex with Fc", *The Journal of Biological Chemistry*, vol. 276, No. 19, pp. 16469–16477 (May 11, 2001).

Ravetch, J. et al., "IgG Fc Receptors", *Annual Review of Immunology*, vol. 19:275–290 (2001).

Reichert, J., "Monoclonal antibodies in the clinic", *Nature Biotechnology*, vol. 19, No. 9, pp. 819–822 (Sep. 2001).

Richter, W. et al., "Animal Pharmacokinetics of the Tumor Necrosis Factor Receptor–Immunoglobulin Fusion Protein Lenercept and Their Extrapolation to Humans", *Drug Metabolism and Disposition*, vol. 27, No. 1, pp. 21–25 (Jan. 1999).

Sampson, J. et al., "Unarmed, tumor–specific monoclonal antibody effectively treats brain tumors", *PNAS*, vol. 97, No. 13, pp. 7503–7508 (Jun. 20, 2000).

Sautès, C., "Structure and Expression of Fc Receptors (FcR)", *Cell–Mediated Effects of Immunoglobulins*, Chap. 2, pp. 29–66 (1997).

Schuurman, J. et al., "The inter–heavy chain disulfide bonds of IgG4 are in equilibrium with intra–chain disulfide bonds", *Molecular Immunology*, vol. 38, No. 1, pp. 1–8 (Jan. 2001).

Shinkura, H. et al., "Safety and kinetic properties of a humanized antibody to human interleukin–6 receptor in healthy non–human primates", *Toxicology*, 122:163–170 (Oct. 19, 1997).

Sondermann, P. et al., "Crystal structure of the soluble form of the human Fcγ–receptor IIb: a new member of the immunoglobulin superfamily at 1.7 Å resolution", *The EMBO Journal*, vol. 18, No. 5, pp. 1095–1103 (Mar. 1, 1999).

Sondermann, P. et al., "The 3.2-Å crystal structure of the human IgG1 Fc fragment–FcγRIII complex", *Nature*, 406:267–273 (Jul. 20, 2000).

Spiegelberg, H., "Biological Activities of Immunoglobulins of Different Classes and Subclasses", *Advances in Immunology*, 19:259–294 (1974).

van der Pol, W. et al., "IgG receptor IIa alleles determine susceptibility and severity of Guillain–Barré syndrome", *Neurology*, vol. 54, NO. 8, pp. 1661–1665 (Apr. 25, 2000).

van Dijk, M. et al., "Human antibodies as next generation therapeutics", *Current Opinion in Chemical Biology*, 5:368–374 (2001).

Waurzyniak, B. et al., "In Vivo Toxicity, Pharmacokinestics, and Antileukemic Activity of TXU (Anti–CD7)–Pokeweed Antiviral Protein Immunotoxin", *Clinical Cancer Research*, vol. 3, No. 6, pp. 881–890 (Jun. 1997).

Adams, D. et al., "Tumors undergoing rejection induced by monoclonal antibodies of the IgG2a isotype contain increased numbers of macrophages activated for a distinctive form of antibody–dependent cytolysis", *Proc. Natl. Acad. Sci. USA*, 81:3506–3510 (Jun. 1984).

Allen, J. et al., "Nucleotide sequence of three cDNAs for the human high affinity Fc receptor (FcRI)", *Nucleic Acids Research*, vol. 16, No. 24, pp. 11824 (1988).

Allen, J. et al., "Isolation and Expression of Functional High–Affinity Fc Receptor Complementary DNAs", *Science*, vol. 243, pp. 378–381 (Jan. 20, 1989).

Amigorena, S. et al., "Cytoplasmic Domain Heterogeneity and Functions of IgG Fc Receptors in B Lymphocytes", *Science*, vol. 256, pp. 1808–1812 (Jun. 26, 1992).

Anderson, D. et al., "Targeting Cytotoxic Immunotherapy", *Biochemical Society Transactions*, vol. 25, No. 2, pp. 705–708 (May 1997).

Angal, S. et al., "A Single Amino Acid Substitution Abolishes the Heterogeneity of Chimeric Mouse/Human (IgG4) Antibody", *Molecular Immunology*, vol. 30, No. 1, pp. 105–108 (1993).

Bauer, C. et al., "A genetic enrichment for mutations constructed by oligodeoxynucleotide–directed mutagenesis", *Gene*, 37:73–81 (1985).

Bjorkman, P. et al., "Structure of the human class I histocompatibility antigen, HLA–A2", *Nature*, 329:506–512 (Oct. 8, 1987).

Bowie, J. et al., "Deciphering the Message in Protein Sequences: Tolerance to Amino Acid Substitutions", *Science*, 247:1306–1310 (Mar. 16, 1990).

Brooks, D. et al., "Structure and Expression of Human IgG FcRII(CD32): Functional Heterogencity is Encoded by the Alternatively Spliced Products of Multiple Genes", *The Journal of Experimental Medicine*, vol. 170, No. 4, 1369–1385 (Oct. 1989).

Burton, D., "Immunoglobulin G: Functional Sites", *Molecular Immunology*, vol. 22, No. 3, pp. 161–206 (1985).

Capel, P., et al., "Heterogeneity of Human IgG Fc Receptors", *Immunomethods*. 4:25–34 (1994).

Clark, M. et al., "A single amino acid distinguishes the high–responder from the low–responder form of Fc receptor II on human monocytes", *Eur. J. Immunol.*, 21:1911–1916 (1991).

Clynes, R. et al., "Inhibitory Fc receptors modulate in vivo cytotoxicity against tumor targets", *Nature Medicine*, vol. 6, No. 4, pp. 443–446 (Apr. 2000).

Collins, E. et al., "The three–dimensional structure of a class I major histocompatibility complex molecule mising the α3 domain of the heavy chain", *Proc. Natl. Acad. Sci. USA*, 93:1218–1221 (Feb. 1995).

Cosman, D. et al., "Cloning, sequence and expression of human interleukin–2 receptor", *Nature*, 312:768–771, (Dec. 1984).

Cosman, D. et al., "High Level Stable Expression of Human Interleukin–2 Receptors in Mouse Cells Generates Only Low Affinity Interleukin–2 Binding Sites", *Molecular Immunology*, vol. 23, No. 9, pp. 935–941 (1986).

Coussens, L. et al., "Tyrosine Kinase Receptor with Extensive Homology to EGF Receptor Shares Chromosomal Location with *neu* Oncogene", *Science*, 230:1132–1139 (Dec. 6, 1985).

Craik, C., "Use of Olignucleotides for Site–Specific Mutagenesis", *BioTechniques*, vol. 3, No. 1, pp. 12–19 (Jan./Feb. 1985).

Cunningham, B. et al., "The Complete Amino Acid Sequence of β2–Microglobulin", *Biochemistry*, vol. 12, No. 24, pp. 4811–4822 (Nov. 20, 1973).

De Haas, M. et al., "Fcγ receptors of phagocytes", *The Journal of Laboratory and Clinical Medicine*, vol. 126, No. 4, pp. 330–341 (Oct. 1995).

De Haas, M. et al., "A Triallelic Fcγ Receptor Type IIIA Polymorphism Influences the Binding of Human IgG by NK Cell FcγRIIIa", *The Journal of Immunology*, vol. 156, No. 8, pp. 2948–2955 (Apr. 15, 1996).

Debré, M. et al., "Infusion of Fcγ fragments for treatment of children with acute immune thrombocytopenic purpura", *Lancet*, vol. 342, No. 8877, pp. 945–949 (Oct. 16, 1993).

Deo, Y. et al., "Clinical significance of IgG Fc receptors and FcγR–directed immunotherapies", *Immunology Today*, vol. 18, No. 3, pp. 127–135 (Mar. 1997).

Eaton, D. et al., "Construction and Characterization of an Active Factor VIII Variant Lacking the Central One–Third of the Molecule", *Biochemistry*, vol. 25, No. 26, pp. 8343–8347 (Dec. 30, 1986).

Engelhardt, W. et al., "Distribution, inducibility and biological function of the cloned and expressed human βFc receptor II", *Eur. J. Immunol.*, 20:1367–1377 (1990).

EU Index in Kabat et al., "Sequences of Proteins of Immunological Interest", vol. III, 5th Ed., *Public Health Service*, National Institutes of Health, Bethesa, MD, pp. 2246 (1991).

Gavin, A. et al., "Molecular basis for the interaction of Fc receptors with immunoglobulins", *The Immunoglobulin Receptors and their Physiological and Pathological Roles in Immunity*, pp. 11–35 (1998).

Gessner, J. et al., "The IgG Fc receptor family", *Annals of Hermatology*, vol. 76, No. 5, pp. 231–248 (May 1998).

Gessner, J. et al., "The Human Low Affinity Immunoglobulin G Fc Receptor III–A and III–B Genes", *The Journal of Biological Chemistry*, vol. 270, No. 3, pp. 1350–1361 (Jan. 20, 1995).

Ghetie, V. et al., "FcRn: the MHC class I–related receptor that is more than an IgG transporter", *Immunology Today*, 18:592–598 (Dec. 1977).

Gluzman, Y., "SV40–Transformed Simian Cells Support the Replication of Early SV40 Mutants", *Cell*, vol. 23, No. 1, pp. 175–182 (Jan. 1981).

Gorman, C. et al., "Transient Production of Proteins Using an Adenovirus Transformed Cell Line", *DNA and Protein Engineering Techniques*, vol. 2, No. 1, pp. 3–10 (1990).

Güssow, D. et al., "The Human β2–Microglobulin Gene: Primary Structure and Definition of the Transcriptional Unit", *The Journal of Immunology*, vol. 139, No. 9, pp. 3132–3138 (Nov. 1, 1987).

Hibbs, M. et al., "Molecular cloning of a human immunoglobulin G Fc receptor", *Proc. Natl. Acad. Sci. USA*. 85:2240–2244 (Apr. 1988).

Ierino, F. et al., "Recombinant Soluble Human FcγRII: Production, Characterization, and Inhibition of the Arthus Reaction", *The Journal of Experimental Medicine*, vol. 178, No. 5, pp. 1617–1628 (Nov. 1, 1993).

Koene, H. et al., "FcγRIIIa–158V/F Polymorphism Influences the Binding of IgG by Natural Killer Cell FcγRIIIa, Independently of the FcγRIIIa–48L/R/H Phenotype", *Blood*, vol. 90, No. 3, pp. 1109–1114 (Aug. 1, 1997).

Küster, H., et al., "Characterization and Expression of the Gene for the Human Fc Receptor γ Subunit", *The Journal of Biological Chemistry*, vol. 265, No. 11, pp. 6448–6452 (Apr. 15, 1990).

Lawlor, D. et al., "Comparison of Class I MHC Alleles in Humans and Apes", *Immunological Reviews*, No. 113, pp. 147–185 (1990).

Lehrnbecher, T. et al., "Variant genotypes of FcγRIIIA influence the development of Kaposi's sarcoma in HIV–infected men", *Blood*, vol. 95, No. 7, pp. 2386–2390 (Apr. 1, 2000).

Liu, J. et al., "Characterization of Complex Formation by Humanized Anti–IgE Monoclonal Antibody and Monoclonal Human IgE", *Biochemistry*, vol. 34, No. 33, pp. 10474–10482 (Aug. 22, 1995).

Luckow, V. et al., "Trends in the Development of Baculovirus Expression Vectors", *Bio/Technology*, 6:47–55 (Jan. 1998).

Nieto, A. et al., "Involvement of Fcγ Receptor IIIA Genotypes in Susceptibility to Rheumatoid Arthritis", *Arthritis & Rheumatism*, vol. 43, No. 4, pp. 735–739 (Apr. 2000).

Okayama, H. et al., "A cDNA Cloning Vector that Permits Expression of cDNA Inserts in Mammalian Cells", *Molecular and Cellular Biology*, vol. 3, No. 2, pp. 280–289 (Feb. 1983).

Porges, A. et al., "Novel Fcγ Receptor I Family Gene Products in Human Mononuclear Cells", *The Journal of Clinical Investigation*, vol. 90, No. 5, pp. 2102–2109 (Nov. 1992).

Ravetch, J. et al., "Fc Receptors", *Annu. Rev. Immunol.*, 9:457–492 (1991).

Ravetch, J., "Atopy and Fc receptors: mutation is the message?", *Nature Genetics*, vol. 7, No. 2, pp. 117–118 (Jun. 1994).

Ravetch, J. et al., "Alternative Membrane Forms of FcγRIII(CD16) on Human Natural Killer Cells and Neutrophils", *The Journal of Experimental Medicine*, vol. 170, No. 2, pp. 481–497 (Aug. 1, 1989).

Reff, M. et al., "Depletion of B Cells in Vivo by a Chimeric Mounse Human Monoclonal Antibody to CD20", *Blood*, vol. 83, No. 2, pp. 435–445 (Jan. 15, 1994).

Repp, R. et al., "G–CSF–Stimulated PMN in Immunotherapy of Breast Cancer with a Bispecific Antibody to FcγRI and to HER–2/neu (MDX–210)", *Journal of Hematotherapy*, vol., 4, No. 5, pp. 415–421 (Oct. 1995).

Riethmüller, G. et al., "Randomised trial of monoclonal antibody for adjuvant therapy of resected Dukes' C colorectal carcinoma", vol. 343, No. 8907, pp. 1177–1183 (May 14, 1994).

Rosa, F. et al., "The $\beta_2$-microglobulin mRNA in human Daudi cells has a mutated initiation codon but is still inducible by interferon", *The EMBO Journal*, vol. 2, pp. 239–243 (1983).

Salmon, J. et al., "FcγRIIA Alleles are Heritable Risk Factors for Lupus Nephritis in African Americans", *The Journal of Clinic Investigation*, vol. 97, No. 5, pp. 1348–1354 (Mar. 1996).

Sambrook et al., "Detection and Analysis of Proteins Expressed from Cloned Genes", *Molecular Cloning: A Laboratory Manual*, Chapter 18, pp. 18.2–18.88 (1989).

Saper, M. et al., "Redefined Structure of the Human Histocompatibility Antigen HLA–A2 at 2.6 Å Resolution", *Journal of Molecular Biology*, vol. 219, No. 2, pp. 277–319 (May 20, 1991).

Seki', T., "Identification of multiple isoforms of the low–affinity human IgG Fc receptor", *Immunogenetics*, 30:5–12 (1989).

Shields, R. et al., "High Resolution Mapping of the Binding Site on Human IgG1 for FcγRI, FcγII, FcγRIII, and FcRn and Design of IgG1 Variants with Improved Binding to the FcγR", *The Journal of Biological Chemistry*, vol. 276, No. 9, pp. 6591–6064 (Mar. 2, 2001).

Smith, T. et al., "Comparison of Biosequences", *Advances in Applied Mathermatics*, vol. 2, No. 4, pp. 482–489 (Dec. 1981).

Stengelin, S. et al., "Isolation of cDNAs for two distinct human Fc receptors by ligand affinity cloning", *The EMBO Journal*, vol. 7, No. 4, pp. 1053–1059 (Apr. 1988).

Story, C. et al., "A Major Histocompatibility Complex Class–I–Like Fc Receptor Cloned from Human Placenta: Possible Role in Transfer of Immunoglobulin G from Mother to Fetus", *The Journal of Experimented Medicine*, vol. 180, No. 6, pp. 2377–2381 (Dec. 1, 1994).

Stuart, S. et al., "Isolation and Expression of cDNA Clones Encoding a Human Receptor for IgG (FcγRII)", *The Journal of Experimental Medicine*, vol. 166, No. 6, pp. 1668–1684 (Dec. 1, 1987).

Suggs, S. et al., "Use of Synthetic oligonucleotides as hybridization probes: Isolation of cloned cDNA sequences for human $\beta_2$–microglobulin", *Proc. Natl. Acad. Sci. USA*, vol. 78, No. 11, pp. 6613–6617 (Nov. 1981).

Takahashi, H. et al., "Inhibition of Hepatic Metastases of Human Colon Cancer in Nude Mice by a Chimeric SF–25 Monoclonal Antibody", *Gastroenterology*, vol. 108, No. 1, pp. 172–182 (Jan. 1995).

Valone, F. et al., "Phase Ia/Ib Trial of Bispecific Antibody MDX–210 in Patients with Advanced Breast or Ovarian Cancer that Overexpresses the Proto–Oncogene HER–2/neu", *Journal of Clinical Oncology*, vol. 13, No. 9, pp. 2281–2292 (Sep. 1995).

Van de Winkel, J. et al., "Human IgG Fc receptor heterogeneity: molecular aspects and clinical implications", *Immunology Today*, vol. 14, No. 5, pp. 215–221 (1993).

Walder, R. et al., "Oligodeoxynucleotide–directed mutagenesis using the yeast transformation system", *Gene*, 42:133–139 (1986).

Warmerdam, P. et al., "A Single Amino Acid in the Second Ig–Like Domain of the Human Fcγ Receptor II is Critical for Human IgG2 Binding", *The Journal of Immunology*, vol. 147, No. 4, pp. 1338–1343 (Aug. 15, 1991).

West, Jr., A et al., "Crystal Structure and Immunoglobulin G Binding Properties of the Human Major Histocompatibility Complex–Related Fc Receptor", *Biochemistry*, 39:9698–9708 (2000).

Wu, J. et al., "A Novel Polymorphism of FcγRIIIa (CD16) Alters Receptor Function and Predisposes to Autoimmune Disease", *The Journal of Clinical Investigation*, vol. 100, No. 5, pp. 1059–1070 (Sep. 1997).

NON-HUMAN PRIMATE FC RECEPTORS AND METHODS OF USE

FIELD OF THE INVENTION

The invention generally relates to purified and isolated non-human primate Fc receptor polypeptides, the nucleic acid molecules encoding the FcR polypeptides, and the processes for production of non-human primate Fc receptor polypeptides as well as to methods for evaluating the safety, efficacy and biological properties of therapeutic agents.

BACKGROUND OF THE INVENTION

Fc receptors (FcRs) are membrane receptors expressed on a number of immune effector cells. Upon interaction with target immunoglobulins, FcRs mediate a number of cellular responses, including, activation of cell mediated killing, induction of mediator release from the cell, uptake and destruction of antibody coated particles, and transport of immunoglobulins. Deo et al., 1997, *Immunology Today* 18:127–135. Further, it has been shown that antigen-presenting cells, e.g., macrophages and dendritic cells, undergo FcR mediated internalization of antigen-antibody complexes, allowing for antigen presentation and the consequent amplification of the immune response. As such, FcRs play a central role in development of antibody specificity and effector cell function. Deo et al., 1997, *Immunology Today* 18:127–135.

FcRs are defined by their specificity for immunoglobulin isotypes; Fc receptors for IgG antibodies are referred to as FcγR, for IgE as FcεR, for IgA as FcαR and so on. FcRn is a special class of Fc receptor found on neonatal cells and is responsible for, among other things, transporting maternal IgG from milk across the infants intestinal epithelial cells. Three subclasses of human gamma receptors have been identified: FcγRI (CD64), FcγRII (CD32) and FcγRIII (CD16). Because each human FcγR subclass is encoded by two or three genes, and alternative RNA spicing leads to multiple transcripts, a broad diversity in Fcγ isoforms exists. The three genes encoding the human FcγRI subclass (FcγRIA, FcγRIB and FcγRIC) are clustered in region 1q21.1 of the long arm of chromosome 1; the genes encoding FcγRII isoforms (FcγRIIA, FcγRIIB and FcγRIIC) and the two genes encoding FcγRIII (FcγRIIIA and FcγRIIIB) are all clustered in region 1q22. FcRs are reviewed in Ravetch and Kinet, Annu. Rev. Immunol 9:457–92 (1991); Capel et al., Immunomethods 4:25–34 (1994); and de Haas et al., J Lab. Clin. Med. 126:330–41 (1995).

Human FcγRI is a heteroligomeric complex composed of an α-chain and γ-chain. The α-chain is a 70–72 kDa glycoprotein having 3 extracellular C-2 Ig like domains, a 21 amino acid membrane domain and a charged cytoplasmic tail of 61 amino acids. van de Winkel et al., 1993, *Immunology Today* 14:215–221. The γ-chain is a homodimer that is involved in cell surface assembly and cell signaling into the interior of the cell. Each chain of γ homodimer includes a motif involved in cellular activation designated the ITAM motif. Human FcγRI binds monomeric IgG with high affinity ($10^{-7}$–$10^{-9}$M) through the action of the third extracellular C-2 domain.

FcγRII is a 40 kDa glycoprotein having two C2 set Ig-like extracellular domains, a 27–29 amino acid transmembrane domain, and a cytoplasmic domain having variable length, from 44 to 76 amino acids. There are six known isoforms of the human FcγRII, differing for the most part in their heterogeneous cytoplasmic domains. Human FcγRIIA includes an ITAM motif in the cytoplasmic region of the molecule, and upon crosslinking of the receptor this motif is associated with cellular activation. In contrast, human FcγRIIB includes an inhibitory motif in its cytoplasmic region designated ITIM. When the FcγRIIB is crosslinked, cellular activation is inhibited. In general, FcγRII binds monomeric IgG poorly (>$10^7$ M$^{-1}$), but has high affinity for complexed IgG.

Human FcγRIII has two major isoforms, FcγRIIIA and FcγRIIIB, both isoforms are between 50 to 80 kDa, having two C2 Ig-like extracellular domains. The FcγRIIIA α-chain is anchored to the membrane by a 25 amino acid transmembrane domain, while FcγRIIIB is linked to the membrane via a glycosyl phosphatidyl-inositol (GPI) anchor. Human FcγRIIIA is a heteroligomeric complex with the α-chain complexed with a heterodimeric γ-δ (gamma-delta) chain or γ-γ chain. The γ-chain includes a cytoplasmic tail with an ITAM motif. The γ-chain is homologous to the α-chain and is also involved in cell signaling and cell surface assembly. The γ-δ (gamma-delta) chain also includes an ITAM motif in its cytoplasmic region. In both cases, the FcγRIII binds monomeric IgG with low affinity, and binds complexed IgG with high affinity.

Human FcRn is a heterodimer composed of a β-2 microglobulin chain and a α chain. The β-2 microglobulin chain is approximately 15 kDa and is similar to the β-2 microglobulin chain present in MHC class I heterodimers. The presence of a β-2 microglobulin chain in FcRn makes it the only known Fc receptor to fall within the MHC class I family of proteins. Ghetie et al., 1997 *Immunology Today* 18(12):592–598. The a chain is a 37–40 kDa integral membrane glycoprotein having a single glycosylation site. Evidence suggests that FcRn is involved in transferring maternal IgG across the neonatal gut and in regulating serum IgG levels. FcRn is also found in adults on many tissues.

As discussed above, human FcγRs, with the exception of FcγRIIB, contain a cytoplasmic ~26 amino acid immunoreceptor tyrosine-based activation motif (ITAM). It is believed that this motif is involved in cell signaling and effector cell function. Crosslinking of FcγRs may lead to the phosphorylation of tyrosine residues within the ITAM motif by src-family tyrosine kinases (PTKs), followed by association and activation of the phosphorylated ITAM motif with syk-family PTKs. Deo et al., 1997, *Immunology Today* 18:127–135. Once activated, a poorly understood signaling cascade is translated into biological responses.

Human FcγRIIB members contain a distinct 13 amino acid immuno-receptor tyrosine-based inhibitory motif (ITIM) in their cytoplasmic domain. Human FcγRIIB is expressed on B lymphocytes and binds to IgG complexes. However, rather than activating cells, crosslinking of the IIB receptor results in a signal inhibiting B cell activation and antibody secretion. (Camigorea et al., 1992, *Cytoplasmic Domain Heterogeneity and Function of IgG Receptors in B Lymphocytes, Science* 256:1808.)

Because of the central role of FcγR as a trigger molecule in numerous immune responses, it has become a target for developing potential therapeutics. For example, several ongoing clinical trials are based on activating a cancer patient's effector cells by treating the patient with tumor-specific monoclonal antibodies (Mabs). These studies have shown that the tumor-specific antibodies mediate their effects in part through FcγR binding, and subsequent effector cell activity. Adams et al., 1984, *Proc. Natl. Acad. Sci.* 81:3506–3510; Takahashi et al., 1995, *Gastroenterology* 108:172–182; Riethmeuller et al., 1994, *Lancet*

343:1177–1183, Clynes, R. A., Towers, T. L., Presta, L. G., and Ravetch, J. V., 2000, *Nature Med.* 6:443–446. Further, a novel series of bispecific molecule antibodies (BSMs), molecules engineered to have one arm specific for a tumor cell and the other arm specific for a target FcγR, are in clinical trials to specifically target a tumor for FcγR mediated, effector cell destruction of the tumor cells. Valone et al., 1995, *J. Clin. Oncol.* 13:2281–2292; Repp et al., 1995, *Hematother* 4:415–421. In addition, FcγRs can be used as therapeutic targets in a number of infectious diseases, and for that matter, a number of autoimmune disorders. With regard to infectious diseases, BSMs are being developed to target any number of microorganisms to a patient's FcγR expressing effector cells (Deo et al., 1997, *Immunology Today* 18:127–135), while soluble FcγRs have been used to inhibit the Arthus reaction, and FcγR blocking agents have been used to reduce the severity of several autoimmune disorders. Ierino et al., 1993, *J. Exp. Med.* 178:1617–1628; Debre et al., 1993, *Lancet* 342:945–949.

As antibodies have become increasingly used as therapeutic agents, there is a need to develop animal models for evaluating the toxicity, efficacy and pharmacokinetics of such therapeutic agents. In addition to rodent models for evaluating efficacy of antibody therapeutics, primate models have been used for evaluation of therapeutic antibody pharmacokinetics, toxicity, and efficacy (Anderson, D. R., Grillo-Lopez, A., Varns, C., Chambers, K. S., and Hanna, N. (1997) Biochem. Soc. Trans. 25, 705–708). However, there is only sparse information available regarding the interaction of human antibodies with primate Fcγ receptors and the effects of this interaction on interpretation of pharmacokinetic, toxicity, and efficacy studies in primates.

Although many advances have been made in elucidating FcγR activity and identifying and engineering FcγR ligands, there still remains a need in the art to identify other FcγRs and to identify and engineer other FcγR ligands, both activating and inhibiting. These new receptors and receptor ligands possess potential therapeutic value in a number of disease states, including, the destruction of tumor cells and infectious material, as well as in blocking portions of the immune response involved in several autoimmune disorders. As antibodies and other FcγR ligands are used as therapeutic agents, there is also a need to develop models to test the efficacy, toxicity, and pharmacokinetics of these therapeutic agents, especially in vivo.

SUMMARY OF INVENTION

The invention is based upon, among other things, the isolation and sequencing of polynucleotides encoding Fc receptor polypeptides from non-human primates, such as cynomolgus monkeys and chimps. The cynomolgus monkey or chimp FcR polynucleotides and polypeptides of the invention are useful, inter alia, for evaluation of binding of antibodies of any subclass (especially antibodies with prospective therapeutic utility) to cynomolgus or chimpanzee FcR polypeptides prior to in vivo evaluation in a primate.

The invention provides polynucleotide molecules encoding non-human primate Fc receptor polypeptides. The polynucfeotides of the invention encode non-human primate Fc receptor polypeptides with an amino acid sequence of SEQ ID NO: 9, SEQ ID NO: 11, SEQ ID NO: 15, SEQ ID NO: 17, SEQ ID NO: 18, SEQ ID NO: 20, SEQ ID NO: 25, SEQ ID NO. 29, SEQ ID NO. 64 or fragments thereof. Fc receptor polynucleotide molecules of the invention include those molecules having a nucleic acid sequence as shown in SEQ ID NOs: 1, 3, 5, 7, 13, 22, and 27, as well as polynucleotides having substantial nucleic acid identity with the nucleic acid sequences of SEQ ID NOs 1, 3, 5, 7, 13, 22, and 27. β-2 microglobulin polynucleotide molecules of the invention also include molecules having a nucleic acid sequence as shown in SEQ ID NO: 23, as well as polynucleotides having substantial nucleic acid identity with the nucleic acid sequences of SEQ ID NO: 23.

The present invention also provides non-human primate Fcγ receptors and non-human primate β-2 microglobulin. Fcγ polypeptides of the invention include those having an amino acid sequence shown in SEQ ID NOs: 9, 11, 15, 17, 18, 20, 29, and 64 as well as polypeptides having substantial amino acid sequence identity to the amino acid sequences of SEQ ID NOs 9, 11, 15, 17, 18, 20, 29, and 64 and useful fragments thereof. β-2 microglobulin polypeptides of the invention include those having an amino acid sequence shown in SEQ ID NO: 25, as well as polypeptides having substantial amino acid sequence identity to the amino acid sequence of SEQ ID NO: 25 and useful fragments thereof.

In another aspect the invention provides polynucleotide molecules encoding mature non-human primate Fc receptor polypeptides. The polynucleotides of the invention encode mature non-human primate Fc receptor polypeptides with an amino acid sequence of SEQ ID NO: 65, SEQ ID NO: 66, SEQ ID NO: 67, SEQ ID NO: 68, SEQ ID NO: 69, SEQ ID NO: 70, SEQ ID NO. 71, SEQ ID NO. 72 or fragments thereof. Fc receptor polynucleotide molecules of the invention include those molecules having a nucleic acid sequence as shown in SEQ ID NOs: 1, 3, 5, 7, 13, 22, 23 and 27, as well as polynucleotides having substantial nucleic acid identity with the nucleic acid sequences of SEQ ID NOs 1, 3, 5, 7, 13, 22, 23, and 27.

In another aspect of the invention, a method of obtaining a nucleic acid encoding a nonhuman primate Fc receptor is provided. The method comprises amplifying a nucleic acid from a nonhuman primate cell with a primer set comprising a forward and a reverse primer, wherein the primer sets are selected from the group consisting of SEQ ID NO:31 and SEQ ID NO:32, SEQ ID NO:33 and SEQ ID NO:34, SEQ ID NO:35 and SEQ ID NO:36, SEQ ID NO:37 and SEQ ID NO:38, SEQ ID NO:39 and SEQ ID NO:40, SEQ ID NO:41 and SEQ ID NO:42, SEQ ID NO:43 and SEQ ID NO:44, SEQ ID NO:45 and SEQ ID NO:46, SEQ ID NO:47 and SEQ ID NO:48, SEQ ID NO:49 and SEQ ID NO:50, SEQ ID NO:51 and SEQ ID NO:52, and SEQ ID NO:53 and SEQ ID NO:54; and isolating the amplified nucleic acid. The nonhuman primate cell is a preferably a cynomologus spleen cell or a chimp spleen cell.

The invention includes variants, derivatives, and fusion proteins of the non-human primate Fcγ receptor polypeptides and β-2 microglobulin. For example, the fusion proteins of the invention include the non-human primate Fcγ receptor polypeptides fused to heterologous protein or peptide that confers a desired function, i.e., purification, stability, or secretion. The fusion proteins of the invention can be produced, for example, from an expression construct containing a polynucleotide molecule encoding one of the polypeptides of the invention in frame with a polynucleotide molecule encoding the heterologous protein.

The invention also provides vectors, plasmids, expression systems, host cells, and the like, containing the polynucleotides of the invention. Several recombinant methods for the production of the polypeptides of the invention include expression of the polynucleotide molecules in cell free expression systems, in cellular hosts, in tissues, and in animal models, according to known methods.

The non-human primate Fcγ receptors are useful in animal models for the evaluation of the therapeutic safety, efficacy and pharmacokenetics of agents, especially agents having a Fc region. A method of the invention involves contacting an agent with Fc receptor binding domain with a non-human primate Fc receptor polypeptide, preferably a mature soluble polypeptide, and determining the effect of contact on at least biological property of the Fc region containing molecule. A method of the invention involves contacting a cell expressing at least one non-human primate Fcγ receptor polypeptide with an agent having a Fc region and determining whether the agent alters biological activity of the cell or is toxic to the cell. The invention also includes a method for screening variants of agents including an Fc region for the ability of such variants to bind to and activate FcRs. An example of such variants include antibodies that have amino acid substitutions at specific residues that may alter binding affinity for one or more Fc receptor classes.

Another example, of screening for agents with FcR binding domains includes identifying agents that have an altered affinity for a Fcγ receptor having an ITAM region compared to a Fcγ receptor having an ITIM region. In addition, the invention provides reagents, compositions, and methods that are useful identifying an agent that has an altered affinity for a Fcγ receptor having an ITIM region, or for a method for identifying an agent with increased binding affinity for a Fcγ receptor having an ITAM region.

These and various other features as well as advantages which characterize the invention will be apparent from a reading of the following detailed description and a review of the appended claims.

BRIEF DESCRIPTION OF THE FIGURES

FIG. 1A: FIG. 1A illustrates monomeric IgG subclass binding to human FcγRI.

FIG. 1B: FIG. 1B illustrates monomeric IgG subclass binding to cynomolgus FcγRI.

FIG. 2: FIG. 2 illustrates hexameric immune complex binding to cynomolgus FcγRIIA.

FIG. 3A: FIG. 3A illustrates hexameric immune complex binding to human FcγRIIB.

FIG. 3B: FIG. 3B illustrates hexameric immune complex binding to cynomolgus FcγRIIB.

FIG. 4A: FIG. 4A illustrates hexameric immune complex binding to human FcγRIIIA-F158.

FIG. 4B: FIG. 4B illustrates hexameric immune complex binding to human FcγRIIIA-V158.

FIG. 4C: FIG. 4C illustrates hexameric immune complex binding to cynomolgus FcγRIIIA.

FIG. 5: FIG. 5 illustrates hexameric immune complex binding of human IgG1 variants to cynomolgus FcγRIIA.

FIG. 6: FIG. 6 illustrates hexameric immune complex binding of human IgG variants to cynomolgus FcγRIIB.

FIG. 7: FIG. 7 illustrates hexameric immune complex binding of human IgG variants to cynomolgus FcγRIIIA.

FIG. 8: FIG. 8 illustrates concentration dependent monomeric IgG subclass binding to human FcRn.

FIG. 9: FIG. 9 illustrates concentration dependent monomeric IgG subclass binding to cynomolgus FcRn (S3).

FIG. 10: FIG. 10 illustrates concentration dependent monomeric IgG subclass binding to cynomolgus FcRn (N3).

IDENTIFICATION OF SEQUENCES AND SEQUENCE IDENTIFIERS

| SEQ ID NO. | DESCRIPTION | LOCATION | ACCESSION NO. |
|---|---|---|---|
| 1 | Cynomolgus DNA for a FcγRI α-chain | Table 3 | — |
| 2 | Human DNA for a FcγRI α-chain | Table 3 | GenBank L03418 |
| 3 | Cynomolgus DNA for a FcγRIIA | Table 5 | — |
| 4 | Human DNA for a FcγRIIA | Table 5 | GenBank M28697 |
| 5 | Cynomolgus DNA for a FcγRIIB | Table 6 | — |
| 6 | Human DNA for a FcγRIIB | Table 6 | Genbank X52473 |
| 7 | Cynomolgus DNA for a FcγRIIIA α-chain | Table 7 | — |
| 8 | Human DNA for a FcγRIIIA α-chain | Table 7 | GenBank X52645 |
| 9 | Amino acid sequence of a cynomolgus FCγRI α-chain | Table 10 | — |
| 10 | Amino acid sequence of a human FcγRI α-chain | Table 10 | GenBank P12314 |
| 11 | Amino acid sequence of a cynomolgus FcγRI/III gamma chain | Table 12 | — |
| 12 | Amino acid sequence of a human FcγRI/III gamma chain | Table 12 | GenBank P30273 |
| 13 | DNA sequence for a cynomolgus gamma chain DNA | Table 4 | — |
| 14 | DNA sequence for a human gamma chain DNA | Table 4 | GenBank M33195 |
| 15 | Amino acid sequence of a cynomolgus FcγRIIA | Table 11 | — |
| 16 | Amino acid sequence of a human FcγRIIA | Table 11 | GenBank P12318 |
| 17 | Amino acid sequence of a chimp FcγRIIA | Table 11 | — |
| 18 | Amino acid sequence of a cynomolgus FcγRIIB | Table 11 | — |
| 19 | Amino acid sequence of a human FcγRIIB | Table 11 | GenBank X52473 |
| 20 | Amino acid sequence of a cynomolgus FcγRIIIA α-chain | Table 11 | — |
| 21 | Amino acid sequence of a human FcγRIIIA α-chain | Table 11 | GenBank P08637 |
| 22 | DNA sequence for a chimp FcγRIIA | Table 5 | — |
| 23 | Cynomolgus B-2 micro-globulin DNA | Table 8 | |
| 24 | Human B-2 microglobulin DNA | Table 8 | AB 021288 |
| 25 | Amino acid sequence of cynomolgus B-2 micro-globulin | Table 13 | — |
| 26 | Amino acid sequence of human β-2 microglobulin | Table 13 | P01884 |
| 27 | Cynomolgus FcRn α-chain DNA | Table 9 | — |
| 28 | Human FcRn α-chain DNA | Table 9 | U12255 |
| 29 | Amino acid sequence of cynomolgus FcRn α-chain (S3) | Table 14 | — |
| 30 | Amino acid sequence of human FcRn α-chain | Table 14 | U12255 |
| 31 | Cynomolgus FcγRI full-length forward primer | Table 1 | |
| 32 | Cynomolgus FcγRI full-length reverse primer | Table 1 | |
| 33 | Cynomolgus FcγRI-H6-GST forward primer | Table 1 | |
| 34 | Cynomolgus FcγRI-H6-GST reverse primer | Table 1 | |
| 35 | Cynomolgus FcγRIIB full-length forward primer | Table 1 | |

-continued

| SEQ ID NO. | DESCRIPTION | LOCATION | ACCESSION NO. |
|---|---|---|---|
| 36 | Cynomolgus FcγRIIB full-length reverse primer | Table 1 | |
| 37 | Cynomolgus FcγRIIB-H6-GST forward primer | Table 1 | |
| 38 | Cynomolgus FcγRIIB-H6-GST reverse primer | Table 1 | |
| 39 | Cynomolgus FcγRIIIA full-length forward primer | Table 1 | |
| 40 | Cynomolgus FcγRIIIA full-length reverse primer | Table 1 | |
| 41 | Cynomolgus FcγRIIIA-H6-GST forward primer | Table 1 | |
| 42 | Cynomolgus FcγRIIIA-H6-GST reverse primer | Table 1 | |
| 43 | Cynomolgus Fc gamma chain forward primer | Table 1 | |
| 44 | Cynomolgus Fc gamma chain reverse primer | Table 1 | |
| 45 | Cynomolgus β-2 Microglobulin forward primer | Table 1 | |
| 46 | Cynomolgus β-2 Microglobulin reverse primer | Table 1 | |
| 47 | Cynomolgus FcγRIIA full-length forward primer | Table 1 | |
| 48 | Cynomolgus FcγRIIA full-length reverse primer | Table 1 | |
| 49 | Cynomolgus FcγRIIA-H6-GST forward primer | Table 1 | |
| 50 | Cynomolgus FcγRIIA-H6-GST reverse primer | Table 1 | |
| 51 | Cynomolgus FcRn full-length forward primer | Table 1 | |
| 52 | Cynomolgus FcRn full-length reverse primer | Table 1 | |
| 53 | Cynomolgus FcRn-H6 forward primer | Table 1 | |
| 54 | Cynomolgus FcRn-H6 reverse primer | Table 1 | |
| 55 | PCR primer 0F1 | Table 2 | |
| 56 | PCR primer 0R1 | Table 2 | |
| 57 | PCR primer 0F2 | Table 2 | |
| 58 | PCR primer 0F3 | Table 2 | |
| 59 | PCR primer 0R2 | Table 2 | |
| 60 | PCR primer 0F4 | Table 2 | |
| 61 | PCR primer 0R3 | Table 2 | |
| 62 | PCR primer 0F5 | Table 2 | |
| 63 | PCR primer 0R4 | Table 2 | |
| 64 | Amino acid sequence of cynomologus FcRn α-chain (N3) | Table 14 | |
| 65 | Amino acid sequence of a mature cynomolgus FcγRI α-chain | Table 10 | |
| 66 | Amino acid sequence of a mature cynomolgus FcγRIIA | Table 11 Table 21 | |
| 67 | Amino acid sequence of a mature chimp FcγRIIA | Table 11 | |
| 68 | Amino acid sequence of a mature cynomolgus FcγRIIB | Table 11 Table 22 | |
| 69 | Amino acid sequence of a mature cynomolgus FcγRIIIA α-chain | Table 11 Table 23 | |
| 70 | Amino acid sequence of a mature cynomolgus β-2 microglobulin | Table 13 | |
| 71 | Amino acid sequence of a mature cynomolgus FcγRn α-chain (S3) | Table 14 | |
| 72 | Amino acid sequence of a mature cynomolgus FcRn α-chain (N3) | Table 14 | |

DETAILED DESCRIPTION OF THE INVENTION

The following definitions are provided to facilitate understanding of certain terms used frequently herein and are not meant to limit the scope of the present disclosure.

Throughout the present specification and claims, the numbering of the residues in an IgG heavy chain is that of the EU index as in Kabat et al., Sequences of Proteins of Immunological Interest, 5th Ed. Public Health Service, National Institutes of Health, Bethesda, Md. (1991), expressly incorporated herein by reference. The "EU index as in Kabat" refers to the residue numbering of the human IgG1 EU antibody.

The term "amino acids" refers to any of the twenty naturally occurring amino acids as well as any modified amino acid sequences. Modifications may include natural processes such as posttranslational processing, or may include chemical modifications which are known in the art. Modifications include but are not limited to: phosphorylation, ubiquitination, acetylation, amidation, glycosylation, covalent attachment of flavin, ADP-ribosylation, cross linking, iodination, methylation, and alike.

The term "antibody" is used in the broadest sense and specifically covers monoclonal antibodies (including full length monoclonal antibodies), polyclonal antibodies, multispecific antibodies (e.g., bispecific antibodies), chimeric antibodies, humanized antibodies, fully synthetic antibodies, and antibody fragments so long as they exhibit the desired biological activity.

The term "antisense" refers to polynucleotide sequences that are complementary to a target "sense" polynucleotide sequence.

The term "complementary" or "complementarity" refers to the ability of a polynucleotide in a polynucleotide molecule to form a base pair with another polynucleotide in a second polynucleotide molecule. For example, the sequence A-G-T is complementary to the sequence T-C-A. Complementarity may be partial, in which only some of the polynucleotides match according to base pairing, or complete, where all the polynucleotides match according to base pairing.

The term "expression" refers to transcription and translation occurring within a host cell. The level of expression of a DNA molecule in a host cell may be determined on the basis of either the amount of corresponding mRNA that is present within the cell or the amount of DNA molecule encoded protein produced by the host cell (Sambrook et al., 1989, *Molecular cloning: A Laboratory Manual*, 18.1–18.88).

The term "Fc region" is used to define a C-terminal region of an immunoglobulin heavy chain. Although the boundaries of the Fc region of an IgG heavy chain might vary slightly, the human IgG heavy chain Fc region stretches from amino acid residue at position Cys226 to the carboxyl-terminus. The term "Fc region-containing molecule" refers to an molecule, such as an antibody or immunoadhesin, which comprises an Fc region. The Fc region of an IgG comprises two constant domains, CH2 and CH3. The "CH2" domain of a human IgG Fc region (also referred to as "Cγ2" domain) usually extends from amino acid 231 to amino acid 340. The CH2 domain is unique in that it is not closely paired with another domain. Rather, two N-linked branched carbohydrate chains are interposed between the two CH2 domains of an intact native IgG molecule. Burton, Molec. Immunol.22:161–206 (1985).

The term "Fc receptor" refers to a receptor that binds to the Fc region of an antibody or Fc region containing molecule. The preferred Fc receptor is a receptor which binds an IgG antibody (FcγR) and includes receptors of the FcγRI, FcγRII, FcγRIII, and FcRn subclasses, including allelic variants and alternatively spliced forms of these receptors. The term "FcR polypeptide" is used to describe a polypeptide that forms a receptor that binds to the Fc region of an antibody or Fc region containing molecule. The term "Fc receptor polypeptide" also includes both the mature polypeptide and the polypeptide with the signal sequence. The term "FcγR polypeptide" is used to describe a polypeptide that forms a receptor that binds to the Fc region of an IgG antibody or IgG Fc region containing molecule. For example, FcγRI and FcγRII receptors each include a Fc receptor polypeptide α-chain and a Fc receptor polypeptide homo or heterodimer of a γ-chain. FcRn receptors include an Fc receptor polypeptide alpha chain and a β-2 microglobulin. Typically, the α-chains have the extracellular regions that bind to the Fc-region containing agent. FcRs are reviewed in Ravetch and Kinet, Annu. Rev. Immunol 9:457–92 (1991); Capel et al., Immunomethods 4:25–34 (1994); and de Haas et al., J. Lab. Clin. Med. 126:330–41 (1995). Other FcRs, including those to be identified in the future, are encompassed by the term "FcR" herein.

The term "fragment" is used to describe a portion of an Fc receptor polypeptide or a nucleic acid encoding a portion of an Fc receptor polypeptide. The fragment is preferably capable of binding to a Fc region containing molecule. The structure of human Fcγ α-chain of FcγRI/III and FcγRIIA or B has been characterized and includes a signal sequence, 2 or 3 extracellular C-2 Ig like domains; a transmembrane domain; and an intracellular cytoplasmic tail. Fragments of an Fc receptor α-chain or FcγRIIA or B include, but are not limited to, soluble Fc receptor polypeptides with one or more of the extracellular C-2 Ig like domains, the transmembrane domain, or intracellular domain of the Fc receptor polypeptides.

The term "binding domain" refers to the region of a polypeptide that binds to another molecule. In the case of an Fc receptor polypeptide or FcR, the binding domain can comprise a portion of a polypeptide chain thereof (e.g. the α-chain thereof) which is responsible for binding an Fc region of an immunoglobulin or other Fc region containing molecule. One useful binding domain is the extracellular domain of an Fc receptor α-chain polypeptide.

The term "fusion protein" is a polypeptide having two portions combined where each of the portions is a polypeptide having a different property. This property may be a biological property, such as activity in vitro or in vivo. The property may also be a simple chemical or physical property, such as binding to a target molecule, catalysis of a reaction etc. The two portions may be linked directly by a single peptide bond or through a peptide linker containing one or more amino acid residues. The fused polypeptide may be used, among other things, to determine the location of the fusion protein in a cell, enhance the stability of the fusion protein, facilitate the oligomerization of the protein, or facilitate the purification of the fusion protein. Examples of such fusion proteins include proteins expressed as fusion with a portion of an immunoglobulin molecule, proteins expressed as fusion proteins with a leucine zipper moiety, Fc receptors polypeptides fused to glutathione S-transferase, and Fc receptor polypeptides fused with one or more amino acids that serve to allow detection or purification of the receptor such as Gly6-His tag.

The term "homology" refers to a degree of complementarity or sequence identity between polynucleotides.

The term "host cell" or "host cells" refers to cells established in ex vivo culture. It is a characteristic of host cells discussed in the present disclosure that they be capable of expressing Fc receptors. Examples of suitable host cells useful for aspects of the present invention include, but are not limited to, insect and mammalian cells. Specific examples of such cells include SF9 insect cells (Summers and Smith, 1987, Texas Agriculture Experiment Station Bulletin, 1555), human embryonic kidney cells (293 cells), Chinese hamster ovary (CHO) cells (Puck et al., 1958, *Proc. Natl. Acad. Sci. USA* 60, 1275–1281), human cervical carcinoma cells (HELA) (ATCC CCL 2), human liver cells (Hep G2) (ATCC HB8065), human breast cancer cells (MCF-7) (ATCC HTB22), and human colon carcinoma cells (DLD-1) (ATCC CCL 221), Daudi cells (ATCC CRL-213), and the like.

The term "hybridization" refers to the pairing of complementary polynucleotides during an annealing period. The strength of hybridization between two polynucleotide molecules is impacted by the homology between the two molecules, stringency of the conditions involved, the melting temperature of the formed hybrid and the G:C ratio within the polynucleotides.

As used herein, the term "immunoadhesin" designates antibody-like molecules which combine the "binding domain" of a heterologous "adhesin" protein (e.g. a receptor, ligand or enzyme) with one or more immunoglobulin constant domains. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence is preferably the Fc portion of an immunoglobulin.

"Immune complex" refers to the relatively stable structure which forms when at least one target molecule and at least one Fc region-containing polypeptide bind to one another forming a larger molecular weight complex. Examples of immune complexes are antigen-antibody aggregates and target molecule-immunoadhesin aggregates. Immune complex can be administered to a mammal, e.g. to evaluate clearance of the immune complex in the mammal or can be used to evaluate the binding properties of FcR or Fc receptor polypeptides.

The term "isolated" refers to a polynucleotide or polypeptide that has been separated or recovered from at least one contaminant of its natural environment. Contaminants of one natural environment are materials, which would interfere with using the polynucleotide or polypeptide therapeutically or in assays. Ordinarily, isolated polypeptides or polynucleotides are prepared by at least one purification step.

A "native sequence" polypeptide refers to a polypeptide having the same amino acid sequence as the corresponding polypeptide derived from nature. The term specifically encompasses naturally occurring truncated or secreted forms of the polypeptide, naturally occurring variant forms (e.g. alternatively spliced forms) and naturally occurring allelic variants. A "mature polypeptide" refers to a polypeptide that does not contain a signal peptide.

The term "nucleic acid sequence" refers to the order or sequence of deoxyribonucleotides along a strand of deoxyribonucleic acid. The order of these deoxyribonucleotides determines the order of amino acids along a polypeptide chain. The deoxyribonucleotide sequence thus codes for the amino acid sequence.

The term "polynucleotide" refers to a linear sequence of nucleotides. The nucleotides are either a linear sequence of polyribonucleotides or polydeoxyribonucleotides, or a mixture of both. Examples of polynucleotides in the context of the present invention include—single and double stranded DNA, single and double stranded RNA, and hybrid molecules that have both mixtures of single and double stranded DNA and RNA. Further, the polynucleotides of the present invention may have one or more modified nucleotides.

The terms, "protein," "peptide," and "polypeptide" are used interchangeably to denote an amino acid polymer or a set of two or more interacting or bound amino acid polymers.

The term "purify," or "purified" refers to a target protein that is free from at least 5–10% of the contaminating proteins. Purification of a protein from contaminating proteins can be accomplished through any number of well known techniques, including, ammonium sulfate or ethanol precipitation, anion or cation exchange chromatography, phosphocellulose chromatography, hydrophobic interaction chromatography, affinity chromatography, hydroxylapatite chromatography and lectin chromatography. Various protein purification techniques are illustrated in Current Protocols in Molecular Biology, Ausubel et al., eds. (Wiley & Sons, New York, 1988, and quarterly updates).

The term "Percent (%) nucleic acid or amino acid sequence identity" describes the percentage of nucleic acid sequence or amino acid residues that are identical with amino acids in a reference polypeptide, after aligning the sequence and introducing gaps, if necessary to achieve the maximum sequence identity, and not considering any conservative substitutions as part of the sequence identity. For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Preferably, % sequence identity can be determined by aligning the sequences manually and again multiplying 100 times the fraction X/Y, where X is the number of amino acids scored as identical matches by manual comparison and Y is the total number of amino acids in B. Further, the above described methods can also be used for purposes of determining % nucleic acid sequence identity. Alternatively, computer programs commonly employed for these purposes, such as the Gap program (Wisconsin Sequence Analysis Package, Version 8 for Unix, Genetics Computer Group, University Research Park, Madison Wis.), that uses the algorithm of Smith and Waterman, 1981, *Adv. Appl. Math.*, 2: 482–489 can be used.

Unless specifically stated otherwise, all % amino acid sequence identity values used herein are obtained by manual alignment. However, the ALIGN-2 sequence comparison computer program can be used as described in WO 00/15796.

The term "stringency" refers to the conditions (temperature, ionic strength, solvents, etc) under which hybridization between polynucleotides occurs. A hybridization reaction conducted under high stringency conditions is one that will only occur between polynucleotide molecules that have a high degree of complementary base pairing (about 85% to 100% of sequence identity). Conditions for high stringency hybridization, for example, may include an overnight incubation at about 42° C. for about 2.5 hours in 6×SSC/0.1% SDS, followed by washing of the filters in 1.0×SSC at 65° C., 0.1% SDS. A hybridization reaction conducted under moderate stringency conditions is one that will occur between polynucleotide molecules that have an intermediate degree of complementary base pairing (about 50% to 84% identity).

As used herein the term "variant" means a polynucleotide or polypeptide with a sequence that differs from a native polynucleotide or polypeptide. Variants can include changes that result in amino acid substitutions, additions, and deletions in the resulting variant polypeptide when compared to a full length native sequence or a mature polypeptide sequence.

The term "vector," "extra-chromosomal vector" or "expression vector" refers to a first piece of DNA, usually double-stranded, which may have inserted into it a second piece of DNA, for example a piece of heterologous DNA like the cDNA of cynomolgus FcγRI. Heterologous DNA is DNA that may or may not be naturally found in the host cell and includes additional copies of nucleic acid sequences naturally present in the host genome. The vector transports the heterologous DNA into a suitable host cell. Once in the host cell the vector may be capable of integrating into the host cell chromosomes. The vector may also contain the necessary elements to select cells containing the integrated DNA as well as elements to promote transcription of mRNA from the transfected DNA. Examples of vectors within the scope of the present invention include, but are not limited to, plasmids, bacteriophages, cosmids, retroviruses, and artificial chromosomes.

Modes of Carrying Out the Invention

The invention is based upon, among other things, the isolation and sequencing of nucleic acids encoding Fc receptor polypeptides from non-human primates, such as cynomolgus monkeys and chimps. In particular, the invention provides isolated polynucleotides encoding FcR polypeptides with an amino acid sequence of SEQ ID NO: 9, 11, 15, 17, 18, 20, 29, 64 or fragments thereof. The invention also provides isolated polynucleotides encoding mature FcR polypeptides with an amino acid sequence of SEQ ID NO: 65, 66, 67, 68, 69, 71 or 72, or fragments thereof. The invention also provides an isolated polynucleotide encoding β-2 microglobulin having an amino acid sequence of SEQ ID NO: 25 or SEQ ID NO: 70.

The cynomolgus monkey or chimp Fc receptor polynucleotides and polypeptides of the invention are useful for evaluation of binding of antibodies of any subclass (especially antibodies with prospective therapeutic utility) to cynomolgus or chimpanzee FcR polypeptides prior to in vivo evaluation in a primate. Evaluation could include testing binding to primate FcRs or Fc receptor polypeptides in an ELISA-format assay or to transiently- or stably-transfected human or primate cells (e.g. CHO, COS). Evaluation of the ability of a human antibody to bind to cynomolgus or other primate FcRs or Fc receptor polypeptides (either in an ELISA- or transfected cell format) could be used as a preliminary test prior to evaluation of pharmacokinetics/pharmacodynamics in vivo. Binding of antibodies or antibody variants to cynomolgus FcRn or FcRn polypeptides would be useful to identify antibodies or antibody variants that could have a longer half life in vivo. Binding of antibodies to FcRn correlates with a longer half life in vivo.

The primate FcRs or Fc receptor polypeptides could also be used to screen for variants (e.g. protein-sequence or carbohydrate) of primate or human IgG which exhibit either improved or reduced binding to these receptors or receptor polypeptides; such variants could then be evaluated in vivo in a primate model for altered efficacy of the antibody, e.g. augmentation or abrogation of IgG effector functions. In addition, soluble cynomolgus or chimpanzee Fc receptor polypeptides could be evaluated as therapeutics in primate models.

For example, in one aspect of the invention, a method is provided for identifying agents that selectively activate ITAM motifs in target Fc receptors while failing to activate ITIM motifs in other Fc receptors. Preferably these agents are antibodies and more preferably these agents are monoclonal antibodies. These identified agents may have uses in designing therapeutic antibodies which preferentially bind to and activate only ITAM-containing FcγR (i.e. not simultaneously engaging the inhibitory ITIM-containing receptors) which could thereby improve the cytotoxicity or phagocytosis ability of the therapeutic antibody or the ability of the therapeutic antibody to be internalized by antigen-presenting cells for increased immune system response against the target antigen.

Finally, the cynomolgus FcγR polynucleotides and polypeptides of the invention permit a more detailed analysis of FcγR-mediated molecular interactions. The amino acids in human IgG1 which interact with human FcγR have been mapped (Shields, R. L., Namenuk, A. K., Hong, K., Meng, Y. G., Rae, J., Briggs, J., Xie, D., Lai, J., Stadlen, A., Li, B., Fox, J. A., and Presta, L. G. (2001) J. Biol. Chem. 276, 6591–6604). Testing the binding of these same human IgG1 variants against cynomolgus FcγR can aid in mapping the interaction of specific amino acids in the human IgG1 with amino acids in the FcγR.

Within the application, unless otherwise stated, the techniques utilized may be found in any of several well-known references, such as: *Molecular Cloning: A Laboratory Manual* (Sambrook et al. (1989) Molecular cloning: A Laboratory Manual), *Gene Expression Technology* (Methods in Enzymology, Vol. 185, edited by D. Goeddel, 1991 Academic Press, San Diego, Calif.), "Guide to Protein Purification" in *Methods in Enzymology* (M. P. Deutshcer, 3d., (1990) Academic Press, Inc.), *PCR Protocols: A Guide to Methods and Applications* (Innis et al. (1990) Academic Press, San Diego, Calif.), Culture of Animal Cells: A Manual of Basic Technique, $2^{nd}$ ed. (R. I. Freshney (1987) Liss, Inc., New York, N.Y.), and *Gene Transfer and Expression Protocols*, pp 109–128, ed. E. J. Murray, The Humana Press Inc., Clifton, N.J.).

Polynucleotide Sequences

One aspect of the invention provides isolated nucleic acid molecules encoding Fc receptor polypeptides from cynomolgus monkeys and chimps. Due to the degeneracy of the genetic code, two DNA sequences may differ and yet encode identical amino acid sequences. The present invention thus provides isolated nucleic acid molecules comprising a polynucleotide sequence encoding cynomolgus FcR polypeptides, wherein the polynucleotide sequences encode a polypeptide with an amino acid sequence of SEQ ID NO: 9, or SEQ ID NO: 11, or SEQ ID NO: 15, or SEQ ID NO: 18, or SEQ ID NO: 20, or SEQ ID NO: 29, or SEQ ID NO: 64, or fragments thereof. The present invention also provides isolated nucleic acid molecules comprising a polynucleotide sequence encoding a chimp FcγR polypeptide of the invention, wherein the polynucleotide sequence encodes a polypeptide with an amino acid sequence of SEQ ID NO: 17 or fragments thereof. The invention also provides for isolated nucleic acid molecules comprising a polynucleotide sequence encoding cynomolgus β-2 microglobulin with an amino acid sequence of SEQ ID NO: 25.

The present invention also provides isolated nucleic acid molecules comprising a polynucleotide sequence encoding mature nonprimate FcR polypeptides, wherein the polynucleotide sequences encode a polypeptide with an amino acid sequence of SEQ ID NO: 65, 66, 68, 67, 69, 70, 71, or 72.

The nucleotide sequences shown in the tables, in most instances, begin at the coding sequence for the signal sequence of the Fc receptor polypeptide.

Nucleotide sequences of the non-human primate receptors have been aligned with human sequences for FcR polypeptides or β-2 microglobulin to determine % sequence identity. Nucleotide sequences of primate and human proteins are aligned manually and differences in nucleotide or protein sequence noted. Percent identity is calculated as number of identical residues/number of total residues. When the sequences differ in the total number of residues, two values for percent identity are provided, using the two different numbers for total residues. Some nucleic acid sequences for human FcR are known to those of skill in the art and are identified by GenBank accession numbers.

In one embodiment, the invention provides isolated nucleic acid molecules comprising a polynucleotide encoding a cynomolgus FcγRI α-chain. One example of a cynomolgus FcγRI α-chain has an amino acid sequence including the signal sequence as shown in Table 10 (SEQ. ID. NO: 9). The mature cynomolgus FcγRI α-chain has an amino acid sequence shown in Table 10 (SEQ ID NO: 65). An example of an isolated nucleic acid encoding a cynomolgus FcγRI α-chain is shown in Table 3 (SEQ ID NO: 1). A nucleic acid sequence encoding a cynomolgus FcγRI α-chain has about 91% or 96% sequence identity when aligned with a human nucleic acid sequence (SEQ ID NO: 2) encoding a FcγRI α-chain as shown in Table 3 (GenBank Accession No. L03418).

In another embodiment, the invention provides an isolated nucleic acid comprising a polynucleotide sequence encoding a cynomolgus gamma chain of FcγRI/III. An example of such a nucleic acid sequence is shown in Table 4 (SEQ ID NO: 13). An example of a cynomolgus gamma chain polypeptide is shown in Table 12 (SEQ ID NO: 11). A nucleic acid encoding a cynomolgus gamma chain has about 99% sequence identity when aligned with a human nucleic acid sequence (SEQ ID NO: 14) encoding a FcR gamma chain as shown in Table 4 (GenBank Accession No. M33195).

In another embodiment, the invention provides isolated nucleic acid molecules comprising a polynucleotide encoding a cynomolgus FcγRIIA. One example of cynomolgus FcγRIIA has an amino acid sequence including the signal sequence as shown in Table 11 (SEQ. ID. NO: 15). The mature cynomolgus FcγRIIA has an amino acid sequence as shown in Table 21 (SEQ ID NO: 66). An example of an isolated nucleic acid encoding a cynomolgus FcγRIIA is shown in Table 5 (SEQ ID NO: 3). A nucleic acid sequence encoding a cynomolgus FcγRIIA α-chain has about 94% sequence identity when aligned with a human nucleic acid sequence (SEQ ID NO: 4) encoding a FcγRIIA as shown in Table 5 (Genbank Accession No. M28697).

The invention also provides for isolated nucleic acids comprising a polynucleotide encoding FcγR from chimps such as an isolated nucleic acid comprising a polynucleotide encoding a FcγRIIA receptor. One example of a chimp FcγRIIA has an amino acid sequence including the signal sequence as shown in Table 11 (SEQ. ID. NO: 17). The mature chimp FcγRIIA has an amino acid sequence as shown in Table 11 (SEQ ID NO: 67). An example of an isolated nucleic acid encoding a chimp FcγRIIA is shown in Table 5 (SEQ ID NO: 22). A nucleic acid sequence having a sequence of SEQ ID NO: 22 has about 99% sequence identity when aligned with a human nucleic acid sequence (SEQ ID NO: 4) encoding a FcγRIIA as shown in Table 5 (GenBank Accession No. M28697).

In another embodiment, the invention provides isolated nucleic acid molecules comprising a polynucleotide encoding a cynomolgus FcγRIIB. One example of a cynomolgus FcγRIIB has an amino acid sequence as shown in Table 11 (SEQ. ID. NO: 18). The mature cynomolgus FcγRIIB has an amino acid sequence as shown in Table 22 (SEQ ID NO: 68). An example of an isolated nucleic acid encoding a cynomolgus FcγRIIB is shown in Table 6 (SEQ ID NO: 5). A nucleic acid sequence encoding a cynomolgus FcγRIIB has about 94% sequence identity when aligned with a human nucleic acid sequence (SEQ ID NO: 6) encoding a FcγRIIB as shown in Table 6 (GenBank Accession No.X52473).

In another embodiment, the invention provides isolated nucleic acid molecules comprising a polynucleotide encoding a cynomolgus FcγRIIIA α-chain. One example of a cynomolgus FcγRIIIA has an amino acid sequence as shown in Table 11 (SEQ. ID. NO: 20). The mature cynomolgus FcγRIIIA has an amino acid sequence as shown in Table 23 (SEQ ID NO: 69). An example of an isolated nucleic acid encoding a cynomolgus FcγRIIIA α-chain is shown in Table 7 (SEQ ID NO: 7). A nucleic acid sequence cynomolgus FcγRIIIA α-chain has about 96% sequence identity when aligned with a human nucleic acid sequence (SEQ ID NO: 8) encoding a FcγRIIIA α-chain as shown in Table 7 (GenBank Accession No.X52645).

The invention also provides isolated nucleic acid molecules having a polynucleotide sequence encoding a cynomolgus Fc receptor (FcRn) α-chain. One example of a cynomolgus Fc receptor α-chain (S3) has an amino acid sequence of SEQ ID NO. 29 as shown in Table 14. An allele has been identified encoding a polypeptide with an amino acid sequence which differs from that of SEQ ID NO: 29 by a substitution of an asparagine for a serine at the third residue in the mature polypeptide. This polypeptide sequence has been designated SEQ ID NO: 64. The mature polypeptides of FcRn α-chain (S3) and FcRn α-chain (N3) have the amino acid sequences of SEQ ID NO: 71 and 72, respectivly. An example of an isolated nucleic acid encoding a cynomolgus FcRn α-chain is SEQ ID NO: 27 shown in Table 9. A nucleic acid encoding a cynomolgus FcRn has about 97% sequence identity when aligned with a human sequence (SEQ ID NO: 28) encoding a human FcRn α-chain as shown in Table 9 (GenBank Accession No. U12255).

In another embodiment, the invention provides isolated nucleic acid molecules comprising a polynucleotide sequence encoding cynomolgus β-2 microglobulin. One example of a cynomolgus β-2 microglobulin has an amino acid sequence as shown in Table 13 (SEQ ID NO: 25). The mature β-2 microglobulin has a sequence as shown in Table 13 (SEQ ID NO: 70). An example of an isolated nucleic acid encoding a cynomolgus β-2 microglobulin is shown in Table 8 (SEQ ID NO: 23). A nucleic acid cynomolgus β-2 microglobulin has about 95% sequence identity when aligned with a human sequence (SEQ ID NO: 24) encoding β-2 microglobulin as shown in Table 8 (GenBank Accession No. AB021288).

The non-human primate nucleic acids of the invention include cDNA, chemically synthesized DNA, DNA isolated by PCR, and combinations thereof. RNA transcribed from cynomolgus or chimp cDNA is also encompassed by the invention. The cynomolgus DNA can be obtained using standard methods from tissues such as the spleen or liver and as described in the Examples below. The chimp FcγR DNA can be obtained using standard methods from tissues such as spleen or liver and as described in the Examples below.

In another aspect of the invention, a method of obtaining a nucleic acid encoding a nonhuman primate Fc receptor is provided. The method comprises amplifying a nucleic acid from a nonhuman primate cell with a primer set comprising a forward and a reverse primer, wherein the primer sets are selected from the group consisting of SEQ ID NO:31 and SEQ ID NO:32, SEQ ID NO:33 and SEQ ID NO:34, SEQ ID NO:35 and SEQ ID NO:36, SEQ ID NO:37 and SEQ ID NO:38, SEQ ID NO:39 and SEQ ID NO:40, SEQ ID NO:41 and SEQ ID NO:42, SEQ ID NO:43 and SEQ ID NO:44, SEQ ID NO:45 and SEQ ID NO:46, SEQ ID NO:47 and SEQ ID NO:48, SEQ ID NO:49 and SEQ ID NO:50, SEQ ID NO:51 and SEQ ID NO:52, and SEQ ID NO:53 and SEQ ID NO:54; and isolating the amplified nucleic acid. The nonhuman primate cell is a preferably a cynomologus spleen cell or a chimp spleen cell. Some of the primer sets provide for amplification of an extracellular fragment of the Fc receptor polypeptides fused to GlyHis-GST.

Fragments of the cynomolgus and chimp FcγR-encoding nucleic acid molecules described herein, as well as polynucleotides capable of hybridizing to such nucleic acid molecules, may be used in a number of ways including as a probe or as primers in a polymerase chain reaction (PCR). Such probes may be used, e.g., to detect the presence of FcγR polynucleotides in in vitro assays, as well as in Southern and Northern blots. Cell types expressing the FcγR may also be identified by the use of such probes. Such procedures are well known, and the skilled artisan will be able to choose a probe of a length suitable to the particular application. For PCR, 5' and 3' primers corresponding to the termini of the nucleic acid molecules are employed to isolate and amplify that sequence using conventional techniques. Fragments useful as probes are typically oligonucleotides about 18 to 20 nucleotides, including up to the full length of the polynucleotides encoding the FcγR. Fragments useful as PCR primers typically are oligonucleotides of 20 to 50 nucleotides.

Other useful fragments of the different cynomolgus FcγR polynucleotides are antisense or sense oligonucleotides comprising a single-stranded nucleic acid sequence capable of binding to a target FcγR mRNA (using a sense strand), or DNA (using an antisense strand) sequence.

Other useful fragments include polynucleotides that encode domains of a Fcγ receptor polypeptide. The fragments are preferably capable of binding to a Fc region containing molecule. One embodiment of a polynucleotide fragment is a fragment that encodes extracellular domains of a Fcγ receptor polypeptide in which the transmembrane and cytoplasmic domains have been deleted. Other domains of Fcγ receptors are identified in, for example, Table 10 and Table 11. Nucleic acid fragments encoding one or more polypeptide domains are included within the scope of the invention.

The invention also provides variant cynomolgus and chimp FcγR nucleic acid molecules as well as variant cynomolgus β-2 microglobulin nucleic acid molecules. Variant polynucleotides can include changes to the nucleic acid sequence that result in amino acid substitutions, additions, and deletions in the resultant variant polypeptide when compared to a native polypeptide, for instance SEQ ID NOs: 9, 11, 15, 17, 18, 20, 25, 29, or 64. The changes to the variant nucleic acid sequences can include changes to the nucleic acid sequence that result in replacement of an amino acid by a residue having similar physiochemical properties, such as substituting one aliphatic residue (Ile, Val, Leu, or Ala) for another, or substitutions between basic residues Lys and Arg, acidic residues Glu and Asp, amide residues Gln and Asn, hydroxyl residues Ser and Tyr, or aromatic residues Phe and Tyr. Variant polynucleotide sequences of the present invention are preferably at least about 95% identical, more preferably at least about 96% identical, more preferably at least about 97% or 98% identical, and most preferably at least about 99% identical, to a nucleic acid sequence encoding the full length native sequence, a polypeptide lacking a signal sequence, an extracellular domain of the polypeptide, or a nucleic acid encoding a fragment of the Fcγ receptor polypeptide or β-2 microglobulin of sequences of SEQ ID NOs: 1, 3, 5, 7, 23 or 27.

The percentage of sequence identity between the sequences and a variant sequence as discussed above may also be determined, for example, by comparing the variant sequence with a reference sequence using any of the computer programs commonly employed for this purpose, such as ALIGN 2 or by using manual alignment. Percent identity is calculated as [number of identical residues]/[number of total residues]. When the sequences differed in the total number of residues, two values for percent identity are provided, using the two different numbers for total residues.

Alterations of the cynomolgus monkey and chimp FcγR polypeptides, and cynomolgus monkey β-2 microglobulin, nucleic acid and amino acid sequences may be accomplished by any of a number of known techniques. For example, mutations may be introduced at particular locations by procedures well known to the skilled artisan, such as oligonucleotide-directed mutagenesis, which is described by Walder et al., 1986, *Gene*, 42:133; Bauer et al., 1985, *Gene* 37:73; Craik, 1985, *BioTechniques*, 12–19; Smith et al., 1981, *Genetic Engineering: Principles and Methods*, Plenum Press; and U.S. Pat. Nos. 4,518,584 and 4,737,462.

The invention also provides cynomolgus and chimp FcγR polypeptides, cynomolgus FcRn polypeptide, β-2 microglobulin nucleic acid molecules, or fragments and variants thereof, ligated to heterologous polynucleotides to encode fusion proteins. The heterologous polynucleotides can be ligated to the 3' or 5' end of the nucleic acid molecules of the invention, for example SEQ ID NOs: 1, 3, 5, 7, 13, 22, 25 or 27, to avoid interfering with the in-frame expression of the resultant cynomolgus and chimp FcγR, cynomolgus FcRn, and β-2 microglobulin polypeptides. Alternatively, the heterologous polynucleotide can be ligated within the coding region of the nucleic acid molecule of the invention. Heterologous polynucleotides can encode a single amino acid, peptide, or polypeptides that provide for secretion, improved stability, or facilitate purification of the cynomolgus and chimp encoded polypeptides of the invention.

A preferred embodiment is a nucleic acid sequence encoding an extracellular domain of the α-chain of FcγRI, FcγIII or FcRn fused to Gly(His)$_6$-gst tag or FcγRIIA or IIB fused to Gly(His)$_6$-gst tag obtained as described in Example 1. The Gly(His)$_6$-gst tag provides for ease of purification of polypeptides encoded by the nucleic acid.

The cynomolgus and chimp FcγR polypeptide and β-2 microglobulin nucleic acid molecules of the invention can be cloned into prokaryotic or eukaryotic host cells to express the resultant polypeptides of the invention. Any recombinant DNA or RNA method can be use to create the host cell that expresses the target polypeptides of the invention, including, but not limited to, transfection, transformation or transduction. Methods and vectors for genetically engineering host cells with the polynucleotides of the present invention, including fragments and variants thereof, are well known in the art, and can be found in Current Protocols in Molecular Biology, Ausubel et al., eds. (Wiley & Sons, New York, 1988, and updates). Vectors and host cells for use with the present invention are described in the Examples provided herein.

The invention also provides isolated nucleic acids comprising a polynucleotide encoding the mature Fc receptor polypeptide. The isolated nucleic acids can further comprise a nucleic acid sequence encoding a heterologous signal sequence. A heterologous signal sequence is one obtained from a polynucleotide encoding a polypeptide different than the native sequence non-human primate Fc receptor polypeptides of the invention. Heterologous signal sequences include signal sequences from human Fc receptor polypeptides as well as from polypeptides like tissue plasminogen activator.

Polypeptide Sequences

Another aspect of the invention is directed to FcR polypeptides from non-human primates such as cynomolgus monkeys and chimps. The FcγR polypeptides include FcγRI α-chain, FcγRIIA, FcγRIIB, FcγRIIIA α-chain, FcRn α-chain, FcRγI/III γ-chain, and β-2 microglobulin. The polypeptides bind IgG antibody or other molecules having a Fc region. Some of the receptors are low affinity receptors which preferably bind to IgG antibody complexes. FcR polypeptides also mediate effector cell functions such as antibody dependent cellular cytotoxicity, induction of mediator release from the cell, uptake and destruction of antibody coated particles, and transport of immunoglobulins.

Amino acid sequences of the FcγR polypeptides derived from cynomolgus monkeys and chimps are aligned with the amino acid sequences encoding human FcγR polypeptides to determine the % of sequence identity with the human sequences. Amino acid sequences of primate and human proteins are aligned manually and differences in nucleotide or protein sequence noted. Percent identity is calculated as number of identical residues/number of total residues. When the sequences differ in the total number of residues, two values for percent identity are provided, using the two different numbers for total residues. Some amino acid sequences encoding human FcγR polypeptides are known to those skill in the art and are identified by GenBank Accession numbers.

The polypeptide sequences shown in the tables are numbered starting from the signal sequence or from the first amino acid of the mature protein. When the amino acid residues of the polypeptide are numbered starting from the signal sequence the numbers are identified by the number of the residue and a line. When the amino acid residues of the polypeptide are also numbered from the first amino acid of the mature human protein, the amino acid is designated by the number and Δ symbol. In Table 11, the first N terminal residue of the cynomologus sequences is designated with an asterisk, but the numbering is still that corresponding to the mature human protein. The numbering of the amino acid residues of the FcR polypeptides is sequential.

The non-human primate receptors were also analyzed to compare the binding of the non-human primate Fc receptor polypeptides to various subclasses of human IgG and IgG variants to human Fc receptors. The binding to the subclasses also included binding to IgG4b. IgG4b is a form of IgG4, but has a change in the hinge region at amino acid residue 228 from serine to a proline. This change results in a molecule that is more stable than the native IgG4 due to increase formation of interchain disulfide bonds as described in Angal, S., King, D. J., Bodmer, M. W., Turner, A., Lawson, D. G., Robert, G., Pedley B. and Adair, J. R. (1993) A single amino acid substitution abolishes heterogeneity of chimeric—mouse/human (IgG4) antibody. *Molec. Immunology* 30:105–108.

One embodiment of the invention is a cynomolgus FcγRI polypeptide. A cynomolgus FcγRI binds to IgG and other molecules having an Fc region, preferably human monomeric IgG. One example of an α-chain of a cynomolgus FcγRI is a polypeptide having a sequence of SEQ ID NO: 9. Based on the alignment with the human sequence, the mature cynomolgus FcγRI has a sequence of SEQ ID NO: 65. An extracellular fragment obtained as described in example 1 has an amino acid sequence of Δ1 to Δ269 as shown in table 10.

An alignment of the amino acid sequence α-chain of the FcγRI from human and cynomolgus monkeys is also shown in Table 10. The amino acid numbers shown below the amino acids with the symbol Δ are numbered from the start of the mature polypeptide not including the signal sequence. The numbers above the amino acid residues represent the numbering of the residues starting at the signal sequence. Each of the domains of the FcγRI α-chain are shown including signal sequence, extracellular domain 1, extracellular domain 2, extracellular domain 3, and the transmembrane and intracellular sequence. The alignment of a human sequence of SEQ ID NO: 10 (GenBank Accession No. P12314) with a cynomolgus FcγRI α-chain sequence starting from the signal sequence shows about a 90% or 94% sequence identity with the human sequence depending on whether the 3' extension present on the human sequence was used in the calculation.

This alignment of the cynomolgus sequence with the human sequence shows that the cynomolgus FcγRI α-chain has the same number of amino acids in the signal sequence, the three extracellular domains, and transmembrane domain as found in the human FcγRI sequence (Table 10). In contrast, the cynomolgus FcγRI α-chain intracellular domain is shorter than that of the human FcγRI α-chain by seventeen amino acids (Table 10). A cynomolgus FcγRI α-chain binds to human monomeric subclasses as follows: IgG3≧IgG1>IgG4b>>>IgG2, which is similar to that of the human FcγRI.

Fc receptors of the I and IIIA subclass are complex molecules including an α-chain complexed to either a homo or hetero dimer of a γ-chain. The invention also includes a cynomolgus FcR gamma chain. One example of a gamma chain polypeptide has an amino acid sequence of SEQ ID NO: 11 as shown in Table 12. When the cynomolgus gamma chain amino acid sequence is aligned with a human sequence for the gamma chain of SEQ ID NO: 12 (GenBank Accession No. P30273) it has about 99% sequence identity with the human sequence. The ITAM motif of the cynomolgus gamma chain is identical to that of the human gamma chain.

Another embodiment of the invention is a cynomolgus FcγRIIA. A cynomolgus FcγRIIA binds to immunoglobulins and other molecules having an Fc region, preferably immunoglobulins complexed to an antigen or each other. More preferably, the receptor binds a dimeric or hexameric immune complex of human Ig. One example of a cynomolgus FcγRIIA has an amino acid sequence of SEQ ID NO: 15. The mature cynomolgus FcγRIIA has an amino acid sequence of SEQ ID NO: 66 (Table 21). an extracellular fragment obtained with the primers of example 1 has an amino acid sequence of Δ1 to Δ182 as shown in Table 21.

The cynomolgus FcγRIIA sequence was aligned with a human amino acid sequence of FcγRIIA as shown in Table 11 (SEQ ID NO: 16) (Accession No. P 12318). In table 11, the amino acid numbers shown below the amino acids with the symbol Δ are numbered from the start of the mature human polypeptide not including the signal sequence. The numbers above the amino acid residues represent the numbering of the residues starting at the signal sequence. When the cynomolgus sequence is aligned with the human sequence it has about 87% or 89% sequence identity with the human sequence depending on whether the alignment starts with the MAMETQ sequence. This alignment shows that the cynomolgus FcγRIIA has fewer amino acids in the signal peptide sequence than found in the human FcγRIIA (Table 11). Cynomolgus FcγRIIA has about the same number of amino acids in the two extracellular domains, transmembrane domain, and intracellular domain as found in the human FcγRIIA sequence (Table 11). Notably, the cynomolgus FcγRIIA contains the identical two ITAM motifs as found in the human receptor (Table 11).

The cynomolgus FcγRIIA binds to hexameric complexes of subclasses IgG with the following binding pattern: IgG3=IgG2>IgG1>IgG4b, IgG4. A human FcγRIIA isoform with an arginine at the amino acid corresponding to the amino acid 131 (R131) binds hexameric IgG subclasses as follows: IgG3>IgG1>>>IgG2≧IgG4. A human FcγRIIA isoform with a histidine at the amino acid corresponding to the amino acid 131 (H131) binds hexameric IgG subclasses as follows: IgG3≧IgG1=IgG2>>>IgG4. Cynomolgus FcγRIIA with an amino acid sequence of SEQ ID NO: 15 has H 131 and binds to human subclasses of IgG in a similar manner to those human Fc receptors with the H131 isoform variant. However, the cynomolgus Fc receptor binds IgG2 as efficiently as it binds IgG3.

Another embodiment of the invention is a chimp FcγRIIA. A chimp FcγRIIA binds to immunoglobulins and other molecules having an Fc region, preferably immunoglobulins complexed to an antigen or each other. Preferably the receptor binds a dimeric or hexameric immune complex of human Ig. One example of a chimp FcγRIIIA has an amino acid sequence of SEQ ID NO: 17. Based on the alignment with the human sequence, the mature chimp FcγRIIA has an amino acid sequence of SEQ ID NO: 67.

The chimp FcγRIIA amino acid sequence was aligned starting with the signal sequence with a human sequence for FcγRIIA of SEQ ID NO: 16 as shown in Table 11 (Accession No. P12318). The alignment shows that when compared to the human sequence, the chimp sequence has about 97% sequence identity. This alignment also shows that the chimpanzee FcγRIIA has one less amino acid in the signal peptide sequence than found in the human FcγRIIA α-chain (Table 11). Chimpanzee FcγRIIA has the same number of amino acids in the two extracellular domains, transmembrane domain, and intracellular domain as found in the human FcγRIIA sequence (Table 11). Notably, the chimpanzee FcγRIIA contains the identical two ITAM motifs as found in the human and cynomolgus receptors (Table 11).

Another embodiment of the invention is a cynomolgus FcγRIIB. A cynomolgus FcγRIIB binds to immunoglobulins and other molecules having an Fc region, preferably immunoglobulins complexed to an antigen or each other. More preferably, the receptor binds a dimeric or hexameric immune complex of human Ig. One example of a cynomolgus FcγRIIB has an amino acid sequence of SEQ ID NO: 18. The mature cynomolgus FcγRIIB has an amino acid sequence of SEQ ID NO: 68 (Table 22). an extracellular fragment obtained with the primers of example 1 has an amino acid sequence of Δ1 to Δ184 as ahown in table 22.

The cynomolgus FcγRIIB has about 92% sequence identity with a human amino acid sequence of FcγRIIB as shown in Table 11 (SEQ ID NO: 19) (Accession No. X52473). An alignment of the cynomolgus sequence with the human sequence shows that the cynomolgus FcγRIIB has about the same number of amino acids in the signal peptide, two extracellular domains, and transmembrane domain as found in the human FcγRIIB sequence (Table 11). The cynomolgus FcγRIIB has three amino acids inserted in the N-terminal portion of the intracellular domain (compared to human FcγRIIB) (Table 11). Notably, the cynomolgus FcγRIIB intracellular domain contains the identical ITIM motif as found in the human receptor (Table 11).

The cynomolgus FcγRIIB binds to hexameric complexes of subclasses IgG with the following binding pattern: IgG2≧IgG3>IgG1>IgG4b, IgG4. A human FcγRIIB binds hexameric IgG subclasses as follows: IgG3≧IgG1>IgG2>IgG4. The cynomolgus FcγRIIB binds IgG2 much more efficiently than the human FcγRIIB.

Another embodiment of the invention is a cynomolgus FcγRIIIA. A cynomolgus receptor FcγRIIIA binds to immunoglobulins and other molecules having an Fc region, preferably immunoglobulins complexed. Preferably, the receptor binds a dimeric or hexameric immune complex of human Ig. One example of an amino acid sequence of the α-chain of FcγRIIIA is SEQ ID NO: 20. The mature cynomolgus FcγRIIIA α-chain has a sequence of SEQ ID NO: 69 (Table 23). An extracellular fragment obtained using the primer as described in example 1 has an amino acid sequence of Δ1 to Δ187 as ahown in Table 23.

The cynomolgus FcγRIIIA α-chain sequence was aligned with a human amino acid sequence of FcγRIIIA as shown in Table 11 (SEQ ID NO: 21) (Accession No. P08637). In table 11, the amino acid numbers shown below the amino acids with the symbol Δ are numbered from the start of the mature human polypeptide not including the signal sequence. The numbers above the amino acid residues represent the numbering of the residues starting at the signal sequence. The alignment with the human and cynomolgus FcγRIIIA sequence shows the sequence has about 91% sequence identity to the human sequence. This alignment of the cynomolgus sequence with the human sequence shows that the cynomolgus FcγRIIIA α-chain has about the same number of amino acids in the signal peptide, the two extracellular domains, the transmembrane domain, and intracellular domain as found in the human FcγRIIIA sequence (Table 11). Neither the cynomolgus nor human intracellular domains contain an ITAM motif; the activating ITAM motif for human FcγRIIIA is supplied by the associated γ-chain and the same situation most likely occurs in cynomolgus monkeys.

The cynomolgus FcγRIIIA α-chain binds to hexameric complexes of subclasses IgG with the following binding pattern: IgG1>IgG3>>IgG2≧IgG4b, IgG4. A human FcγRIIIA isoform with a phenylalanine at the amino acid corresponding to the amino acid 158 (F158) binds hexameric IgG subclasses as follows: IgG3=IgG1>>>IgG2, IgG4. A human FcγRIIA isoform with a valine at the amino acid corresponding to the amino acid 158 (V158) binds hexameric IgG subclasses as follows: IgG1>IgG3>>>IgG2A, IgG4. Cynomolgus FcγRIIIA with an amino acid sequence of SEQ ID NO: 20 has an isoleucine at amino acid position corresponding to amino acid 158 and binds human Ig subclasses similar to human FcγRIIIA VI 158.

Human IgG1 binds to human FcγRIIIA-V158 better than it does to human FcγRIIIA-F158 (Koene, H. R., Kleijer, M., Algra, J., Roos, D., von dem Borne, E. G. K., and de Hass, M. (1997) Blood 90, 1109–1114; Wu, J., Edberg, J. C., Redecha, P. B., Bansal, V., Guyre, P. M., Coleman, K., Salmon, J. E., and Kimberly, R. P. (1997) J. Clin. Invest. 100, 1059–1070; Shields, R. L., Namenuk, A. K., Hong, K., Meng, Y. G., Rae, J., Briggs, J., Xie, D., Lai, J., Stadlen, A., Li, B., Fox, J. A., and Presta, L. G. (2001) J. Biol. Chem. 276, 6591–6604). In humans, the FcγRIIIA-F158 allele predominates with approximately 90% of humans having at least one FcγRIIIA-F158 allele (Lehrnbecher, T., Foster, C. B., Zhu, S., Leitman, S. F., Goldin, L. R., Huppi, K., and Chanock, S. J. (1999) Blood 94, 4220–4232). In addition, recent studies have begun to correlate specific disease states with the FcγRIIIA polymorphic status of individuals (Wu, J., Edberg, J. C., Redecha, P. B., Bansal, V., Guyre, P. M., Coleman, K., Salmon, J. E., and Kimberly, R. P. (1997) J. Clin. Invest. 100, 1059–1070; Lehrnbecher, T., Foster, C. B., Zhu, S., Venzon, D., Steinberg, S. M., Wyvill, K., Metcalf, J. A., Cohen, S. S., Kovacs, J., Yarchoan, R., Blauvelt, A., and Chanock, S. J. (2000) Blood 95, 2386–2390; Nieto, A., Caliz, R., Pascual, M., Mataran, L., Garcia, S., and Martin, J. (2000) Arthritis & Rheumatism 43, 735–739). Notably, the chimpanzee and cynomolgus FcγRIIIA have valine and isoleucine, respectively, at position 158. The similarity of binding of the four human subclasses of IgG to cynomolgus FcγRIIIA and human FcγRIIIA-V158 (as opposed to human FcγRIIIA-F158) suggests that evaluation of human antibodies in primate models should account for the primate model reflecting only aminority of humans with respect to binding to FcγRIIIA receptors, i.e. FcγRIIIA-V158/V158 homozygotes. For example, since human FcγRIIIA-V158 exhibits superior antibody-dependent cellular cytotoxicity (ADCC) compared to human FcγRIIIA-F158 (Shields, R. L., Namenuk, A. K., Hong, K., Meng, Y. G., Rae, J., Briggs, J., Xie, D., Lai, J., Stadlen, A., Li, B., Fox, J. A., and Presta, L. G. (2001) J. Biol. Chem. 276, 6591–6604), primate models may overestimate the efficacy of human antibody effector functions associated with FcγRIIIA.

However, the binding patterns of human IgG subclasses to other cynomolgus FcRs, especially FcγRI, indicate that the non-human primates can be used as effective models to evaluate the safety, efficacy and pharmokenetics of Fc region binding molecules.

The invention also provides for Fc receptor polypeptides identified as FcRn. Amino acid sequences of cynomolgus FcRn are shown in Table 14. In Table 14, the numbers shown below the amino acids and designated with the signal Δ are numbered from the start of the mature polypeptide. Two alleles were identified and are shown in Table 14. A cynomologus FcRn α-chain has an amino acid sequence of SEQ ID NO: 29 with a serine at residue 3 of the mature polypeptide. A cynomolgus FcRn α-chain has a sequence of SEQ ID NO: 64 and has an asparagine at residue 3 of the mature polypeptide. The mature polypeptides of FcRn α-chain S3 and FcRn α-chain N3 have a sequence of SEQ ID NO: 71 and 72, respectively. A extracellular fragment of a FcRn as obtained using the primers as described in example 1 has an amino acid sequence of Δ1 to Δ274 as shown in table 14.

A sequence alignment of cynomolgus FcRn α-chain sequences to human FcRn α-chain (SEQ ID NO: 20) (GenBank Accession No. U12255) shows that the cynomolgus sequence is about 97% identical to the human sequence. Cynomolgus FcRn (S3) and FcRn (N3) α-chains bind to subclasses of IgG with the following binding pattern: IgG3>>IgG4>IgG2>IgG1, which is similar to that of the human FcRn α-chain.

The invention also includes cynomolgus β-2 microglobulin polypeptides. A cynomolgus β-2 microglobulin polypeptide has a sequence of SEQ ID NO: 25, Table 13. The mature β-2 microglobulin polypeptide has a sequence of SEQ ID NO: 70. When the cynomolgus β-2 microglobulin sequence is aligned with a human sequence for β-2 microglobulin (SEQ ID NO: 26; GenBank Accession No. P01884), it shows that the cynomolgus sequence has about 92% sequence identity to human β-2 microglobulin.

Variants, derivatives, fusion proteins, and fragments of the different cynomolgus and chimp FcγR polypeptides that retain any of the biological activities of the FcRs, are also within the scope of the present invention. Note that one of ordinary skill in the art will readily be able to determine whether a variant, derivative, or fragment of a FcγR polypeptide displays activity by subjecting the variant, derivative, or fragment to a immunoglobulin binding assay as described below in Example 3.

Derivatives of the different cynomolgus and chimp FcγRs can be polypeptides modified by forming covalent or aggregative conjugates with other chemical moieties, such as glycosyl groups, polyethylene glycol (PEG) groups, lipids, phosphate, acetyl groups and the like.

In another embodiment, the polypeptides of the invention include fragments of the polypeptides that lack a portion or all of the transmembrane and intracellular domains: e.g. amino acid residues of the mature polypeptide as follows: FcγRI α-chain amino acid residues 270–336 of SEQ ID NO: 65; FcγRIIA amino acid residues 183 to 282 of SEQ ID NO: 66; chimp FcγRIIA amino acid residues 172 to 281 of SEQ ID NO: 67; FcγRIIB amino acid residues 185 to 252 of SEQ ID NO: 68, FcγRIIIA α-chain amino acid residues 188 to 234 of SEQ ID NO: 69; or FcRn amino acid residues 275 to 342 of SEQ ID NO: 71 or SEQ ID NO: 72. A soluble FcγR polypeptide may include a portion of the transmembrane domain and intracellular, as long as the polypeptide is secreted from the cell in which it is produced. Preferably, the fragments are capable of binding to an Fc region containing molecule.

Fragments of polypeptides also include one or more domain of the polypeptide identified in Table 10 or Table 11, including signal peptide, domain 1, domain 2, domain 3, transmembrane/intracellular, or a cytoplasmic domain including the ITAM or ITIM motif. Exemplary fragments of the polypeptides also include soluble polypeptides having only domain 1, domain 2 and domain 3 amino acid sequences of the corresponding mature FcγR polypeptides: e.g., amino acid residues Δ1 to Δ269 of cynomolgus FcγRI (Table 10), amino acid residues Δ1 to Δ182 of cynomolgus FcγRIIA (Table 21), amino acid residues Δ1 to Δ184 of cynomolgus FcγRIIB (Table 22), amino acid residues Δ1 to Δ187 of cynomolgus FcγRIIIA (Table 23), and amino acids Δ1 to Δ274 of cynomolgus FcRn (Table 14).

Cynomolgus or chimp FcγR variants within the scope of the invention may comprise conservatively substituted sequences, meaning that one or more amino acid residues of each polypeptide may be replaced by different residues that do not alter the secondary and/or tertiary structure of the polypeptide. Such substitutions may include the replacement of an amino acid by a residue having similar physicochemical properties, such as substituting one aliphatic residue (Ile, Val, Leu or Ala) for another, or substitution between basic residues Lys and Arg, acidic residues Glu and Asp, amide residues Gln and Asn, hydroxyl residues Ser and Tyr, or aromatic residues Phe and Tyr. Further information regarding making phenotypically silent amino acid exchanges may be found in Bowie et al., Science 247:1306–1310 (1990). Other variants which might retain substantially the biological activities of the proteins are those where amino acid substitutions have been made in areas outside functional regions of the protein.

The invention also provides variant cynomolgus and chimp FcR polypeptides. Variant polypeptide can include changes to the polypeptide sequence that result in the amino acid substitutions, additions, and deletions in the resultant variant polypeptide when compared to the native polypeptide, for instance SEQ ID NOs: 9, 15, 17, 18, 20, 25, 29, or 64. The changes to the variant polypeptide sequences can include changes to the nucleic acid sequence that result in replacement of an amino acid by a residue having similar physiochemical properties, such as substituting one aliphatic residue (Ile, Val, Leu, or Ala) for another, or substitutions between basic residues Lys and Arg, acidic residues Glu and Asp, amide residues Gln and Asn, hydroxyl residues Ser and Tyr, or aromatic residues Phe and Tyr. Variant polypeptide sequences of the present invention are preferably at least about 90% identical, more preferably at least about 91% identical, more preferably at least 92% or 93% identical, more preferably 94% identical, more preferably 95% or 96% identical, more preferably 97% or 98% identical, and most preferably at least about 99% identical, to a full length native sequence, a polypeptide lacking a signal sequence, an extracellular domain of the polypeptide, or a fragment of the Fcγ receptor or β-2 microglobulin of sequences of SEQ ID NOs: 9, 15, 17, 18, 20, 25, 29, or 64.

Another embodiment of the present invention are polypeptides of the invention fused to heterologous amino acids, peptides, or polypeptides. Such amino acids, peptides, or polypeptides, preferably facilitate purification of the polypeptide. Many of the available peptides used for such a function allow selective binding of the fusion protein to a binding partner. For example, the cynomolgus FcγRI polypeptide, having a sequence as shown in SEQ ID NO:9, may be modified to comprise a peptide to form a fusion protein which specifically binds to a binding partner, or peptide tag. Non-limiting examples of such peptide tags include the 6-His tag, Gly/His6/GST tag, thioredoxin tag, hemaglutinin tag, Glylh156 tag, and OmpA signal sequence tag. Full length, variable and truncated polypeptides of the present invention may be fused to such heterologous amino acids, peptides, or polypeptides. For example, the transmembrane and intracellular domains of cynomolgus FcγRIA can be replaced by DNA encoding the Gly/His$_6$/GST tag fused as His271. As will be understood by one of skill in the art, the binding partner which recognizes and binds to the peptide may be any molecule or compound including metal ions (e.g., metal affinity columns), antibodies, or fragments thereof, and any protein or peptide which binds the peptide, such as the FLAG tag. The polypeptides of the present invention can also be fused to the immunoglobulin constant domain of an antibody to form immunoadhesin molecules.

The polypeptides of the present invention are preferably provided in an isolated form, and preferably are purified. The polypeptides may be recovered and purified from recombinant cell cultures by well-known methods, including ammonium sulfate or ethanol precipitation, anion or cation exchange chromatography, phosphocellulose chromatography, hydrophobic interaction chromatography, affinity chromatography, hydroxylapatite chromatography and lectin chromatography. In a preferred embodiment, high performance liquid chromatography (HPLC) is employed for purification.

Vectors and Host Cells

The present invention also relates to vectors comprising the polynucleotide molecules of the invention, as well as host cell transformed with such vectors. Any of the polynucleotide molecules of the invention may be joined to a vector, which generally includes a selectable marker and an origin of replication, for propagation in a host. Host cells are genetically engineered to express the polypeptides of the present invention. The vectors include DNA encoding any of the polypeptides described above or below, operably linked to suitable transcriptional or translational regulatory sequences, such as those derived from a mammalian, microbial, viral, or insect gene. Examples of regulatory sequences include transcriptional promoters, operators, or enhancers, mRNA ribosomal binding sites, and appropriate sequences which control transcription and translation. Nucleotide sequences are operably linked when the regulatory sequence functionally relates to the DNA encoding the target protein. Thus, a promoter nucleotide sequence is operably linked to a cynomolgus monkey or chimp FcγR DNA sequence, FcRn α-chain DNA sequence, or β-2 microglobulin DNA sequence if the promoter nucleotide sequence directs the transcription of the FcγR sequence.

Expression of non-human primate receptors of the invention can also be accomplished by removing the native nucleic acid encoding the signal sequence or replacing the native nucleic acid signal sequence with a heterologous signal sequence. Heterologous signal sequences include those from human Fc receptor polypeptides or other polypeptides, such as tissue plasminogen activator. Nucleic acids encoding signal sequences from heterologous sources are known to those of skill in the art.

Selection of suitable vectors to be used for the cloning of polynucleotide molecules encoding the target polypeptides of this invention will depend upon the host cell in which the vector will be transformed, and, where applicable, the host cell from which the target polypeptide is to be expressed. Suitable host cells for expression of the polypeptides of the invention include prokaryotes, yeast, and higher eukaryotic cells, each of which is discussed below.

Expression of functional cynomolgus monkey or chimp FcγR polypeptides of the invention may require the genetic engineering of a host cell to contemporaneously express two or more polypeptide molecules. As was discussed previously, most FcγRs are complex molecules requiring the expression of both a IgG binding and a signal transducing polypeptide chain. The complex of two or more polypeptide chains forms the functional receptor. As such, for example, a host cell may be co-transfected with a first vector expressing the FcγRI α-chain, having a first selection marker, and a second vector expressing the FcγRI γ-chain, having a second selection marker. Only host cells that have acquired both vectors and are expressing both polypeptides would survive and express functional FcγRI. Other methods are envisioned for the co-transfection of multiple polypeptide chains into target host cells, including the linked expression of target polypeptides from the same vector.

The cynomolgus monkey or chimp FcγR, FcRn, or β-2 microglobulin polypeptides to be expressed in such host cells may also be fusion proteins which include regions from heterologous proteins. Such regions may be included to allow, e.g., secretion, improved stability, or facilitated purification of the polypeptide. For example, a sequence encoding an appropriate signal peptide can be incorporated into expression vectors. A DNA sequence for a signal peptide (secretory leader) may be fused in-frame to the target sequence so that target protein is translated as a fusion protein comprising the signal peptide. The DNA sequence for a signal peptide can replace the native nucleic acid encoding a signal peptide or in addition to the nucleic acid sequence encoding the native sequence signal peptide. A signal peptide that is functional in the intended host cell promotes extracellular secretion of the polypeptide. Preferably, the signal sequence will be cleaved from the target polypeptide upon secretion from the cell. Non-limiting examples of signal sequences that can be used in practicing the invention include the yeast I-factor and the honeybee melatin leader in Sf9 insect cells.

Suitable host cells for expression of target polypeptides of the invention include prokaryotes, yeast, and higher eukaryotic cells. Suitable prokaryotic hosts to be used for the expression of these polypeptides include bacteria of the genera Escherichia, Bacillus, and Salmonella, as well as members of the genera Pseudomonas, Streptomyces, and Staphylococcus. For expression in, e.g., *E. coli*, a target polypeptide may include an N-terminal methionine residue to facilitate expression of the recombinant polypeptide in a prokaryotic host. The N-terminal Met may optionally then be cleaved from the expressed polypeptide.

Expression vectors for use in prokaryotic hosts generally comprise one or more phenotypic selectable marker genes. Such genes generally encode, e.g., a protein that confers antibiotic resistance or that supplies an auxotrophic requirement. A wide variety of such vectors are readily available from commercial sources. Examples include pSPORT vectors, pGEM vectors (Promega), pPROEX vectors (LTI, Bethesda, Md.), Bluescript vectors (Stratagene), and pQE vectors (Qiagen).

The cynomolgus monkey or chimp FcγR, FcRn, or β-2 microglobulin, may also be expressed in yeast host cells from genera including Saccharomyces, Pichia, and Kluveromyces. Preferred yeast hosts are *S. cerevisiae* and *P. pas-*

*toris*. Yeast vectors will often contain an origin of replication sequence from a 2T yeast plasmid, an autonomously replicating sequence (ARS), a promoter region, sequences for polyadenylation, sequences for transcription termination, and a selectable marker gene. Vectors replicable in both yeast and *E. coli* (termed shuttle vectors) may also be used. In addition to the above-mentioned features of yeast vectors, a shuttle vector will also include sequences for replication and selection in *E. coli*. Direct secretion of the target polypeptides expressed in yeast hosts may be accomplished by the inclusion of nucleotide sequence encoding the yeast I-factor leader sequence at the 5' end of the cynomolgus FcγR-encoding nucleotide sequence.

Insect host cell culture systems may also be used for the expression of the polypeptides of the invention. In a preferred embodiment, the target polypeptides of the invention are expressed using a baculovirus expression system. Further information regarding the use of baculovirus systems for the expression of heterologous proteins in insect cells are reviewed by Luckow and Summers, *Bio/Technology* 6:47 (1988).

In another preferred embodiment, the cynomolgus FcγR polypeptides are individually expressed in mammalian host cells. Non-limiting examples of suitable mammalian cell lines include the COS-7 line of monkey kidney cells (Gluzman et al., *Cell* 23:175 (1981)), Chinese hamster ovary (CHO) cells (Puck et al., Proc. Natl. Acad. Sci. USA, 60:1275–1281 (1958), CV-1 and human cervical carcinoma cells (HELA) (ATCC CCL 2). Preferably, HEK293 cells are used for expression of the target proteins of this invention.

The choice of a suitable expression vector for expression of the target polypeptides of the invention will of course depend upon the specific mammalian host cell to be used, and is within the skill of the ordinary artisan. Examples of suitable expression vectors include pcDNA3.1/Hygro (Invitrogen), 409, and pSVL (Pharmacia Biotech). A preferred vector for expression of the cynomolgus FcγR polypeptides is pRK. Eaton, D. L., Wood, W. I., Eaton, D., Hass, P. E., Hollingshead, P., Wion, K., Mather, J., Lawn, R. M., Vehar, G. A., and Gorman, C. (1986) *Biochemistry* 25:8343–47. Expression vectors for use in mammalian host cells may include transcriptional and translational control sequences derived from viral genomes. Commonly used promoter sequences and enhancer sequences which may be used in the present invention include, but are not limited to, those derived from human cytomegalovirus (CMV), Adenovirus 2, Polyoma virus, and Simian virus 40 (SV40). Methods for the construction of mammalian expression vectors are disclosed, for example, in Okayama and Berg (*Mol. Cell. Biol.* 3:280 (1983)); Cosman et al. (*Mol. Immunol.* 23:935 (1986)) and Cosman et al (*Nature* 312:768 (1984)).

Method of Evaluating Biological Properties, Safety and Efficacy of Fc Region Containing Molecules One aspect of the invention includes a method for the evaluation of the pharmacokinetics/pharmacodynamics of FcR binding molecules such as humanized antibodies with cynomolgus monkey or chimp Fc receptors prior to an in vivo evaluation in a primate. This aspect of the invention is based on the finding that cynomolgus and chimp FcR polypeptides have a high degree of sequence identity with human Fc receptor polypeptides and bind to IgG subclasses in a similar manner. Evaluations can include testing, for example, humanized antibodies of any subclass (especially antibodies with prospective therapeutic utility) on target Fc receptors of the invention in an ELISA-format assay or to transiently expressing cells.

A method of the invention involves evaluating the binding of a Fc region containing polypeptide or agent to cynomolgus or chimp Fc receptor polypeptide by contacting the Fc region containing molecule with a cynomolgus or chimp Fc receptor polypeptide. The cynomolgus or chimp Fc receptor polypeptide can be soluble or can be expressed as a membrane bound protein on transiently infected cells. Binding of the Fc region containing molecule to the cynomolgus or chimp Fc receptor polypeptide indicates that the Fc region containing molecule or polypeptide is suitable for in vivo evaluation in a primate. Binding to cynomolgus FcRn molecules provides an indication that Fc region containing molecule or polypeptide will have a longer half-life in vivo.

The invention also provides for screening variants of Fc region containing molecules such as antibody variants for their biological properties, safety, efficacy and pharmcokenetics. Antibody variants are typically altered at one or more residues and then the variants are analyzed for alteration in biological activities including altered binding affinity for Fc receptors. Screening for alterations in biological activities by variants may be tested both in vivo and in vitro. For example, receptor polypeptides of the present invention can be used in an ELISA-format assay or transiently infected cells. Antibody variants which bind to cynomolgus and/or chimp FcR polypeptides, such as the α-chain of FcγRII, FcγRIII or FcRn or FcγRIIA or FcγRIIB, are variants that are suitable for in vivo evaluation in primates as a therapeutic agent.

Direct binding and binding affinity determination between the different Fc region containing molecules is preferably performed against soluble extracellular domains of cynomolgus FcγR polypeptides. For example, the transmembrane domain and intracellular domain of a target FcγR can be replaced by DNA encoding a Gly-His$_6$ tag or glutathione S-transferase (GST) (see Example 3). The Gly-His$_6$ tag or GST provide a convenient method for immobilizing the Fc binding region of the receptor to a solid support for identification and/or determination of binding affinities between the receptor and target antibody variant. Potential assays include ELISA-format assays, co-precipitation format assays, and column chromatographic format assays. Identified Fc region containing molecules should directly interact with the soluble cynomolgus FcγR and have equivalent or greater binding affinities for the cynomolgus FcγR, as compared to corresponding human FcγR.

Another aspect of the invention provides methods of identifying agents that have altered binding to a cynomolgus FcγR comprising an ITAM and/or ITIM region. A method of the invention involves identifying an agent that has increased binding affinity for an FcR comprising an ITAM region and a decreased affinity for a FcR comprising an ITIM region.

Target agents include molecules that have a Fc region, preferably an antibody and more preferably an IgG antibody. If the target agent is an antibody it may be a variant antibody with an altered amino acids sequence compared to the native sequence of the antibody. Preferably variant antibodies have had amino acid substitutions in regions of the antibody that are involved in binding to Fcγ receptor, including amino acids corresponding to amino acids 226 to 436 in a human IgG. Variant antibodies can be prepared using standard methods such as site specific oligonucleotide or PCR mediated methods as described previously. Examples of variant antibodies includes alanine variants of human IgG1, anti IgE E27 prepared as described in Shields et al., *J. Biol. Chem.* 276:6591 (2001).

Binding affinities of antibodies and/or variant antibodies are determined using standard methods as described in Shields et al., *J. Biol. Chem.* 276:6591 (2001) and in Examples 3–7 below. Binding affinities are preferably determined by binding to cells that express a Fcγ receptor of the type being analyzed. However, binding affinities of antibodies or Fc region containing molecules can also be determined using soluble Fcγ receptors or Fcγ receptors expressed on or secreted from a host cell.

A variant antibody that has an increased affinity for a cynomolgus FcγRIIA compared with a human FcγRIIA is an antibody that has a change in amino acid sequence at the position corresponding to amino acid 298 of human IgG1. One such variant has a change at that position from serine to alanine and is designated as S298A. Another variant antibody with a change at that position is designated as S298A/E333A/K334 which is a variant antibody with alanine in positions corresponding to amino acid 298, 333 and 334 of native sequence IgG1. These variants have increased binding affinity to a cynomolgus FcγRIIA compared to a human FcγRIIA.

In another method of the invention, target agents with altered binding affinity to a cynomolgus FcγRIIB as compared to human FcγRIIB are identified. The agents are preferably variants of native sequence antibodies. Binding affinities are determined as described above and as shown in the Examples below. Agents with enhanced binding to a FcγRIIB may preferentially stimulate ITIM inhibitory functions. Agents with decreased affinity for a cynomolgus FcγRIIB may have decreased stimulation of inhibitory function.

Variant antibodies that have decreased affinity for a cynomolgus FcγRIIB compared to a human FcγRIIB are: R255A, E258A, S37A, D280A and R301M.

Another embodiment of the invention involves the use of variant antibodies S298A or S298A/E333A/K334 to identify agents that can activate Fcγ receptors comprising an ITAM while not engaging Fcγ receptors comprising an ITIM region.

Variant antibodies with S298A, and S292A/E333A/K334, have increased binding affinity to a cynomolgus FcγRIIA, and decreased binding affinity to a cynomolgus FcγRIIB. Such methods can be conducted in vivo or in vitro.

These methods are also useful for identifying the location of amino acid in native sequence antibodies that can be modified to increase binding of the antibody to FcR polypeptides, preferably human and cynomolgus FcγR, comprising an ITAM region and/or to decrease binding affinity to FcγR comprising an ITIM region. Modifications to the amino acid sequence at the identified locations can be prepared by standard methods.

Having generally described the invention, the same will be more readily understood by reference to the following examples, which are provided by way of illustration and are not intended as limiting.

EXAMPLES

Example 1

Molecular Cloning of Cynomolgus and Chimp Fc Receptor DNA and β-2 Microglobulins Materials and Methods Cloning of Cynomolgus Monkey FcγR Since cynomolgus monkey DNA shares approximately 90% homology to human DNA, a series of PCR primers for each FcγR was designed based on the sequence of the corresponding human receptor. Each sense primer starts at a site immediately 5' of the coding region or at the start of the coding region. The antisense primers were designed in the same way, i.e. immediately 3' of the C terminal stop codon or at the C terminal stop codon. Primers incorporated endonuclease restriction sites used to subclone PCR product into a pRK vector (Eaton et al.). The sequences of the primers are shown in Table 1.

TABLE 1

Restriction sites are underlined.

| Receptor | Cyno FcγRI Full-Length | |
|---|---|---|
| Forward Primer | CAGGTCAATC<u>TCTAGA</u>CTCCCACCAGCTTGGAG | (SEQ ID NO:31) |
| Reverse Primer | GGTCAACTAT<u>AAGCTT</u>GGACGGTCCAGATCGAT | (SEQ ID NO:32) |
| Restriction Sites | XbaI/HindIII | |
| Receptor | Cyno FcγRI-H6-GST | |
| Forward Primer | CAGGTCAATC<u>ATCGAT</u>ATGTGGTTCTTGACAGCT | (SEQ ID NO:33) |
| Reverse Primer | GGTCAACTAT<u>GCTAGC</u>ATGGTGATGATGGTGGTGCCAGACAGGAGTTGGTA | (SEQ ID NO:34) |
| Restriction Sites | ClaI NheI | |
| Receptor | Cyno FcγRIIB Full-Length | |
| Forward Primer | CAGGTCAATC<u>TCTAGA</u>ATGGGAATCCTGTCATTCTT | (SEQ ID NO:35) |
| Reverse Primer | GGTCAACTAT<u>AAGCTT</u>CTAAATACGGTTCTGGTC | (SEQ ID NO:36) |
| Restriction Sites | XbaI/HindIII | |
| Receptor | Cyno FcγRIIB-H6-GST | |
| Forward Primer | CAGGTCAATC<u>ATCGAT</u>ATGCTTCTGTGGACAGC | (SEQ ID NO:37) |
| Reverse Primer | GGTCAACTAT<u>GGTGACC</u>TATCGGTGAAGAGCTGC | (SEQ ID NO:38) |
| Restriction Sites | ClaI BstEII | |
| Receptor | Cyno FcγRIIIA Full-Length | |
| Forward Primer | CAGGTCAATC<u>TCTAGA</u>ATGTGGCAGCTGCTCCT | (SEQ ID NO:39) |
| Reverse Primer | TCAACTAT<u>AAGCTT</u>ATGTTCAGAGATGCTGCTG | (SEQ ID NO:40) |
| Restriction Sites | XbaI/HindIII | |

TABLE 1-continued

Restriction sites are underlined.

| Receptor | Cyno FcγRIIIA-H6-GST | |
|---|---|---|
| Forward Primer | CAGGTCAATC<u>TCTAGA</u>ATGTGGCAGCTGCTCCT | (SEQ ID NO:41) |
| Reverse Primer | GGTCAACTAT<u>GGTCACC</u>TTGGTACCCAGGTGGAAA | (SEQ ID NO:42) |
| Restriction Sites | XbaI/BstEII | |
| | | |
| Receptor | Cyno Fc γ Chain | |
| Forward Primer | CAGGTCAATCATCGAT<u>GAATT</u>CCCACCATGATTCCAGC AGTGGTC | (SEQ ID NO:43) |
| Reverse Primer | GGTCAACTAT<u>AAGCTT</u>CTACTGTGGTGGTTTCTCA | (SEQ ID NO:44) |
| Restriction Sites | EcoRI/HindIII | |
| | | |
| Receptor | Cyno β-2 Microglobulin | |
| Forward Primer | CAGGTCAATC<u>ATCGAT</u>TCGGGCCGAGATGTCT | (SEQ ID NO:45) |
| Reverse Primer | GGTCAACTAT<u>TCTAGA</u>TTACATGTCTCGATCCCA | (SEQ ID NO:46) |
| Restriction Sites | ClaI/XbaI | |
| | | |
| Receptor | Cyno FcγRIIA Full-Length | |
| Forward Primer | CAGGTCAATC<u>TCTAGA</u>ATGTCTCAGAATGTATGTC | (SEQ ID NO:47) |
| Reverse Primer | GGTCAACTAT<u>AAGCTT</u>TTAGTTATTACTGTTGTCATA | (SEQ ID NO:48) |
| Restriction Sites | XbaI/HindIII | |
| | | |
| Receptor | Cyno FcγRIIA-H6-GST | |
| Forward Primer | CAGGTCAATC<u>ATCGAT</u>ATGTCTCAGAATGTATGTC | (SEQ ID NO:49) |
| Reverse Primer | GGTCAACTAT<u>GGTGACC</u>CATCGGTGAAGAGCTGC | (SEQ ID NO:50) |
| Restriction Sites | ClaI/BstEII | |
| | | |
| Receptor | Cyno FcRn Full-Length | |
| Forward Primer | CAGGTCAATC<u>ATCGAT</u>AGGTCGTCCTCTCAGC | (SEQ ID NO:51) |
| Reverse Primer | GGTCAACTAT<u>GAATTC</u>TCGGAATGGCGGATGG | (SEQ ID NO:52) |
| Restriction Sites | ClaI/EcoRI | |
| | | |
| Receptor | Cyno FcRn-H6 | |
| Forward Primer | CAGGTCAATC<u>ATCGAT</u>AGGTCGTCCTCTCAGC | (SEQ ID NO:53) |
| Reverse Primer | GGTCAACTAT<u>GAATTC</u>ATGGTGATGATGGTGGTGCGAG GACTTGGCTGGAGTTTC | (SEQ ID NO:54) |
| Restriction Sites | ClaI/EcoRI | |

The cDNA for FcRs was isolated by reverse transcriptase-PCR (GeneAmp, PerkinElmer Life Sciences) of oligo(dT)-primed RNA from cynomologus spleen cells using primers as shown in Table 1. The cDNA was subcloned into previously described pRK mammalian cell expression vectors, as described in Eaton et al., 1986, *Biochemistry,* 25:8343–8347. PCR reactions were set up using 200 ng of cDNA vector library from cynomolgus spleen and ExTaq Premix (Panvera, Madison, Wis.) according to the manufacturers instructions. After denaturation at 90° C. for 30 s, 25 cycles were run with annealing at 55° C. for 1 min, elongation at 72° C. for 3 min, and denaturation at 98° C. for 30 s. DNA bands migrating at the expected size (FcγRI, FcγRIIIA, FcRn, 1100 base pairs; FcγRIIA, FcγRIIB, 1000 base pairs; Fcγ chain, 300 base pairs; β-2 microglobulin, 400 base pairs) were isolated, cloned into pRK vectors, then transformed into *Escherichia coli* XL1-Blue (Stratagene, San Diego, Calif.). Individual clones were selected and double-stranded DNA for each was purified using Qiagen mini-prep DNA kits (cat. #27106; Qiagen). DNA sequencing was performed on an Applied Biosystems model 377 sequencer using Big-Dye Terminator Cycle Sequencing kits (Applied Biosystems, Foster City, Calif.).

Initial PCR reactions for FcγRIIA did not reveal a PCR product. To determine whether or not FcγRIIA was present in cynomolgus monkeys, a sense primer was designed in a region conserved between human FcγRIIA, human FcγRIIB, and cynomolgus FcγRIIB (OF1, Table 2). An antisense primer was designed based on the consensus sequence in the region encoding the ITAM of human FcγRIIA (OR1, Table 2). Using these two PCR primers (OF1, OR1) and the PCR protocol described above, a PCR product of approximately 700 base pairs was obtained. The PCR band was isolated and subcloned into a pRK vector, individual clones were isolated and sequenced as described above. Sequence analysis revealed that the fragment had 90% identity to human FcγRIIA.

In order to determine the DNA sequence at the 5' end of the receptor, a nested PCR reaction was utilized. For the first step of the nested PCR reaction, a sense PCR primer (OF2, Table 2) was designed to lay down on the pRK vector 5' of the vector cloning site. This primer was used in conjunction with reverse primer OR1. The PCR reaction was performed on the cDNA library as described above, the product was diluted 1:500 and 1 μL was used as a template for the second step of the nested PCR reaction. Due to the fact that primer OF2 would lay down on all members of the cDNA library (all members being cloned into separate pRK vectors), only a small quantity of PCR fragment was obtained and hence this was used as a template for amplification in the second step. The sense primer (OF3, Table 2) for the second step was designed to lay down on the pRK vector sequence 3' of OF2 and the reverse primer (OR2, Table 2) was based on partial sequence of FcγRIIA determined above. The second step of the nested PCR reaction revealed a band of approximately 600 base pairs. The band was isolated and individual clones were prepared and sequenced as described above.

The DNA sequence at the 3' end of the receptor was determined in a similar manner. An initial PCR reaction on the cDNA library was performed using the forward primer OF4, designed from the sequence of the FcγRIIA fragment, and the reverse primer OR3, designed to lay down in the pRK vector 3' from the end of the FcγRIIA. The resultant fragment was used as template for the second step of the nested PCR reaction. The second step used the forward primer OF5, designed from the sequence of the Fcγ RIIA fragment, and the reverse primer OR4, designed to lay down in the pRK vector 5' from primer OR3. The second step of the nested PCR reaction revealed a band of approximately 800 base pairs. The band was isolated and individual clones were sequenced as described above. PCR primers for the full length FcγRIIA were designed based on the information acquired from the nested PCR reactions. Full length FcγRIIA was cloned using the method described for all other receptors. The sequences of the primers described above are shown in Table 2.

TABLE 2

| | | |
|---|---|---|
| OF1 | CAGGTCAATC TCTAGACAGT GGTTCCACAA TGG | (SEQ ID NO:55) |
| OR1 | GGTCAACTAT AAGCTTAAGA GTCAGGTAGA TGTTT | (SEQ ID NO:56) |
| OF2 | CAGGTCAATC TCTAGAATAC ATAACCTTAT GTATCAT | (SEQ ID NO:57) |
| OF3 | CAGGTCAATC TCTAGATATA GAATAACATC CACTTTG | (SEQ ID NO:58) |
| OR2 | GGTCAACTAT AAGCTTCAGA GTCATGTAGC CG | (SEQ ID NO:59) |
| OF4 | CAGGTCAATC TCTAGAATTC CACTGATCCT GTGAA | (SEQ ID NO:60) |
| OR3 | GGTCAACTAT AAGCTTGCTT TATTTGTGAA ATTTGTG | (SEQ ID NO:61) |
| OF5 | CAGGTCAATC TCTAGAACTT GGACGTCAAA CGATT | (SEQ ID NO:62) |
| OR4 | GGTCAACTAT AAGCTTCTGC AATAAACAAG TTGGG | (SEQ ID NO:63) |

Example 2

Alignment of Nucleotide and Amino Acid Sequences of Cynomolgus Chimp and Human FcγR Nucleotide and amino acid sequences for FcR polypeptides from human, cynomolgus and chimps were aligned and % sequence identity calculated.

Nucleotide and amino acid sequences of primate and human proteins were aligned manually and differences in nucleotide or protein sequence noted. Percent identity was calculated as [number of identical residues]/[number of total residues]. When the sequences differed in the total number of residues, two values for percent identity are provided, using the two different numbers for total residues. Nucleotide sequences begin at the coding sequence for the signal sequence.

The alignment of nucleic acid sequences for human (SEQ ID NO: 2) and cynomolgus FcγRI α-chain (SEQ ID NO: 1) as shown in Table 3 below. The dots indicate locations of nucleotide sequence differences. An analysis of the % sequence identity shows that the human and cynomolgus nucleotide sequences encoding FcγRI α-chain have about 91% or 96% sequence identity depending on whether the nucleotides of 3' extensions are included in the calculation.

TABLE 3

Alignment of Human and Cynomolgus High-Affinity FcγRI DNA

```
1030 matches in an overlap of 1074: 95.9% identity
1030 matches in an overlap of 1128: 91.3% identity
                10        20        30        40        50
Human   ATGTGGTTCTTGACAACTCTGCTCCTTTGGGTTCCAGTTGATGGGCAAGT
                          •
Cyno    ATGTGGTTCTTGACAGCTCTGCTCCTTTGGGTTCCAGTTGATGGGCAAGT 60        70        80        90       100
Human   GGACACCACAAAGGCAGTGATCACTTTGCAGCCTCCATGGGTCAGCGTGT
           •
Cyno    GGATACCACAAAGGCAGTGATCACTTTGCAGCCTCCATGGGTCAGCGTGT 110       120       130       140       150
Human   TCCAAGAGGAAACCGTAACCTTGCACTGTGAGGTGCTCCATCTGCCTGGG
                   •      •  •         •    •   •
Cyno    TCCAAGAGGAAACTGTAACCTTACAGTGTGAGGTGCCCCGTCTGCCTGGG 160       170       180       190       200
Human   AGCAGCTCTACACAGTGGTTTCTCAATGGCACAGCCACTCAGACCTCGAC
                 •
Cyno    AGCAGCTCCACACAGTGGTTTCTCAATGGCACAGCCACTCAGACCTCGAC 210       220       230       240       250
Human   CCCCAGCTACAGAATCACCTCTGCCAGTGTCAATGACAGTGGTGAATACA
        •                                •
Cyno    TCCCAGCTACAGAATCACCTCTGCCAGTGTCAAGGACAGTGGTGAATACA 260       270       280       290       300
Human   GGTGCCAGAGAGGTCTCTCAGGGCGAAGTGACCCCATACAGCTGGAAATC
                         •
Cyno    GGTGCCAGAGAGGTCCCTCAGGGCGAAGTGACCCCATACAGCTGGAAATC 310       320       330       340       350
Human   CACAGAGGCTGGCTACTACTGCAGGTCTCCAGCAGAGTCTTCACGGAAGG
                 •                •                  •
Cyno    CACAGAGACTGGCTACTACTGCAGGTATCCAGCAGAGTCTTCACAGAAGG 360       370       380       390       400
Human   AGAACCTCTGGCCTTGAGGTGTCATGCGTGGAAGGATAAGCTGGTGTACA
                                        •
Cyno    AGAACCTCTGGCCTTGAGGTGTCATGCATGGAAGGATAAGCTGGTGTACA 410       420       430       440       450
Human   ATGTGCTTTACTATCGAAATGGCAAAGCCTTTAAGTTTTTCCACTGGAAT
                          •                      • •
Cyno    ATGTGCTTTACTATCAAAATGGCIAAAGCCTTTAAGTTTTTCTACCGGAAT 460       470       480       490       500
Human   TCTAACCTCACCATTCTGAAAACCAACATAAGTCACAATGGCACCTACCA
          • •                                 • •
Cyno    TCTCAACTCACCATTCTGAAAACCAACATAAGTCACAACGGCGCCTACCA 510       520       530       540       550
Human   TTGCTCAGGCATGGGAAAGCATCGCTACACATCAGCAGGAATATCTGTCA
        •                                        •
Cyno    CTGCTCAGGCATGGGAAAGCATCGCTACACATCAGCAGGAGTATCTGTCA 560       570       580       590       600
Human   CTGTGAAAGAGCTATTTCCAGCTCCAGTGCTGAATGCATCTGTGACATCC
                                                   •
Cyno    CTGTGAAAGAGCTATTTCCAGCTCCAGTGCTGAATGCATCCGTGACATCC 610       620       630       640       650
Human   CCACTCCTGGAGGGGAATCTGGTCACCCTGAGCTGTGAAACAAAGTTGCT
          •
Cyno    CCGCTCCTGGAGGGGAATCTGGTCACCCTGAGCTGTGAAACAAAGTTGCT 660       670       680       690       700
Human   CTTGCAGAGGCCTGGTTTGCAGCTTTACTTCTCCTTCTACATGGGCAGCA
        • •
Cyno    TCTGCAGAGGCCTGGTTTGCAGCTTTACTTCTCCTTCTACATGGGCAGCA 710       720       730       740       750
Human   AGACCCTGCGAGGCAGGAACACATCCTCTGAATACCAAATACTAACTGCT
                                  •
Cyno    AGACCCTGCGAGGCAGGAACACGTCCTCTGAATACCAAATACTAACTGCT
```

TABLE 3-continued

Alignment of Human and Cynomolgus High-Affinity FcγRI DNA

```
              760       770       780       790       800
Human   AGAAGAGAAGACTCTGGGTTATACTGGTGCGAGGCTGCCACAGAGGATGG
                               •          • •      • •
Cyno    AGAAGAGAAGACTCTGGGTTTTACTGGTGCGAGGCCACCACAGAAGACGG 810       820       830       840       850
Human   AAATGTCCTTAAGCGCAGCCCTGAGTTGGAGCTTCAAGTGCTTGGCCTCC Cyno    AAATGTCCTTAAGCGCAGCCCTGAGTTGGAGCTTCAAGTGCTTGGCCTCC 860       870       880       890       900
Human   AGTTACCAACTCCTGTCTGGTTTCATGTCCTTTTCTATCTGGCAGTGGGA
                                •                 •
Cyno    AGTTACCAACTCCTGTCTGGCTTCATGTCCTTTTCTATCTGGTAGTGGGA 910       920       930       940       950
Human   ATAATGTTTTTAGTGAACACTGTTCTCTGGGTGACAATACGTAAAGAACT Cyno    ATAATGTTTTTAGTGAACACTGTTCTCTGGGTGACAATACGTAAAGAACT 960       970       980       990      1000
Human   GAAAAGAAAGAAAAAGTGGGATTTAGAAATCTCTTTGGATTCTGGTCATG
                             •              •
Cyno    GAAAAGAAAGAAAAAGTGGAATTTAGAAATATCTTTGGATTCTGCTCATG 1010      1020      1030      1040      1050
Human   AGAAGAAGGTAATTTCCAGCCTTCAAGAAGACAGACATTTAGAAGAAGAG
                     •
Cyno    AGAAGAAGGTAACTTCCAGCCTTCAAGAAGACAGACATTTAGAAGAAGAG 1060      1070      1080      1090      2000
Human   CTGAAATGTCAGGAACAAAAAGAAGAACAGCTGCAGGAAGGGGTGCACCG
              • •                • •
Cyno    CTGAAGAGTCAGGAACAAGAATAA 1110      1120
Human   GAAGGAGCCCCAGGGGGCCACGTAGCAG 3' extension
```

The Human DNA sequence shown in Table 3 has GenBank Accession No. L03418. Porges, A. J., Redecha, P. B., Doebele, R., Pan, L. C., Salmon, J. E. and Kimberly, R. P., *Novel Fc gamma receptor I family gene products in human mononuclear cells*, J. Clin. Invest. 90, 2102–2109 (1992).

An alignment of nucleic acid sequences encoding human (SEQ ID NO: 14) and cynomolgus (SEQ ID NO: 13) gamma chain is shown in Table 4.

Analysis of the % sequence identity shows that the nucleic acid sequences encoding human and cynomolgus FcγRI/III gamma chain have about 99% identity.

TABLE 4

Alignment of Human and Cynomolgus Gamma-Chain DNA 258 matches in an overlap of 261: 98.9% identity

```
              10        20        30        40        50
Human   ATGATTCCAGCAGTGGTCTTGCTCTTACTCCTTTTGGTTGAACAAGCACC Cyno    ATGATTCCAGCAGTGGTCTTGCTCTTACTCCTTTTGGTTGAACAAGCAGC 60        70        80        90       100
Human   GGCCCTGGGAGAGCCTCAGCTCTGCTATATCCTGGATGCCATCCTGTTTC Cyno    GGCCCTGGGAGAGCCTCAGCTCTGCTATATCCTGGATGCCATCCTGTTTC 110       120       130       140       150
Human   TGTATGGAATTGTCCTCACCCTCCTCTACTGTCGACTGAAGATCCAAGTG Cyno    TGTATGGAATTGTCCTCACCCTCCTCTACTGTCGACTGAAGATCCAAGTG 160       170       180       190       200
Human   CGAAAGGCAGCTATAACCAGCTATGAGAAATCAGATGGTGTTTACACGGG
                                                •
```

TABLE 4-continued

Alignment of Human and Cynomolgus Gamma-Chain DNA

```
Cyno    CGAAAGGCAGCTATAGCCAGCTATGAGAAATCAGATGGTGTTTACACGGG 210       220       230       240       250
Human   CCTGAGCACCAGGAACCAGGAGACTTACGAGACTCTGAAGCATGAGAAAC
                            •         •
Cyno    CCTGAGCACCAGGAACCAGGAAACTTATGAGACTCTGAAGCATGAGAAAC 260
Human   CACCACAGTAG Cyno    CACCACAGTAG
```

The DNA sequence for the human gamma chain as GenBank Accession No. M33195 J05285. Kuester, H., Thompson, H. and Kinet, J.-P., *Characterization and expression of the gene for the human receptor gamma subunit: Definition of a new gene family*, J. Biol. Chem. 265, 6448–6452 (1990).

An alignment of the human (SEQ ID NO: 4), chimp (SEQ ID NO: 22) and cynomolgus (SEQ ID NO: 3) nucleic acid sequence encoding FcγRIIA is shown in Table 5. An analysis of the % sequence identity shows that the human and cynomolgus sequences encoding FcγRIIA have about 94% sequence identity. A comparison of chimp and human sequences encoding FcγRIIA have about 99% sequence identity.

TABLE 5

Alignment of Human, Cynomolgus and Chimp Low-Affinity FcγRIIA DNA

```
Human/Cyno   878 matches in an overlap of 933: 94.1% identity
                  without one gap of three nuoleotides
             878 matches in an overlap of 936: 93.8% identity
                  with one gap of three nucleotides Human/Chimp  924 matches in an overlap of 933: 99.0% identity
                  without one gap of three nucleotides
             924 matches in an overlap of 936: 98.7% identity
                  with one gap of three nucleotides 10        20        30        40        50
Chimp   ATGTCTCAGAATGTATGTCCCAGAAACCTGTGGCTGCTTCAACCATTGAC Human   ATGTCTCAGAATGTATGTCCCAGAAACCTGTGGCTGCTTCAACCATTGAC
                              • •
Cyno    ATGTCTCAGAATGTATGTCCCGGCAACCTGTGGCTGCTTCAACCATTGAC 60        70        80        90       100
Chimp   AGTTTTGCTGCTGCTGGCTTCTGCAGACAGTCAAGCT---GCTCCCCCAA
                                                •••
Human   AGTTTTGCTGCTGCTGGCTTCTGCAGACAGTCAAGCTGCAGCTCCCCCAA
                                         •  •••        •
Cyno    AGTTTTGCTGCTGCTGGCTTCTGCAGACAGTCAAACT---GCTCCCCCGA 110       120       130       140       150
Chimp   AGGCTGTGCTGAAACTTGAGCCCCCGTGGATCAACGTGCTCCAGGAGGAC Human   AGGCTGTGCTGAAACTTGAGCCCCCGTGGATCAACGTGCTCCAGGAGGAC
                            •                                •
Cyno    AGGCTGTGCTGAAACTCGAGCCCCCGTGGATCAACGTGCTCCGGGAGGAC
                160       170       180       190       200
Chimp   TCTGTGACTCTGACATGCCGGGGGGCTCGCAGCCCTGAGAGCGACTCCAT
                                  •
Human   TCTGTGACTCTGACATGCCAGGGGGCTCGCAGCCCTGAGAGCGACTCCAT
                        •  ••   •    •            •         •
Cyno    TCTGTGACTCTGACGTGCGGGGGCGCTCACAGCCCTGACAGCGACTCCAC 210       220       230       240       250
Chimp   TCAGTGGTTCCACAATGGGAATCTCATCCCCACCCACACGCAGCCCAGCT
                                                •
Human   TCAGTGGTTCCACAATGGGAATCTCATTCCCACCCACACGCAGCCCAGCT
                                        •  •            •
Cyno    TCAGTGGTTCCACAATGGGAATCGCATCCCCACCCACACACAGCCCAGCT 260       270       280       290       300
```

TABLE 5-continued

Alignment of Human, Cynomolgus and Chimp Low-Affinity FcγRIIA DNA

```
Chimp ACAGGTTCAAGGCCAACAACAATGACAGCGGGGAGTACACGTGCCAGACT
Human ACAGGTTCAAQGCCAACAACAATGACAGCGGGGAGTACACGTGCCAGACT
Cyno  ACAGGTTCAAGGCCAACAACAATGATAGCGGGGAGTACAGGTGCCAGACT 310       320       330       340       350
Chimp GGCCAGACCAGCCTCAGCGACCCTGTGCATCTGACTGTGCTTTCCGAATG
Human GGCCAGACCAGCCTCAGCGACCCTGTGCATCTGACTGTGCTTTCCGAATG
Cyno  GGCCGGACCAGCCTCAGCGACCCTGTTCATCTGACTGTGCTTTCTGAGTC 360       370       380       390       400
Chimp GCTGGTGCTCCAGACCCCTCACCTGGAGTTCCAGGAGGGAGAAACCATCG
Human GCTGGTGCTCCAGACCCCTCACCTGGAGTTCCAGGAGGGAGAAACCATCA
Cyno  GCTGGCGCTTCAGACCCCTCACCTGGAGTTCCGGGAGGGAGAAACCATCA 410       420       430       440       450
Chimp TGCTGAGGTGCCACAGCTGGAAGGACAAGCCTCTGGTCAAGGTCACATTC
Human TGCTGAGGTGCCACAGCTGGAAGGACAAGCCTCTGGTCAAGGTCACATTC
Cyno  TGCTGAGGTGCCACAGCTGGAAGGACAAGCCTCTGATCAAGGTCACATTC 460       470       480       490       500
Chimp TTCCAGAATGGAAAATCCCAGAAATTCTCCCATTTGGATCCCAACCTCTC
Human TTCCAGAATGGAAAATCCCAGAAATTCTCCCGTTTGGATCCCACCTTCTC
Cyno  TTCCAGAATGGAATAGCCAAGAAATTTTCCCATATGGATCCCAATTTCTC 510       520       530       540       550
Chimp CATCCCACAAGCAAACCACAGTCACAGTGGTGATTACCACTGCACAGGAA
Human CATCCCACAAGCAAACCACAGTCACAGTGGTGATTACCACTGCACAGGAA
Cyno  CATCCCACAAGCAAACCACAGTCACAGTGGTGATTACCACTGCACAGGAA 560       570       580       590       600
Chimp ACATAGGCTACACGCTGTTCTCATCCAAGCCTGTGACCATCACTGTCCAA
Human ACATAGGCTACACGCTGTTCTCATCCAAGCCTGTGACCATCACTGTCCAA
Cyno  ACATAGGCTACACACCATACTCATCCAAACCTGTGACCATCACTGTCCAA 610       620       630       640       650
Chimp GCGCCCAGCGTGGGCAGCTCTTCACCAGTGGGATCATTGTGGCTGTGGT
Human GTGCCCAGCATGGGCAGCTCTTCACCAATGGGATCATTGTGGCTGTGGT
Cyno  GTCCCCAGCGTGGGCAGCTCTTCACCGATGGGATCATTGTGGCTGTGGT 660       670       680       690       700
Chimp CATTGCGACTGCTGTAGCAGCCATTGTTGCTGCTGTAGTGGCCTTGATCT
Human CATTGCGACTGCTGTAGCAGCCATTGTTGCTGCTGTAGTGGCCTTGATCT
Cyno  CACTGGGATTGCTGTAGCGGCCATTGTTGCTGCTGTAGTGGCCTTGATCT 710       720       730       740       750
Chimp ACTGCAGGAAAAAGCGGATTTCAGCCAATTCCACTGATCCTGTGAAGGCT
Human ACTGCAGGAAAAAGCGGATTTCAGCCAATTCCACTGATCCTGTGAAGGCT
Cyno  ACTGCAGGAAAAAGCGGATTTCAGCCAATTCCACTGATCCTGTGAAGGCT 760       770       780       790       800
Chimp GCCCAATTTGAGCCACCTGGACGTCAAATGATTGCCATCAGAAAGAGACA
Human GCCCAATTTGAGCCACCTGGACGTCAAATGATTGCCATCAGAAAGAGACA
Cyno  GCCCGATTTGAGCCACTTGGACGTCAAACGATTGCCCTCAGAAAGAGACA
```

TABLE 5-continued

Alignment of Human, Cynomolgus and Chimp Low-Affinity FcγRIIA DNA

```
              810        820        830        840        850
Chimp  ACTTGAAGAAACCAACAATGACTATGAAACAGCTGACGGCGGCTACATGA Human  ACTTGAAGAAACCAACAATGACTATGAAACAGCTGACGGCGGCTACATGA
                                      ·
Cyno   ACTTGAAGAAACCAACAATGACTATGAAACAGCCGACGGCGGCTACATGA 860        870        880        890        900
Chimp  CTCTGAACCCCAGGGCACCTACTGACGATGATAAAAACATCTACCTGACT Human  CTCTGAACCCCAGGGCACCTACTGACGATGATAAAAACATCTACCTGACT
                                   ·       ·
Cyno   CTCTGAACCCCAGGGCACCTACTGATGATGATAGAAACATCTACCTGACT 910        920        930
Chimp  CTTCCTCCCAACGACCATGTCAACAGTAATAACTAA Human  CTTCCTCCCAACGACCATGTCAACAGTAATAACTAA
          ·       ·  ·  ·
Cyno   CTTTCTCCCAACGACTATGACAACAGTAATAACTAA
```

The sequence for the human FcγRIIA receptor has GenBank Accession No. M28697. Seki, T. *Identification of multiple isoforms of the low-affinity human IgG Fc receptor*, Immunogenetics 30, 5–12 (1989).

Alignment of the nucleic acid sequences encoding human (SEQ ID NO: 6) and cynomolgus (SEQ ID NO: 5) FcγRIIB is shown in Table 6.

Analysis of the % sequence identity shows that the human and cynomolgus sequences encoding FcγRIIB have about 94% identity.

TABLE 6

Alignment of Human and Cynomolgus Low-Affinity FcγRIIB DNA 837 matches out of 885: 94.6% identity (without gap)
837 matches out of 894: 93.6% identity (with gap)

```
              10         20         30         40         50
Human  ATGGGAATCCTGTCATTCTTACCTGTCCTTGCCACTGAGAGTGACTGGGC
                                       ·
Cyno   ATGGGAATCCTGTCATTCTTACCTGTCCTTGCTACTGAGAGTGACTGGGC 60         70         80         90         100
Human  TGACTGCAAGTCCCCCCAGCCTTGGGGTCATATGCTTCTGTGGACAGCTG
                  ·                      ·  ·
Cyno   TGACTGCAAGTCCTCCCAGCCTTGGGGCCACATGCTTCTGTGGACAGCTG 110        120        130        140        150
Human  TGCTATTCCTGGCTCCTGTTGCTGGGACACCTGCAGCTCCCCCAAAGGCT
                                                     ·
Cyno   TGCTATTCCTGGCTCCTGTTGCTGGGACACCTGCAGCTCCCCCGAAGGCT 160        170        180        190        200
Human  GTGCTGAAACTCGAGCCCCAGTGGATCAACGTGCTCCAGGAGGACTCTGT
                              ·                    ·
Cyno   GTGCTGAAACTCGAGCCCCGTGGATCAACGTGCTCCGGGAGGACTCTGT 210        220        230        240        250
Human  GACTCTGACATGCCGGGGGACTCACAGCCCTGAGAGCGACTCCATTCAGT
                  · ·   ··            ·     ·      ·
Cyno   GACTCTGACGTGCGGGGGCGCTCACAGCCCTGACAGCGACTCCACTCAGT 260        270        280        290        300
Human  GGTTCCACAATGGGAATCTCATTCCCACCCACACGCAGCCCAGCTACAGG
          ·
Cyno   CGTTCCACAATGGGAATCTCATCCCCACCCACACGCAGCCCAGCTACAGG 310        320        330        340        350
Human  TTCAAGGCCAACAACAATGACAGCGGGGAGTACACGTGCCAGACTGGCCA
                               ·           ·           ·
Cyno   TTCAAGGCCAACAACAATGATAGCGGGGAGTACACGTGCCAGACTGGCCG
```

TABLE 6-continued

Alignment of Human and Cynomolgus Low-Affinity FcγRIIB DNA

```
              360       370       380       390       400
Human  GACCAGCCTCAGCGACCCTGTGCATCTGACTGTGCTTTCTGAGTGGCTGG
                         •
Cyno   GACCAGCCTCAGCGACCCTGTTCATCTGACTGTGCTTTCTGAGTGGCTGG 410       420       430       440       450
Human  TGCTCCAGACCCCTCACCTGGAGTTCCAGGAGGGAGAAACCATCGTGCTG
         •                          •                •
Cyno   CGCTCCAGACCCCTCACCTGGAGTTCCGGGAGGGAGAAACCATCTTGCTG 460       470       480       490       500
Human  AGGTGCCACAGCTGGAAGGACAAGCCTCTGGTCAAGGTCACATTCTTCCA
                                        •
Cyno   AGGTGCCACAGCTGGAAGGACAAGCCTCTGATCAAGGTCACATTCTTCCA 510       520       530       540       550
Human  GAATGGAAAATCCAAGAAATTTTCCCGTTCGGATCCCAACTTCTCCATCC
             •                       • •• •
Cyno   GAATGGAATATCCAAGAAATTTTCCCATATGAATCCCAACTTCTCCATCC 560       570       580       590       600
Human  CACAAGCAAACCACAGTCACAGTGGTGATTACCACTGCACAGGAAACATA Cyno   CACAAGCAAACCACAGTCACAGTGGTGATTACCACTGCACAGGAAACATA 610       620       630       640       650
Human  GGCTACACGCTGTACTCATCCAAGCCTGTGACCATCACTGTCCAAGCTCC
            • ••         •                            ••
Cyno   GGCTACACACCATACTCATCCAAACCTGTCACCATCACTGTCCAAGTGCC 660       670       680       690       700
Human  ---------CAGCTCTTCACCGATGGGGATCATTGTGGCTGTGGTCACTG
       •••••••••           •
Cyno   CAGCATGGGCAGCTCTTCACCGATAGGGATCATTGTGGCTGTGGTCACTG 710       720       730       740       750
Human  GGATTGCTGTAGCGGCCATTGTTGCTGCTGTAGTGGCCTTGATCTACTGC Cyno   GGATTGCTGTAGCGGCCATTGTTGCTGCTGTAGTGGCCTTGATCTACTGC 760       770       780       790       800
Human  AGGAAAAAGCGGATTTCAGCCAATCCCACTAATCCTGATGAGGCTGACAA
                                              •
Cyno   AGGAAAAAGCGGATTTCAGCCAATCCCACTAATCCTGACGAGGCTGACAA 810       820       830       840       850
Human  AGTTGGGGCTGAGAACACAATCACCTATTCACTTCTCATGCACCCGGATG
                                                 •   •
Cyno   AGTTGGGGCTGAGAACACAATCACCTATTCACTTCTCATGCATCCGGACG 860       870       880
Human  CTCTGGAAGAGCCTGATGACCAGAACCGTATTTAG
                           •      • •
Cyno   CTCTGGAAGAGCCTGATGACCAAAACCGNGTTTAG
```

The human sequence for FcγRIIB has GenBank Accession No. X52473. Engelhardt, W., Greerds, C. and Frey, J., *Distribution, inducibility and biological function of the cloned and expressed human beta Fc receptor II*, Eur. J. Immunol. 20 (6), 1367–1377 (1990).

Alignment of the nucleic acid sequences encoding a human (SEQ ID NO: 8) and cynomolgus (SEQ ID NO: 7) FcγRIIIA is shown in Table 7.

Analysis of the % sequence identity shows that the human and cynomolgus nucleic acid sequences encoding FcγRIIIA have about 96% identity.

TABLE 7

Alignment of Human and Cynomolgus Low-Affinity FcγRIIIA DNA 733 matches in an overlap of 765: 95.8% identity

```
                10        20        30        40        50
Human  ATGTGGCAGCTGCTCCTCCCAACTGCTCTGCTACTTCTAGTTTCAGCTGG
```

TABLE 7-continued

Alignment of Human and Cynomolgus Low-Affinity FcγRIIIA DNA

```
Cyno   ATGTGCCAGCTGCTCCTCCCAACTGCTCTGCTACTTCTAGTTTCAGCTGG 60         70         80         90        100
Human   CATGCGGACTGAAGATCTCCCAAAGGCTGTGGTGTTCCTGGAGCCTCAAT
                   •
Cyno    CATGCGGGCTGAAGATCTCCCAAAGGCTGTGGTGTTCCTGGAGCCTCAAT 110        120        130        140        150
Human   GGTACAGGGTGCTCGAGAAGGACAGTGTGACTCTGAACTGCCAGGGAGCC
                                 •
Cyno    GGTACAGGGTGCTCGAGAAGGACCGTGTGACTCTGAAGTGCCAGGGAGCC 160        170        180        190        200
Human   TACTCCCCTGAGGACAATTCCACACAGTGGTTTCACAATGAGAGCCTCAT
                                      •
Cyno    TACTCCCCTGAGGACAATTCCACACGGTGGTTTCACAATGAGAGCCTCAT 210        220        230        240        250
Human   CTCAAGCCAGGCCTCGAGCTACTTCATTGACGCTGCCACAGTCGACGACA
                    •                •  ••       •    •   •
Cyno    CTCAAGCCAGACCTCGAGCTACTTCATTGCTGCTGCCAGAGTCAACAACA 260        270        280        290        300
Human   GTGGAGAGTACAGGTGCCAGACAAACCTCTCCACCCTCAGTGACCCGGTG
                                    •         •
Cyno    GTGGAGAGTACAGGTGCCAGACAAGCCTCTCCACACTCAGTGACCCGGTG 310        320        330        340        350
Human   CAGCTAGAAGTCCATATCGGCTGGCTGTTGCTCCAGGCCCCTCGGTGGGT
                 •                     •
Cyno    CAGCTGGAAGTCCATATCGGCTGGCTATTGCTCCAGGCCCCTCGGTGGGT 360        370        380        390        400
Human   GTTCAAGGAGGAAGACCCTATTCACCTGAGGTGTCACAGCTGGAAGAACA
                            ••
Cyno    GTTCAAGGAGGAAGAATCTATTCACCTGAGGTGTCACAGCTGGAAGAACA 410        420        430        440        450
Human   CTGCTCTGCATAAGGTCACATATTTACAGAATGGCAAAGGCAGGAAGTAT
           ••                          •
Cyno    CTCTTCTGCATAAGGTCACGTATTTACAGAATGGCAAAGGCAGGAAGTAT 460        470        480        490        500
Human   TTTCATCATAATTCTGACTTCTACATTCCAAAAGCCACACTCAAAGACAG
                •
Cyno    TTTCATCAGAATTCTGACTTCTACATTCCAAAAGCCACACTCAAAGACAG 510        520        530        540        550
Human   CGGCTCCTACTTCTGCAGGGGGCTTTTTGGGAGTAAAAATGTGTCTTCAG
                                •  •            •
Cyno    CGGCTCCTACTTCTGCAGGGGACTTATTGGGAGTAAAAATGTATCTTCAG 560        570        580        590        600
Human   AGACTGTGAACATCACCATCACTCAAGGTTTGGCAGTGTCAACCATCTCA
                                        •            •
Cyno    AGACTGTGAACATCACCATCACTCAAGATTTGGCAGTGTCATCCATCTCA 610        620        630        640        650
Human   TCATTCTTTCCACCTGGGTACCAAGTCTCTTTCTGCTTGGTGATGGTACT
                                                  •
Cyno    TCATTCTTTCCACCTGGGTACCAAGTCTCTTTCTGCCTGGTGATGGTACT 660        670        680        690        700
Human   CCTTTTTGCAGTGGACACAGGACTATATTTCTCTGTGAAGACAAACATTC
                                               •  •  •
Cyno    CCTTTTTGCAGTGGACACAGGACTATATTTCTCTATGAAGAAAAGCATTC 710        720        730        740        750
Human   GAAGCTCAACAAGAGACTGGAAGGACCATAAATTTAAATGGAGAAAGGAC
            •             •    •                      •
Cyno    CAAGCTCAACAAGGGACTGGGAGGACCATAAATTTAAATGGAGCAAGGAC 760
Human   CCTCAAGACAAATCA Cyno    CCTCAAGACAAATGA
```

The human sequence for FcγIII has GenBank Accession No. X52645 M31937). Ravetch, J. V. and Perussia, B., *Alternative membrane forms of Fc gamma RIII(CD16) on human natural killer cells and neutrophils. Cell type-specific expression of two genes that differ in single nucleotide substitutions*, J. Exp. Med. 170 (2), 481–497 (1989).

Alignment of the nucleic acid sequences encoding a human (SEQ ID NO: 24) and cynomolgus (SEQ ID NO: 23) β-2 microglobulin is shown in Table 8.

Analysis of the % sequence identity shows that the human and cynomolgus nucleic acid sequences encoding β-2 microglobulin have about 95% identity.

TABLE 8

Alignment of Human and Cynomolgus β2-Microglobulin DNA

341/360 = 94.7% identity

```
               10        20        30        40        50
Human  ATGTCTCGCTCCGTGGCCTTAGCTGTGCTCGCGCTACTCTCTCTTTCTGG
         ..         . ..
Cyno   ATGTCTCCCTCAGTGGCCTTAGCCGTGCTGGCGCTACTCTCTCTTTCTGG 60        70        80        90       100
Human  CCTGGAGGCTATCCAGCGTACTCCAAAGATTCAGGTTTACTCACGTCATC
                                                       .
Cyno   CCTGGAGGCTATCCAGCGTACTCCAAAGATTCAGGTTTACTCACGCCATC 110       120       130       140       150
Human  CAGCAGAGAATGGAAAGTCAAATTTCCTGAATTGCTATGTGTCTGGGTTT
         .                .                          .
Cyno   CACCAGAGAATGGAAAGCCAAATTTCCTGAATTGCTATGTGTCTGGATTT 160       170       180       190       200
Human  CATCCATCCGACATTGAAGTTGACTTACTGAAGAATGGAGAGAGAATTGA
            ..                                 .  ...
Cyno   CATCCATCTGATATTGAAGTTGACTTACTGAAGAATGGAGAGAAAATGGG 210       220       230       240       250
Human  AAAAGTGGAGCATTCAGACTTGTCTTTCAGCAAGGACTGGTCTTTCTATC
                                          .
Cyno   AAAAGTGGAGCATTCAGACTTGTCTTTCAGCAAAGACTGGTCTTTCTATC 260       270       280       290       300
Human  TCTTGTACTACACTGAATTCACCCCCACTGAAAAAGATGAGTATGCCTGC
                                   .
Cyno   TCTTGTACTACACTGAATTCACCCCCAATGAAAAAGATGAGTATGCCTGC 310       320       330       340       350
Human  CGTGTGAACCATGTGACTTTGTCACAGCCCAAGATAGTTAAGTGGGATCG
                                ..    . ..
Cyno   CGTGTGAACCATGTGACTTTGTCAGGGCCCAGGACAGTTAAGTGGGATCG 360
Human  AGACATGTAA Cyno   AGACATGTAA
```

The DNA sequence for the human β-2 microglobulin has GenBank Accession No. AB021288. Matsumoto, K., Minamitani, T., *Human mRNA for beta 2-microglobulin*, DDBJ/EMBL/GenBank databases (1998).

Alignment of the nucleic acid sequences encoding a human (SEQ ID NO: 28) and cynomolgus (SEQ ID NO: 27) FcRn α-chain is shown in Table 9.

Analysis of the % sequence identity shows that the human and cynomolgus nucleic acid sequences encoding FcRn α-chain have about 97% identity.

TABLE 9

Alignment of Human and Cynomolgus FcRn α-Chain DNA

1062/1098 = 96.7% identity

```
                 10        20        30        40        50
Human  ATGGGGGTCCCGCGGCCTCAGCCCTGGGCGCTGGGGCTCCTGCTCTTTCT
         •
Cyno   ATGAGGGTCCCGCGGCCTCAGCCCTGGGCGCTGGGGCTCCTGCTCTTTCT 60        70        80        90       100
Human  CCTTCCTGGGAGCCTGGGCGCAGAAAGCCACCTCTCCCTCCTGTACCACC
         • •
Cyno   CCTGCCCGGGAGCCTGGGCGCAGAAAGCCACCTCTCCCTCCTGTACCACC 110       120       130       140       150
Human  TTACCGCGGTGTCCTCGCCTGCCCCGGGGACTCCTGCCTTCTGGGTGTCC
         •               •        •
Cyno   TCACCGCGGTGTCCTCGCCCGCCCCGGGGACGCCTGCCTTCTGGGTGTCC 160       170       180       190       200
Human  GGCTGGCTGGGCCCGCAGCAGTACCTGAGCTACAATAGCCTGCGGGGCGA
                                           • •    •     •
Cyno   GGCTGGCTGGGCCCGCAGCAGTACCTGAGCTACGACAGCCTGAGGGGCCA 210       220       230       240       250
Human  GGCGGAGCCCTGTGGAGCTTGGGTCTGGGAAAACCAGGTGTCCTGGTATT
                                             •
Cyno   GGCGGAGCCCTGTGGAGCTTGGGTCTGGGAAAACCAAGTGTCCTGGTATT 260       270       280       290       300
Human  GGGAGAAAGAGACCACAGATCTGAGGATCAAGGAGAAGCTCTTTCTGGAA Cyno   GGGAGAAAGAGACCACAGATCTGAGGATCAAGGAGAAGCTCTTTCTGGAA 310       320       330       340       350
Human  GCTTTCAAAGCTTTGGGGGGAAAAGGTCCCTACACTCTGCAGGGCCTGCT
                                  •
Cyno   GCTTTCAAAGCTTTGGGGGGAAAAGGCCCCTACACTCTGCAGGGCCTGCT 360       370       380       390       400
Human  GGGCTGTGAACTGGGCCCTGACAACACCTCGGTGCCCACCGCCAAGTTCG
                      •
Cyno   GGGCTGTGAACTGAGCCCTGACAACACCTCGGTGCCCACCGCCAAGTTCG 410       420       430       440       450
Human  CCCTGAACGGCGAGGAGTTCATGAATTTCGACCTCAAGCAGGGCACCTGG Cyno   CCCTGAACGGCGAGGAGTTCATGAATTTCGACCTCAAGCAGGGCACCTGG 460       470       480       490       500
Human  GGTGGGGACTGGCCCGAGGCCCTGGCTATCAGTCAGCGGTGGCAGCAGCA Cyno   GGTGGGGACTGGCCCGAGGCCCTGGCTATCAGTCAGCGGTGGCAGCAGCA 510       520       530       540       550
Human  GGACAAGGCGGCCAACAAGGAGCTCACCTTCCTGCTATTCTCCTGCCCGC
                                                        •
Cyno   GGACAAGGCGGCCAACAAGGAGCTCACCTTCCTGCTATTCTCCTGCCCAC 560       570       580       590       600
Human  ACCGCCTGCGGGAGCACCTGGAGAGGGGCCGCGGAAACCTGGAGTGGAAG
         •
Cyno   ACCGGCTGCGGGAGCACCTGGAGAGGGGCCGTGGAAACCTGGAGTGGAAG 610       620       630       640       650
Human  GAGCCCCCTCCATGCGCCTGAAGGCCCGACCCAGCAGCCCTGGCTTTTC
                                          •   •
Cyno   GAGCCCCCTCCATGCGCCTGAAGGCCCGACCCGGCAACCCTGGCTTTTC 660       670       680       690       700
Human  CGTGCTTACCTGCAGCGCCTTCTCCTTCTACCCTCCGGAGCTGCAACTTC
                                                  •      •
Cyno   CGTGCTTACCTGCAGCGCCTTCTCCTTCTACCCTCCGGAACTGCAACTGC 710       720       730       740       750
Human  GCTTCCTGCGGAATCGGCTGGCCGCTGGCACCGGCCAGGGTGACTTCGGC
                                              •    •    •
Cyno   GGTTCCTGCGGAATCGGGATGGCCGCTGGCACCGGACAGGGCGACTTCGGC
```

TABLE 9-continued

Alignment of Human and Cynomolgus FcRn α-Chain DNA

```
              760        770        780        790        800
Human   CCCAACAGTGACGGATCCTTCCACGCCTCGTCGTCACTAACAGTCAAAAG
                      •
Cyno    CCCAACAGTGACGGCTCCTTCCACGCCTCGTCGTCACTAACAGTCAAAAG 810        820        830        840        850
Human   TGGCGATGAGCACCACTACTGCTGCATTGTGCAGCACGCGGGGCTGGCGC
                                      •
Cyno    TGGCGATGAGCACCACTACTGCTGCATCGTGCAGCACGCGGGGCTGGCGC 860        870        880        890        900
Human   AGCCCCTCAGGGTGGAGCTGGAATCTCCAGCCAAGTCCTCCGTGCTCGTG
                                   •               •
Cyno    AGCCCCTCAGGGTGGAGCTGGAAACTCCAGCCAAGTCCTCGGTGCTCGTG 910        920        930        940        950
Human   GTGGGAATCGTCATCGGTGTCTTGCTACTCACGGCAGCGGCTGTAGGAGG Cyno    GTGGGAATCGTCATCGGTGTCTTGCTACTCACGGCAGCGGCTGTAGGAGG 960        970        980        990       1000
Human   AGCTCTGTTGTGGAGAAGGATGAGGAGTGGGCTGCCAGCCCCTTGGATCT Cyno    AGCTCTGTTGTGGAGAAGGATGAGGAGTGGGCTGCCAGCCCCTTGGATCT 1010       1020       1030       1040       1050
Human   CCCTTCGTGGAGACGACACCGGGGTCCTCCTGCCCACCCCAGGGGAGGCC
             •                     ••          •
Cyno    CCCTCCGTGGAGATGACACCGGGTCCCTCCTGCCCACCCCGGGGAGGCC 1060       1070       1080       1090
Human   CAGGATGCTGATTTGAAGGATGTAAATGTGATTCCAGCCACCGCCTGA
                       •          •        •          •
Cyno    CAGGATGCTGATTCGAAGGATATAAATGTGATCCCAGCCACTGCCTGA
```

The DNA sequence for the human FcRn α-chain has GenBank Accession No. U12255. Story, C. M., Mikulska, J., and Simister, N. E., *A major histocompatibility complex class I-like Fc receptor cloned from human placenta: Possible role in transfer of immunoglobulin G from mother to fetus*, J. Exp. Med. 180, 2377–2381 (1994).

An alignment of the amino acid sequences for human (SEQ ID NO: 10) and cynomolgus (SEQ ID NO: 9) FcγRI α-chain is shown in Table 10. As described previously, the α-chain of FcγRI has various domains, including a signal peptide, three extracellular C-2 Ig like domains, a transmembrane domain and an intracellular domain. The amino acid numbers shown below the amino acids with the symbol Δ are numbered from the start of the mature polypeptide not including the signal sequence. Based on the alignment with the human sequence, the mature cynomolgus FcγRI has an amino acid sequence of residues Δ1 to Δ336 (SEQ ID NO: 65). The n-terminal sequence of cynomologus sequence FcγRI may vary from that shown below. It would be within the skill in the art to express the nucleic acid sequence encoding the cynomologus FcγRI sequence and identify the n-terminal sequence. An extracellular fragment of cynolomolgus FcγRI obtained using the primers of example 1 has an amino acid sequence of Δ1 to Δ269. Any numbers above the amino acid residues represent the numbering of the residues starting at the signal sequence.

Analysis of the % sequence identity shows that the amino acid sequences for human and cynomolgus FcγRI have about 90% identity when the 3' extension is taken into account and about 94% when the 3' extension is not included.

TABLE 10

Alignment of Human and Cynomolgus High-Affinity FcγRI

```
Human     MWFLTTLLLWVPVDGQVDTTK
                •
Cyno      MWFLTALLLNVPVDGQVDTTK Domain 1

Human     AVISLQPPWVSVFQEETVTLHCEVLHLPGSSSTQWFLNGTAT
            •                    •  ••
Cyno      AVITLQPPWVSVFQEETVTLQCEVPRLPGSSSTQWFLNGTAT
          Δ       Δ         Δ         Δ         Δ
          1      10        20        30        40

70        80        90       100
```

TABLE 10-continued

Alignment of Human and Cynomolgus High-Affinity FcγRI

```
Human        QTSTPSYRITSASVNDSGEYRCQRGLSGRSDPIQLEIHR
Cyno         QTSTPSYRITSASVKDSGEYRCQRGPSGRSDPIQLEIHR
                       Δ         Δ         Δ         Δ
                       50        60        70        80
```

Domain 2

```
Human        GWLLLQVSSRVFTEGEPLALRCHAWKDKLVYNVLYYRNGKAFKF
Cyno         DWLLLQVSSRVFTEGEPLALRCHAWKDKLVYNVLYYQNGKAFKF
                       Δ         Δ         Δ         Δ
                       90        100       110       120

150       160       170       180       190
Human        FHWNSNLTILKTNISHNGTYHCSGMGKHRYTSAGISVTVKELFP
Cyno         FYRNSQLTILKTNISHNGAYHCSGMGKHRYTSAGVSVTVKELFP
                       Δ         Δ         Δ         Δ
                       130       140       150       160
```

Domain 3

```
Human        APVLNASVTSPLLEGNLVTLSCETKLLLQRPGLQLYFSFYMGSKTLRG
Cyno         APVLNASVTSPLLEGNLVTLSCETKLLLQRPGLQLYFSFYMGSKTLRG
             Δ         Δ         Δ         Δ         Δ
             170       180       190       200       210

Human        RNTSSEYQILTARREDSGLYWCEAATEDGNVLKRSPELELQVLGLQLP
Cyno         RNTSSEYQILTARREDSGFYWCEATTEDGNVLKRSPELELQVLGLQLP
             Δ         Δ         Δ         Δ         Δ
             220       230       240       250       260
``` transmembrane/
intracellular

```
Human        TPVWFHVLFYLAVGIMFLVNTVLWVTIRKELKRKKKWDLEISLDSGHE
Cyno         TPVWLHVLFYLVVGIMFLVNTVLWVTIRKELKRKKKWNLEISLDSAHE
             Δ         Δ         Δ         Δ         Δ
             270       280       290       300       310

Human        KKVTSSLQEDRHLEEELKCQEQKEEQLQEGVHRKEPQGAT
Cyno         KKVTSSLQEDRHLEEELKSQEQE
             Δ         Δ         Δ         Δ
             320       330       340       350
```

```
Human vs Cyno    335/357 = 93.8% identity
                          without human 3' extension
                 335/374 = 89.6% identity
                          with human 3' extension
```

The amino acid sequence for human FcγRI has Accession Nos.: P12314; P12315; EMBL; X14356; CAA32537.1. EMBL; X14355; CAA32536.1. PIR; S03018. PIR; S03019. PIR; A41357. PIR; B41357. HSSP; P12319; 1ALT. MIM; 146760; -. InterPro; IPR003006; -. Pfam; PF00047; Allen J. M., Seed B., Nucleic Acids Res. 16, 11824–11824, 1988, *Nucleotide sequence of three cDNAs for the human high affinity Fc receptor (FcRI)*; Allen J. M., Seed B., Science 243, 378–381, 1989, *Isolation and expression of functional high-affinity Fc receptor complementary DNAs*.

An alignment of amino acid sequences for human, cynomolgus, and chimp sequences for FcγRIIA (cynomolgus/SEQ ID NO: 15; human/SEQ ID NO: 16; chimp/SEQ ID NO. 17), FcγRIIB (cynomolgus/SEQ ID NO: 18; human/SEQ ID NO: 19), and FcγRIIIA (cynomolgus/ SEQ ID NO: 20; human/SEQ ID NO: 21) is shown in Table 11.

The sequence is divided into domains as described previously: signal peptide, 3 extracellular C-2 like domains, and a transmembrane intracellular domain. In Table 11, the amino acid numbers shown below the amino acids with the symbol Δ are numbered from the start of the mature human polypeptide not including the signal sequence. The mature polypeptides for cynomolgus and chimp FcγRIIA, cynomolgous FcγRIIB, and cynomolgus FcγRIIIA start at the amino acid identified with the asterisk in Table 11 and are separately shown in Tables 21, 22, and 23, and are as follows:

1) cynomolgus FcγRIIA amino acids Δ1 to Δ282 (SEQ ID NO: 66), N terminal sequence TAPPKA (Table 21);
2) chimp FcγRIIA amino Δ1 to Δ249 (SEQ ID NO: 67)(based on alignment with the human sequence);
3) cynomolgus FcγRIIB amino acids Δ1 to Δ252 (SEQ ID NO: 68), N terminal sequence TPAAPP (table 22); and 4) cynomolgus FcγRIIIA amino acids Δ1 to Δ234 (SEQ ID NO: 69), N terminal sequence EDLPKA (table 23).

In table 11, any numbers above the amino acid residues represent the numbering of the residues starting at the signal sequence. The asterisks in the table indicate the start of the n-terminal sequence for cynomologus FcγRIIA, FcγRIIB, and FcγRIIIA.

Extracellular fragments of the Fc receptor polypeptides were obtained using the primers described in example 1. An extracellular fragment of FcγRIIA obtained using the primers of example 1 has an amino acid sequence of Δ1 to Δ182, as shown in table 21. An extracellular fragment of FcγRIIB obtained using the primers of example 1 has an amino acid sequence of Δ1 to Δ184, as shown in Table 22. An extracellular fragment of FcγRIIIA obtained using the primers of example 1 has an amino acid sequence of Δ1 to Δ187, as shown in Table 23.

Analysis of the % sequence identity shows the following:

1) Chimp and human amino acid sequences for FcγRIIA have about 97% identity;
2) Cynomolgus and human amino acid sequences for FcγRIIA have about 87% identity with MAMETQ (possible portion of signal peptide) and 89% identity without MAMETQ in the alignment;
3) Cynomolgus and chimp amino acid sequences for FcγRIIA have about 87% identity including MAMETQ in the alignment and 89% without MAMETQ in the alignment;
4) Cynomolgus and human amino acid sequences for FcγRIIB have about 92% identity; and
5) Cynomolgus and human amino acid sequences for FcγRIIIA have about 91% identity.

TABLE 11

Alignment of Human, Cynomolgus and Chimp Low-Affinity FcγRIIA, FcγRIIB, FcγRIIIA signal peptide

```
                        ******        *                **
IIA-human      ----------MAMETQMSQNVCPRNLWLLQPLTVLLLLASADSQAA
IIA-chimp      ----------MAMETQMSQNVCPRNLWLLQPLTVLLLLASADSQA-
IIA-cyno       ----------------MSQNVCPGNLWLLQPLTVLLLLASADSQT-
                                                            *

IIB-human      MGILSFLPVLATESDWADCKSPQPWGHMLLWTAVLFLAPVAGTPA
IIB-cyno       MGILSFLPVLATESDWADCKSSQPWGHMLLWTAVLFLAPVAGTPA
                                                            *

IIIA-human                         MWQLLLPTALLLLVSAGMRTE
IIIA-cyno                          MWQLLLPTALLLLVSAGMRAE
                                                    Δ   *
                                                    1
```

Domain 1

```
                                  •        • • •   •
IIA-human      APPKAVLKLEPPWINVLQEDSVTLTCQGARSPESDSIQWFHN
IIA-chimp      APPKAVLKLEPPWINVLQEDSVTLTCRGARSPESDSIQWFHN
IIA-cyno       APPKAVLKLEPPWINVLREDSVTLTCGGAHSPDSDSTQWFHN
               Δ        Δ         Δ         Δ         Δ
               1        10        20        30        40

•       •           •• •    •
IIB-human      APPKAVLKLEPQWINVLQEDSVTLTCRGTHSPESDSIQWFHN
IIB-cyno       APPKAVLKLEPPWINVLREDSVTLTCGGAHSPDSDSTQWFHN

•                  •
IIIA-human     DLPKAVVFLEPQWYRVLEKDSVTLKCQGAYSPEDNSTQWFHN
IIIA-cyno      DLPKAVVFLEPQWYRVLEKDRVTLKCQGAYSPEDNSTRWFHN
                        Δ         Δ         Δ         Δ
                        10        20        30        40

•            •
IIA-human      GNLIPTHTQPSYRFKANNNDSGEYTCQTGQTSLSDPVHLTVLSE
IIA-chimp      GNLIPTHTQPSYRFKANNNDSGEYTCQTGQTSLSDPVHLTVLSE
IIA-cyno       GNRIPTHTQPSYRFKANNNDSGEYRCQTGRTSLSDPVHLTVLSE
                        Δ         Δ         Δ         Δ
                        50        60        70        80

•            •
IIB-human      GNLIPTHTQPSYRFKANNNDSGEYTCQTGQTSLSDPVHLTVLSE
IIB-cyno       GNLIPTHTQPSYRFKANNNDSGEYRCQTGRTSLSDPVHLTVLSE

•     •  • ••      •
IIIA-human     ESLISSQASSYFIDAATVDDSGEYRCQTNLSTLSDPVQLEVHIG
IIIA-cyno      ESLISSQTSSYFIAAARVNNSGEYRCQTSLSTLSDPVQLEVHIG
                        Δ         Δ         Δ         Δ
```

TABLE 11-continued

Alignment of Human, Cynomolgus and Chimp Low-Affinity
FcγRIIA, FcγRIIB, FcγRIIIA

```
                     50        60        70        80
Domain 2

•         •         •         •       •••
IIA-human     WLVLQTPHLEFQEGETIMLRCHSWKDKPLVKVTFFQNGKSQKFS
IIA-chimp     WLVLQTPHLEFQEGETIVLRCHSWKDKPLVKVTFFQNGKSQKFS
IIA-cyno      WLALQTPHLEFREGETIMLRCHSWKDKPLIKVTFFQNGIAKKFS
              Δ         Δ         Δ         Δ         Δ
              90       100       110       120       130

•         •         •         •         •
IIB-human     WLVLQTPHLEFQEGETIVLRCHSWKDKPLVKVTFFQNGKSKKFS
IIB-cyno      WLALQTPHLEFREGETILLRCHSWKDKPLIKVTFFQNGISKKFS

••        •
IIIA-human    WLLLQAPRWVFKEEDPIHLRCHSWKNTALHKVTYLQNGKGRKYF
IIIA-cyno     WLLLQAPRWVFKEEESIHLRCHSWKNTLLHKVTYLQNGKGRKYF
              Δ         Δ         Δ         Δ         Δ
              90       100       110       120       130

••       ••                  ••        •
IIA-human     RLDPTFSIPQANHSHSGDYHCTGNIGYTLFSSKPVTITVQV
IIA-chimp     HLDPNLSIPQANHSHSGDYHCTGNIGYTLFSSKPVTITVQA
IIA-cyno      HMDPNFSIPQANHSHSGDYHCTGNIGYTPYSSKPVTITVQV
              Δ         Δ         Δ         Δ         Δ
              131      140       150       160       170

•••                           •         •
IIB-human     RSDPNFSIPQANHSHSGDYHCTGNIGYTLYSSKPVTITVQA
IIB-cyno      HMNPNFSIPQANHSHSGDYHCTGNIGYTPYSSKPVTITVQV

•                    •
IIIA-human    HHNSDFYIPKATLKDSGSYFCRGLFGSKNVSSETVNITITQ
IIIA-cyno     HQNSDFYIPKATLKDSGSYFCRGLIGSKNVSSETVNITITQ
              Δ         Δ         Δ         Δ
              140      150       158       170 transmembrane/
intracellular

•         •       •••
IIA-human     PSMGSSSPMGIIVAVVIATAVAAIVAAVVALIYCRKKRISANSTD
IIA-chimp     PSVGSSSPVGIIVAVVIATAVAAIVAAVVALIYCRKKRISANSTD
IIA-cyno      PSVGSSSPMGIIVAVVTGIAVAAIVAAVVALIYCRKKRISANSTD
              Δ         Δ         Δ         Δ
              180       190       200       210

•••        •
IIB-human     P---SSSPMGIIVAVVTGIAVAAIVAAVVALIYCRKKRISANPTN
IIB-cyno      PSMGSSSPIGIIVAVVTGIAVAAIVAAVVALIYCRKKRISANPTN

•         •                            •    ••   •
IIIA-human    GLAVSTISSFFPPGYQVSFCLVMVLLFAVDTGLYFSVKTNIRSST
IIIA-cyno     DLAVSSISSFFPPGYQVSFCLVMVLLFAVDTGLYFSMKKSIPSST
              Δ         Δ         Δ         Δ
              180       190       200       210

•         •         •         •       ITAM motif
IIA-human     PVKAAQFEPPGRQMIAIRKRQLEETNNDYETADGGYMTLNPRAPT
IIA-chimp     PVKAAQFEPPGRQMIAIRKRQLEETNNDYETADGGYMTLNPRAPT
IIA-cyno      PVKAARFEPLGRQTIALRKRQLEETNNDYETADGGYMTLNPRAPT
              Δ         Δ         Δ         Δ         Δ
              220       230       240       250       260

•
IIB-human     PDEADKVGAENTITYSLLMHPDALEEPDDQNRI
IIB-cyno      PDEADKVGAENTITYSLLMHPDALEEPDDQNRV
                          ITIM motif

•         •
IIIA-human    RDWKDHKFKWRKDPQDK
IIIA-cyno     RDWEDHKFKWSKDPQDK
              Δ         Δ
              220       230
```

TABLE 11-continued

Alignment of Human, Cynomolgus and Chimp Low-Affinity
FcγRIIA, FcγRIIB, FcγRIIIA

```
                          ITAM motif
                          •    •  ••
IIA-human       DDDKNIYLTLPPNDHVNSNN
IIA-chimp       DDDKNIYLTLPPNDHVNSNN
IIA-cyno        DDDRNIYLTLSPNDYDNSNN
                       Δ       Δ
                      270     280
   IIA chimp/human    308/317 = 97.2% identity
       cyno/human     277/317 = 87.4% identity (+MAMETQ)
                      277/311 = 89.1% identity (-MAMETQ)
       cyno/chimp     276/316 = 87.3% identity (+MAMETQ)
                      276/310 = 89.0% identity (-MAMETQ)

IIB  cyno/human    270/294 = 91.8% identity
   IIIA cyno/human    232/254 = 91.3% identity
```

The human amino acid sequence for FcRIIA has the following Accession Nos.: P12318; EMBL; M31932; AAA35827.1. EMBL; Y00644; CAA68672.1. EMBL; J03619; AAA35932.1. EMBL; A21604; CAA01563.1. PIR; A31932. PIR; JL0118. PIR; S02297. PIR; S00477. PIR; S06946. HSSP; P12319; 1ALT. MIM; 146790; -. InterPro; IPR003006; -. Pfam; PF00047. Brooks D. G., Qiu W. Q., Luster A. D., Ravetch J. V., J. Exp. Med. 170, 1369–1385, 1989, *Structure and expression of human IgG FcRII (CD32). Functional heterogeneity is encoded by the alternatively spliced products of multiple genes*; Stuart S. G., Trounstine M. L., Vaux D. J. T., Koch T., Martens C. L., Moore K. W., J. Exp. Med. 166, 1668–1684, 1987, *Isolation and expression of cDNA clones encoding a human receptor for IgG (Fc gamma RII)*; Hibbs M. L., Bonadonna L., Scott B. M., Mckenzie I. F. C., Hogarth P. M., Proc. Natl. Acad. Sci. U.S.A. 85, 2240–2244, 1988, *Molecular cloning of a human immunoglobulin G Fc receptor*; Stengelin S., Stamenkovic I., Seed B., EMBO J. 7, 1053–1059, 1988, *Isolation of cDNAs for two distinct human Fc receptors by ligand affinity cloning*; Salmon J. E., Millard S., Schachter L. A., Arnett F. C., Ginzler E. M., Gourley M. F., Ramsey-Goldman R., Peterson M. G. E., Kimberly R. P., J. Clin. Invest. 97, 1348–1354, 1996, *Fc gamma RIIA alleles are heritable risk factors for lupus nephritis in African Americans.*

The human sequence for FcγRIIB has Accession No. X52473. Engelhardt, W., Geerds, C. and Frey, J., *Distribution, inducibility and biological function of the cloned and expressed human beta Fc receptor II, Eur. J. Immunol.* 20 (6), 1367–1377 (1990).

The human amino acid sequence for FcγRIIIA has Accession Nos.: P08637; EMBL; X52645; CAA36870.1. EMBL; Z46222; CAA86295.1. PIR; JL0107. MIM; 146740; -. InterPro; IPR003006; -. Pfam; PF00047; Ravetch J. V., Perussia B., J. Exp. Med. 170, 481–497, 1989, *Alternative membrane forms of Fc gamma RIII(CD16) on human natural killer cells and neutrophils. Cell type-specific expression of two genes that differ in single nucleotide substitutions*; Gessner J. E., Grussenmeyer T., Kolanus W., Schmidt R. E., J. Biol. Chem. 270, 1350–1361, 1995, *The human low affinity immunoglobulin G Fc receptor III-A and III-B genes: Molecular characterization of the promoter regions*; de Haas M., Koene H. R., Kleijer M., de Vries E., Simsek S., van Tol M. J. D., Roos D., von dem Borne A. E. G. K., J. Immunol. 156, 3948–3955, 1996, *A triallelic Fc gamma receptor type IIIA polymorphism influences the binding of human IgG by NK cell Fc gamma RIIIa*; Koene H. R., Kleijer M., Algra J., Roos D., von dem Borne A. E. G. K., de Haas M., Blood 90, 1109–1114, 1997, *Fc gammaRIIIa-158V/F polymorphism influences the binding of IgG by natural killer cell Fc gammaRIIIa, independently of the Fc gammaRIIIa-48L/R/H phenotype*; Wu J., Edberg J. C., Redecha P. B., Bansal V., Guyre P. M., Coleman K., Salmon J. E., Kimberly R. P., J. Clin. Invest. 100, 1059–1070, 1997, *A novel polymorphism of FcgammaRIIIa (CD16) alters receptor function and predisposes to autoimmune disease.*

TABLE 21

Sequence of Mature FcRIIA

Domain 1

```
TAPPKAVLKLEPPWINVLREDSVTLTCGGAHSPDSDSTQWFHN
Δ          Δ          Δ          Δ          Δ
1          10         20         30         40

GNRIPTHTQPSYRFKANNNDSGEYRCQTGRTSLSDPVHLTVLSE
Δ          Δ          Δ          Δ
50         60         70         80
```

Domain 2

```
WLALQTPHLEFREGETILLRCHSWKDKPLIKVTFFQNGISKKFS
Δ          Δ          Δ          Δ          Δ
90         100        110        120        130

HMNPNFSIPQANHSHSGDYHCTGNIGYTPYSSKPVTITVQV
Δ          Δ          Δ          Δ
140        150        160        170
```

Intracellular/transmembrane domain

```
PSVGSSSPMGIIVAVVTGIAVAAIVAAVVALIYCRKKRISANSTD
Δ          Δ          Δ          Δ
180        190        200        210

ITAM
PVKAARFEPLGRQTIALRKRQLEETNNDYETADGGYMTLNPRAPT
Δ          Δ          Δ          Δ          Δ
220        230        240        250        260

ITAM
DDDRNIYLTLSPNDYDNSNN
    Δ      Δ
    270    280
```

TABLE 22

Sequence of Mature FcγRIIB

Domain 1

```
TPAAPPKAVLKLEPPWINVLREDSVTLTCGGAHSPDSDSTQWFHN
Δ    Δ    Δ    Δ    Δ
1    10   20   30   40

GNLIPTHTQPSYRFKANNNDSGEYRCQTGRTSLSDPVHLTVLSE
    Δ    Δ    Δ    Δ
    50   60   70   80
```

Domain 2

```
WLALQTPHLEFREGETILLRCHSWKDKPLIKVTFFQNGISKKFS
Δ    Δ    Δ    Δ    Δ
90   100  110  120  130

HMNPNFSIPQANHSHSGDYHCTGNIGYTPYSSKPVTITVQV
    Δ    Δ    Δ    Δ
    140  150  160  170
```

Transmembrane/intracellular

```
PSMGSSSPIGIIVAVVTGIAVAAIVAAVVVALIYCRKKRISANPTN
    Δ    Δ    Δ    Δ
    180  190  200  210
```

ITIM motif

```
PDEADKVGAENTITYSLLMHPDALEEPDDQNRV
Δ    Δ    Δ    Δ
220  230  240  250
```

TABLE 23

Sequence for Mature FcγRIIIA

Domain 1

```
EDLPKAVVFLEPQWYRVLEKDRVTLKCQGAYSPEDNSTRWFHN
Δ    Δ    Δ    Δ    Δ
1    10   20   30   40

ESLISSQTSSYFIAAARVNNSGEYRCQTSLSTLSDPVQLEVHIG
    Δ    Δ    Δ    Δ
    50   60   70   80
```

Domain 2

```
WLLLQAPRWVFKEEESIHLRCHSWKNTLLHKVTYLQNGKGRKYF
Δ    Δ    Δ    Δ    Δ
90   100  110  120  130

HQNSDFYIPKATLKDSGSYFCRGLIGSKNVSSETVNITITQ
    Δ    Δ    Δ    Δ
    140  150  160  170
```

Transmembrane/intracellular

```
DLAVSSISSFFPPGYQVSFCLVMVLLFAVDTGLYFSMKKSIPSST
Δ    Δ    Δ    Δ
```

TABLE 23-continued

Sequence for Mature FcγRIIIA

```
         180      190      200      210

RDWEDHKFKWSKDPQDK
    Δ    Δ
    220  230
```

An alignment of the nucleic acid sequence encoding the human (SEQ ID NO: 12) and cynomolgus (SEQ ID NO: 11) gamma chain of FcγRI/III is shown in Table 12.

Analysis of % sequence identity shows that the nucleic acid sequences encoding human and cynomolgus gamma chain FcγRI/III have about 99% identity.

TABLE 12

Alignment of Human and Cynomolgus FcγRI/III

Gamma-Chain

```
            1         10
            |         |
Human    MIPAVVLLLLLLVEQAAA
Cyno     MIPAVVLLLLLLVEQAAA 20        30        40        50
            |         |         |         |
Human    LGEPQLCYILDAILFLYGIVLTLLYCRLKIQV
Cyno     LGEPQLCYILDAILFLYGIVLTLLYCRLKIQV 60        70        80
                       |         |         |
Human    RKAAITSYEKSDGVYTGLSTRNQETYETLKHEKPPQ
              •
Cyno     RKAAIASYEKSDGVYTGLSTRNQETYETLKHEKPPQ
                       ITAM motif  ITAM motif
```

Cyno vs Human = 85/86 = 98.8% identity

An amino acid sequence for human gamma chain has Accession Nos.: P30273; EMBL; M33195; AAA35828.1. EMBL; M33196; -. PIR; A35241. MIM; 147139;-. Kuester H., Thompson H., Kinet J.-P., J. Biol. Chem. 265, 6448–6452, 1990, *Characterization and expression of the gene for the human Fc receptor gamma subunit. Definition of a New Gene Family*

An alignment of the amino acid sequences for human (SEQ ID NO: 26) and cynomolgus (SEQ ID NO: 25) β-2 microglobulin is shown in Table 13. The mature β-2 microglobulin has an amino acid sequence of amino acids Δ1 to Δ99 (SEQ ID NO: 70).

Analysis of the % sequence identity shows that the amino acid sequences for human and cynomolgus β-2 microglobulin have about 92% identity with no deletions or insertions.

TABLE 13

Alignment of Human and Cynomolgus β2-Microglobulin

```
Human   MSRSVALAVLALLSLSGLEA
           •
Cyno    MSPSVALAVLALLSLSGLEA

Human   IQRTPKIQVYSRHPAENGKSNFLNCYVSGFHPSDIEVDLLKNGERIEKVEHSD
              •   •                                •••
Cyno    IQRTPKIQVYSRHPPENGKPNFLNCYVSGFHPSDIEVDLLKNGEKMGKVEHSD
```

TABLE 13-continued

Alignment of Human and Cynomolgus β2-Microglobulin

```
            Δ         Δ         Δ         Δ         Δ         Δ
            1         10        20        30        40        50
Human    LSFSKDWSFYLLYYTEFTPTEKDEYACRVNHVTLSQPKIVKWDRDM
                                ·                   ·  ··
Cyno     LSFSKDWSFYLLYYTEFTPNEKDEYACRVNHVTLSGPRTVKWDRDM
                  Δ         Δ         Δ         Δ
                  60        70        80        90
Cyno vs Human   109/119 = 91.6% identity
```

The human amino acid sequence for β-2 microglobulin has Accession Nos.: P01884; EMBL; M17987; AAA51811.1. EMBL; M17986; AAA51811.1. EMBL; AB021288; BAA35182.1. EMBL; AF072097; AAD48083.1. EMBL; V00567; CAA23830.1. EMBL; M30683; AAA87972.1. EMBL; M30684; AAA88008.1. PIR; A02179. PIR; A28579. PDB; 1HLA. Guessow D., Rein R., Ginjaar I., Hochstenbach F., Seemann G., Kottman A., Ploegh H. L., *The human beta 2-microglobulin gene. Primary structure and definition of the transcriptional unit*, J. Immunol. 139, 3132–3138 (1987); Matsumoto K., Minamitani T., *Human mRNA for beta 2-microglobulin*, Medline: Embl/genbank/ddbj database (1998); Zhao Z., Huang X., Li N., Zhu X., Cao X., *A novel gene from human dendritic cell*, Embl/genbank/ddbj databases (1998); Rosa F., Berissi H., Weissenbach J., Maroteaux L., Fellous M., Revel M., *The beta-2-microglobulin mRNA in human Daudi cells has a mutated initiation codon but is still inducible by interferon*, EMBO J. 2, 239–243 (1983); Suggs S. V., Wallace R. B., Hirose T., Kawashima E. H., Itakura K., *Use of synthetic oligonucleotides as hybridization probes: isolation of cloned cDNA sequences for human beta 2-microglobulin*, Proc. Natl. Acad. Sci. USA 78, 6613–6617 (1981); Cunningham B. A., Wang J. L., Berggard I., Peterson P. A., *The complete amino acid sequence of beta 2-microglobulin*, Biochem. 12, 4811-4822 (1973); Lawlor D. A., Warren E., Ward F. E., Parham P., *Comparison of class I MHC alleles in human and apes*, Immunol. Rev. 113, 147–185 (1990); Bjorkman P. J., Saper M. A., Samraoui B., Bennett W. S., Strominger J. L., Wiley D. C., *Structure of the human class I histocompatibility antigen*, HLA-A2, Nature 329, 506–512 (1987); Saper M. A., Bjorkman P. J., Wiley D. C., *Refined structure of the human histocompatibility antigen HLA-A2 at 2.6A resolution*, J. Mol. Biol. 219, 277–319 (1991); Collins E. J., Garboczi D. N., Karpusas M. N., Wiley D. C., *The three-dimentional structure of a class I major histocompatibility complex molecule missing the alpha 3 domain of the heavy chain*, Proc. Natl. Acad. Sci USA 92, 1218–1221 (1995).

An alignment of the amino acid sequences for human (SEQ ID NO: 30) and cynomolgus FcRn α-chain (SEQ ID NO: 29) is shown in Table 14. Two alleles of cynomolgus FcRn were identified. One sequence is that of SEQ ID NO: 29 and has a serine at position 3 (S3) of the mature polypeptide. Another sequence is SEQ ID NO: 64 has an asparagine at position 3 (N3) in the mature polypeptide. The mature polypeptide of FcRnS3 α-chain has a sequence of amino acids Δ1 to Δ342 (SEQ ID NO: 71). The mature polypeptide of FcRnN3 α-chain has a sequence of Δ1 to Δ342 (SEQ ID NO: 72). An extracellular fragment of the FcRnprepared by the method of example 1, has an amino acid sequence of Δ1 to Δ274.

Analysis of the % sequence identity shows that the amino acid sequences for human and cynomolgus FcRn have about 97% identity with no deletions or insertions.

TABLE 14

Alignment of Human and Cynomolgus FcRn α-Chain

```
354/365 = 97% identity
Signal
Cyno    MRVPRPQPWALGLLLFLLPGSLG
            ·
Human   MGVPRPQPWALGLLLFLLPGSLG Extracellular
Domain Cyno         AESHLSLLYHLTAVSSPAPGTPAFWVSGWLGPQQYLSYDSLRGQAEPCGA
CynoN3          N
                                                         ·   ·
Human        AESHLSLLYHLTAVSSPAPGTPAFWVSGWLGPQQYLSYNSLRGEAEPCGA
                      Δ         Δ         Δ         Δ         Δ
                      10        20        30        40        50

Cyno         WVWENQVSWYWEKETTDLRIKEKLFLEAFKALGGKGPYTLQGLLGCELSP
                                                                 ·
Human        WVWENQVSWYWEKETTDLRIKEKLFLEAFKALGGKGPYTLQGLLGCELGP
                      Δ         Δ         Δ         Δ         Δ
                      60        70        80        90        100

Cyno         DNTSVPTAKFALNGEEFMNFDLKQGTWGGDWPEALAISQRWQQQDKAANK
Human        DNTSVPTAKFALNGEEFMNFDLKQGTWGGDWPEALAISQRWQQQDKAANK
                      Δ         Δ         Δ         Δ         Δ
```

TABLE 14-continued

Alignment of Human and Cynomolgus FcRn α-Chain

```
                 110         120         130         140         150
Cyno     ELTFLLFSCPHRLREHLERGRGNLEWKEPPSMRLKARPGNPGFSVLTCSA
                                                   ..
Human    ELTFLLFSCPHRLREHLERGRGNLEWKEPPSMRLKARPSSPGFSVLTCSA
              Δ           Δ           Δ           Δ           Δ
             160         170         180         190         200

Cyno     FSFYPPELQLRFLPNGMAAGTGQGDFGPNSDGSFHASSSLTVKSGDEHHY
                          .
Human    FSFYPPELQLRFLRNGLAAGTGQGDFGPNSDGSFHASSSLTVKSGDEHHY
              Δ           Δ           Δ           Δ           Δ
             210         220         230         240         250

Cyno     CCIVQHAGLAQPLRVELETPAKSS
                            .
Human    CCIVQHAGLAQPLRVELESPAKSS
              Δ           Δ
             260         270
```

Transmembrane/
Intracellular

```
Cyno     VLVVGIVIGVLLLTAAAVGGALLWRRMRSGLPAPWISLRGDDTGSLLPTP
                                                    .
Human    VLVVGIVIGVLLLTAAAVGGALLWRRMRSGLPAPWISLRGDDTGVLLPTP
              Δ           Δ           Δ           Δ           Δ
             280         290         300         310         320

Cyno     GEAQDADSKDINVIPATA
                .  .
Human    GEAQDADLKDVNVIPATA
              Δ           Δ
             330         340
```

The human amino acid sequence for FcRn has Accession No.: U12255. Story C. M., Mikulska J., Simister N. E., A major histocompatibility complex class I-like Fc receptor cloned from human placenta: Possible role in transfer of immunoglobulin G from mother to fetus, Exp. Med. 180, 2377–2381 (1994).

Example 3

Cynomolgus FcγRI And Human FcγRI Bind Human IgG Subclasses Equivalently

Materials and Methods

Human IgG2, IgG3, and IgG4 isotypes of E27 (IgG1) were constructed by subcloning the appropriate heavy chain Fc cDNA from a human spleen cDNA library into a pRK vector containing the E27 variable heavy domain. All IgG subclasses and variants were expressed using the same E27 κ light chain as described in Shields, R. L., Namenuk, A. K., Hong, K., Meng, Y. G., Rae, J., Briggs, J., Xie, D., Lai, J., Stadlen, A., Li, B., Fox, J. A., and Presta, L. G. (2001) *J. Biol. Chem.* 276:6591–6604 or U.S. Pat. No. 6,194,551.

Following cotransfection of heavy and light chain plasmids into 293 cells, IgG 1, IgG2, IgG4 and variants were purified by protein A chromatography. IgG3 was purified using protein G chromatography. All protein preparations were analyzed using a combination of SDS-polyacrylamide gel electrophoresis, ELISA, and spectroscopy.

The cDNA for Human FcγRI was isolated by reverse transcriptase-PCR (GeneAmp, PerkinElmer Life Sciences) of oligo(dT)-primed RNA from U937 cells using primers that generated a fragment encoding the α-chain extracellular domain. Human FcγR extracellular domains bound to Gly/6-His/GST fusions were prepared as described in Shields, R. L., Namenuk, A. K., Hong, K., Meng, Y. G., Rae, J., Briggs, J., Xie, D., Lai, J., Stadlen, A., Li, B., Fox, J. A., and Presta, L. G. (2001) *J. Biol. Chem.* 276:6591-6604 or U.S. Pat. No. 6,194,551. The cDNA was subcloned into previously described pRK mammalian cell expression vectors, as described in Eaton et al., 1986, *Biochemistry*, 25:8343–8347. The cDNA for cynomolgus FcγRI was isolated as described in Example 1.

To facilitate the purification of the expressed human and cynomologus FcγRI, the transmembrane domain and intracellular domain of each were replaced by DNA encoding a Gly-His$_6$ tag and human glutathione S-transferase (GST). The GST sequence was obtained by PCR from the pGEX-4T2 plasmid (Amersham Pharmacia Biotech) with NheI and XbaI restriction sites at the 5' and 3' ends, respectively. The expressed FcγRI contained the extracellular domains of the α-chain fused at His271 to Gly/His$_6$/GST. Primers used to subclone the extracellular portion of the cynomolgus FcγRI α-chain are shown in Table 1.

The cynomolgus and human FcγRI plasmids were transfected into human embryonic kidney 293 cells by calcium phosphate precipitation (Gorman, C. M., Gies, D. R., and McCray, G. (1990) DNA Prot. Engineer. Tech. 2, 3–10). Supernatants were collected 72 hours after conversion to serum-free PSO$_4$ medium supplemented with 10 mg/liter recombinant bovine insulin, 1 mg/liter human transferrin, and trace elements. Proteins were purified by nickel-nitrilotriacetic acid chromatography (Qiagen, Valencia, Calif.). Purified protein was analyzed through a combination of 4–20% SDS-polyacrylamide gel electrophoresis, ELISA, and amino acid analysis.

Standard enzyme-linked immunoabsorbent assays (ELISA) were performed in order to detect and quantify interactions between cynomologus FcγRI or human FcγRI and human IgG1, IgG2, IgG3, or IgG4 (Table 15). ELISA plates (Nunc) were coated with 150 ng/well by adding 100 μL of 1.5 μg/ml stock solution cynomologus FcγRI or human FcγRI in PBS for 48 hours at 4° C. After washing plates five times with wash buffer, (PBS, pH 7.4 containing 0.5% Tween-20), plates were blocked with 250 μL of assay buffer (50 mM Tris-buffered saline, 0.05% Tween-20, 0.5% RIA-grade bovine serum albumin, 2 mM EDTA, pH 7.4) at 25° C. for 1 hours. Plates were washed five times with wash buffer.

Serial 3-fold dilutions of monomeric antibody (10.0–0.0045 μg/ml) were added to plates and incubated for 2 hours. After washing plates five times with assay buffer, the detection reagent was added. Several different horseradish peroxidase (HRP)-conjugated reagents were used to detect the IgG-FcγRI interaction, including: HRP-Protein G (Bio-Rad), goat HRP-anti-human IgG (Boehringer-Mannheim, Indianapolis, Ind.), and murine HRP-anti-human Kappa light chain. After incubation with detecting reagent at 25° C. for 90 minutes, plates were washed five times with wash buffer and 100 μl of 0.4 mg/ml o-phenylenediamine dihydrochloride (Sigma, St. Louis, Mo.) was added. Absorbance at 490 nm was read using a Vmax plate reader (Molecular Devices, Mountain View, Calif.). Note that values reported in Table 15 are the mean±deviation relative to binding of human IgG1 at an IgG1 concentration of 0.370 μg/ml. Titration plots for human IgG using murine HRP-anti-human Kappa light chain as detecting reagent are shown for cynomolgus FcγRI (FIG. 1B) and human FcγRI (FIG. 1A).

Results and Discussion

As illustrated in Table 15, the pattern of binding of cynomolgus FcγRI and human FcγRI to the four human IgG subclasses was similar, regardless of the detection reagent. In each case, human or cynomolgus showed the highest level of binding to IgG3 and the lowest level of binding to IgG2. In particular, the pattern for both human and cynomolgus receptor-IgG interaction was IgG3≧IgG1>IgG4>>>IgG2. Note that the data from the human FcγRI-IgG binding interactions corresponds to data previously reported. Gessner et al, 1998, *Ann. Hematol.* 76:231–248; Deo et al., 1997, *Immunology Today* 18:127–135; Van de Winkel, 1993, *Immunology Today* 14:215–221.

TABLE 15

Binding of monomeric human IgG subclasses to cynomolgus and human FcγRI[a]

| Subclass | Cynomolgus FcγRI | | | Human FcγRI |
|---|---|---|---|---|
| | ProtG[b] | anti-huIgG | anti-kappa | ProtG |
| E27IgG1 | 1.00 | 1.00 | 1.00 | 1.00 |
| E27IgG2 | 0.13 ± 0.04 | 0.04, 0.04 | 0.11, 0.14 | 0.08, 0.08 |
| E27IgG3 | 1.01 ± 0.06 | 1.22, 1.15 | 1.32, 1.37 | 1.14, 1.03 |
| E27IgG4 | 0.52 ± 0.04 | 0.44, 0.45 | 0.60, 0.63 | 0.27, 0.27 |

[a]Detection reagents were HRP-conjugated Protein G (ProtG), HRP-conjugated murine anti-human IgG, heavy chain specific (anti-huIgG), or HRP-conjugated murine anti-human kappa light chain (anti-kappa). Values are the ratio of $OD_{490\ nm}$ (E27IgG subclass) to $OD_{490\ nm}$ (E27IgG1) at 0.37 μg/ml.
[b]Mean ± S.D., n = 4.

Figure 1B:
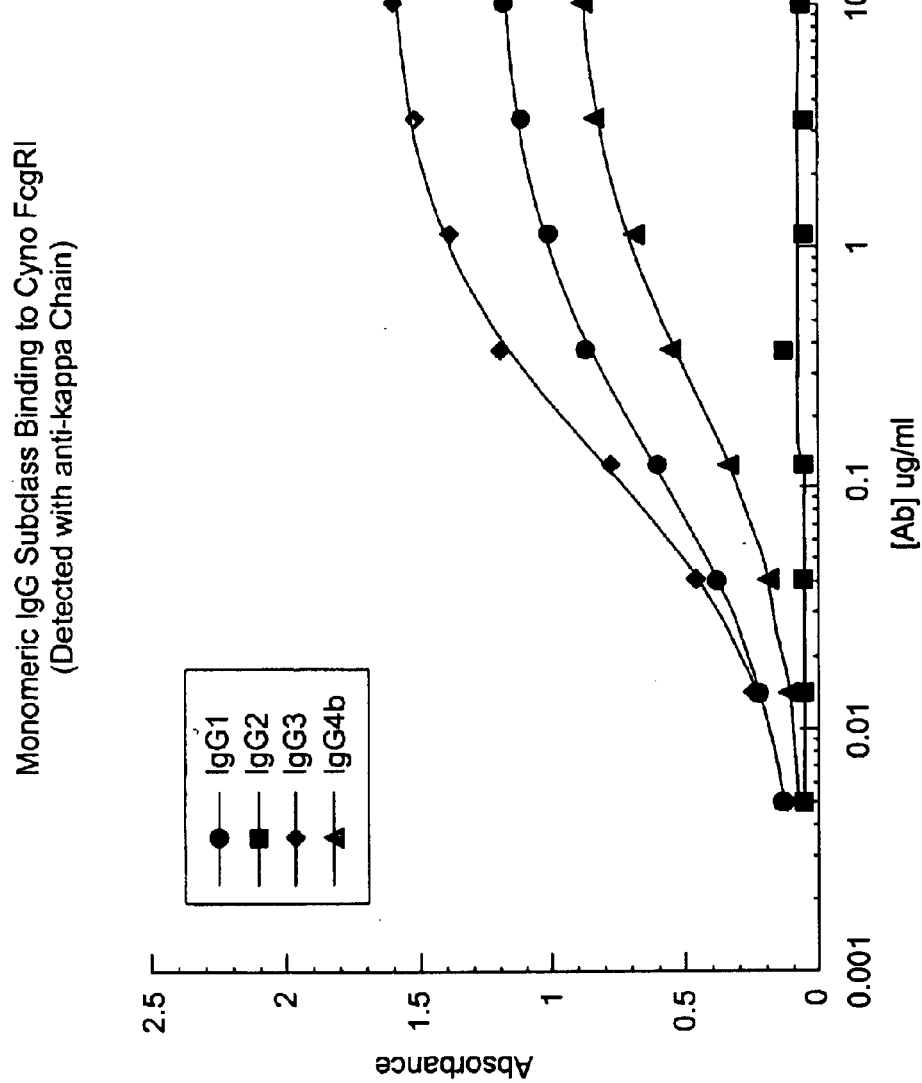

As illustrated in FIGS. 1A and 1B, binding affinity of the human and cynomolgus FcγRI is similar for each of the tested IgG subclasses. In both cases, human and cynomolgus receptors showed a markedly higher affinity for IgG3 and IgG1 as compared to the IgG4 and IgG2. FIG 1A and 1B also shows that the IgG subclass binding to FcγRI is concentration-dependent and saturable.

This data illustrates that cynomolgus FcγRI can replace human FcγRI in the detection of IgG subclasses as human and cynomolgus reveal similar binding patterns of interaction with similar affinities for each IgG subclass.

Example 4

Cynomolgus FcγRIIA Binds Human IgG2

Materials and Methods

ELISA assays analyzing human IgG subclass binding to cynomolgus FcγRIIA were performed using essentially the methods as described in Example 3. However, because FcγRIIA is a low-affinity FcγR, hexameric complexes of each human IgG subclass was formed prior to addition to the Fc receptor. Hexameric complexes were formed by mixing the human IgG subclass with a human IgG at a 1:1 molar ratio. Liu, J., Lester, P., Builder, S., and Shire, S. J. (1995) *Biochemistry* 34:10474–10482. Preparation of the hexameric complexes and their use in FcγRII and FcγRIII assays were as described in Shields, R. L., Namenuk, A. K., Hong, K., Meng, Y. G., Rae, J., Briggs, J., Xie, D., Lai, J., Stadlen, A., Li, B., Fox, J. A., and Presta, L. G. (2001) *J. Biol. Chem.* 276:6591–6604. A plasmid encoding human FcγRIIA(R131) can be readily prepared using the sequence information as described in GenBank or other published sources and see Warmerdam et al., 1991 *J. of Immunology* 147:1338–1343 and Clark et al., 1991 *J of Immunology* 21:1911–1916.

Results and Discussion

As illustrated by Table 16, the pattern of cynomolgus FcγRIIA binding to hexameric complexes of the human IgG subclasses was IgG3=IgG2>IgG1>IgG4. Previous analysis of human IgG subclass binding to the two polymorphic human FcγRIIA forms showed the pattern: human FcγRIIA (R131)—IgG3≧IgG1>>IgG2≧IgG4 and FcγRIIA (H131)—IgG3≧IgG1=IgG2>>>IgG4. Gessner et al, 1998, *Ann. Hematol.* 76:231–248; Deo et al., 1997, *Immunology Today* 18:127–135; Van de Winkel, 1993, *Immunology Today* 14:215–221. These binding patterns show that cynomolgus FcγRIIA, which has a histidine at amino acid 131, is comparable to the human FcγRIIA(H131), both of which bind human IgG2. In contrast, human FcγRIIA(R131) has been reported to bind human IgG2 poorly. Note also that cynomolgus FcγRIIA binds human IgG2 as efficiently as it binds human IgG3, a difference from the human FcγRIIA(H 131) receptor.

TABLE 16

Binding of hexameric complexes of human IgG subclasses to cynomolgus and human FcγRIIA[a]

| Subclass | ProtG | anti-huIgG | anti-kappa |
|---|---|---|---|
| | Cynomolgus FcγRIIA | | |
| E27IgG1 | 1.00 | 1.00 | 1.00 |
| E27IgG2 | 2.11 | 1.27 | 2.20 ± 0.93[b] |
| E27IgG3 | 1.10 | 1.56 | 2.44 ± 0.47 |
| E27IgG4 | 0.12 | 0.12 | 0.42 ± 0.18 |
| | Human FcγRIIA(H131) | | |
| E27IgG1 | 1.00 | 1.00 | 1.00 |
| E27IgG2 | 0.95 | 0.83 | 0.84 |
| E27IgG3 | 0.78 | 1.03 | 0.98 |
| E27IgG4 | 0.25 | 0.47 | 0.19 |
| | Human FcγRIIA(R131) | | |
| E27IgG1 | 1.00 | 1.00 | 1.00 |
| E27IgG2 | 0.63 | 0.40 | 0.47 |

TABLE 16-continued

Binding of hexameric complexes of human IgG subclasses to cynomolgus and human FcγRIIA[a]

| Subclass | ProtG | anti-huIgG | anti-kappa |
|---|---|---|---|
| E27IgG3 | 1.17 | 1.14 | 0.85 |
| E27IgG4 | 0.59 | 0.44 | 0.27 |

[a]Detection reagents were HRP-conjugated Protein G (ProtG), HRP-conjugated murine anti-human IgG, heavy chain specific (anti-huIgG), or HRP-conjugated murine anti-human kappa light chain (anti-kappa). Values are the ratio of $OD_{490\ nm}$ (E27IgG subclass) to $OD_{490\ nm}$ (E27IgG1) at 0.123 µg/ml.
[b]Mean ± SD, n = 3.

Figure 2:
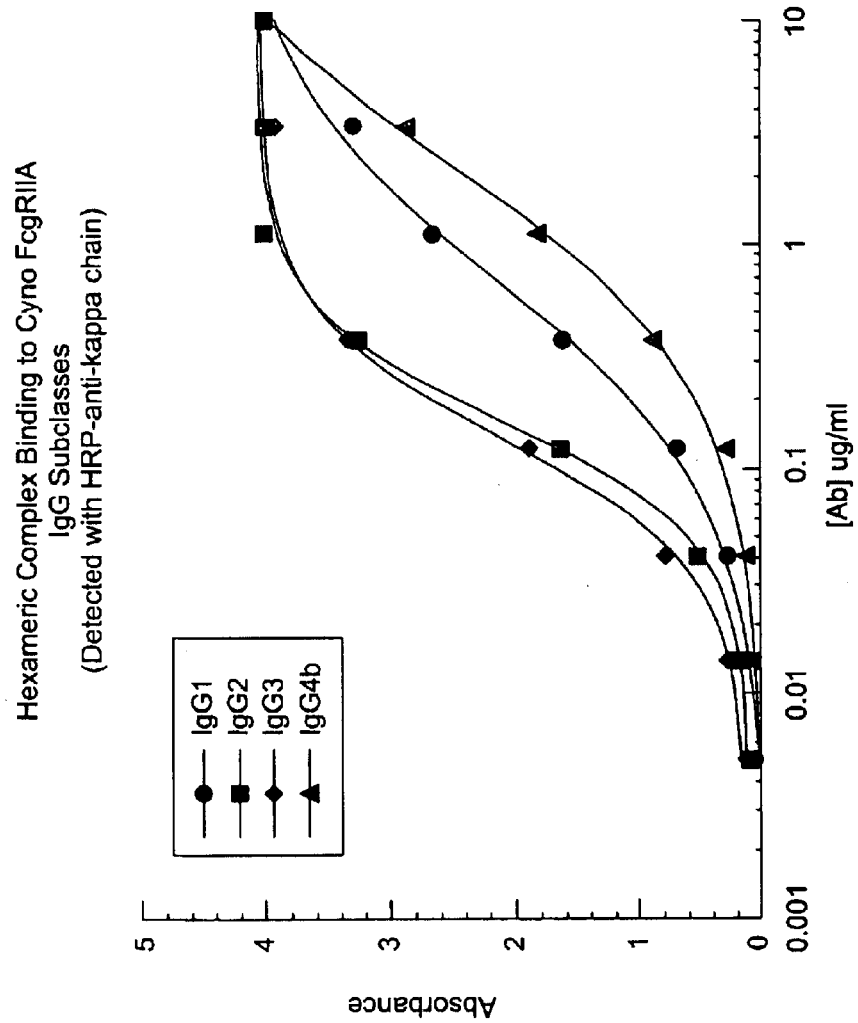

The binding of cynomolgus FcγRIIA to each IgG subclass generally increased as the concentration of each antibody subclass increased (FIG. 2).

The data from table 16 and FIG. 2 illustrates that cynomolgus FcγRIIA binds human IgG2 and IgG3 with high efficiency and may be a preferable agent for use in detecting these human subclasses to either of the two human polymorphic forms of FcγRIIA.

Example 5

Cynomolgus FcγRIIB Binds Human IgG2

Materials and Methods

The methods used to detect FcγRIIB binding to human IgG subclasses was essentially as shown in Examples 3 and 4. Plasmid encoding human FcγRIIB is known and readily obtainable by those of skill in the art and see Kurucz et al., 2000, *Immunol Lett* 75(1):33–40. Data reported in Table 17 represent the mean±deviation relative to binding of human IgG1 at an IgG1 concentration of 0.370 µg/ml.

Results and Discussion

Figure 3A:
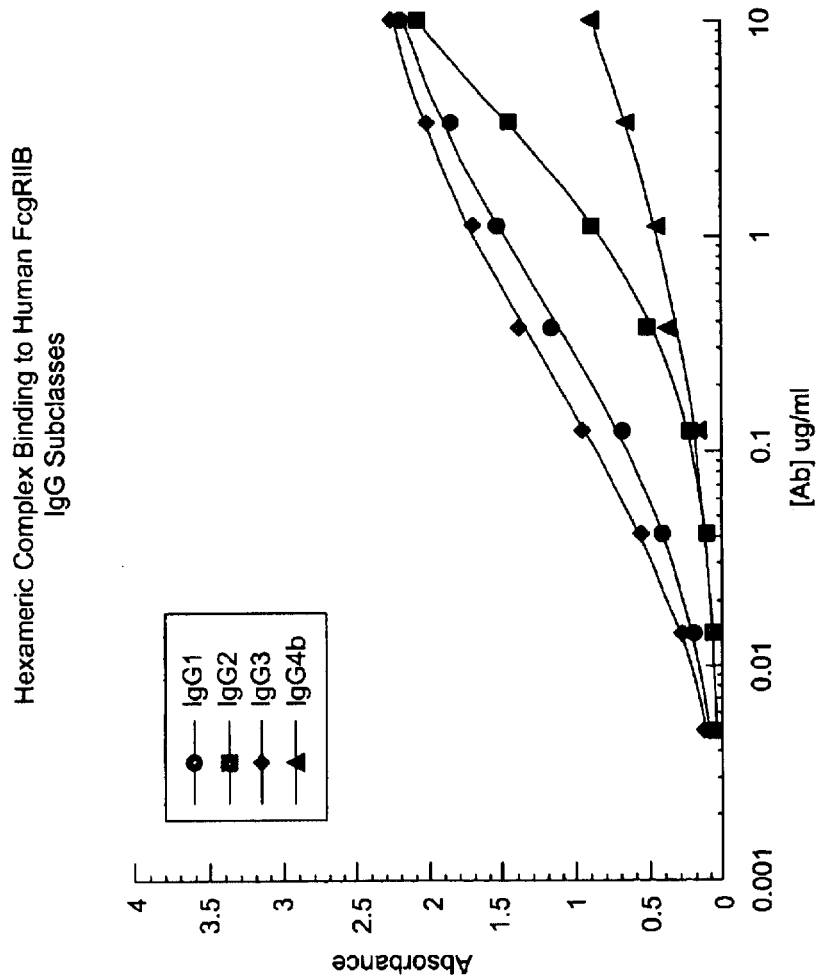
Figure 3B:
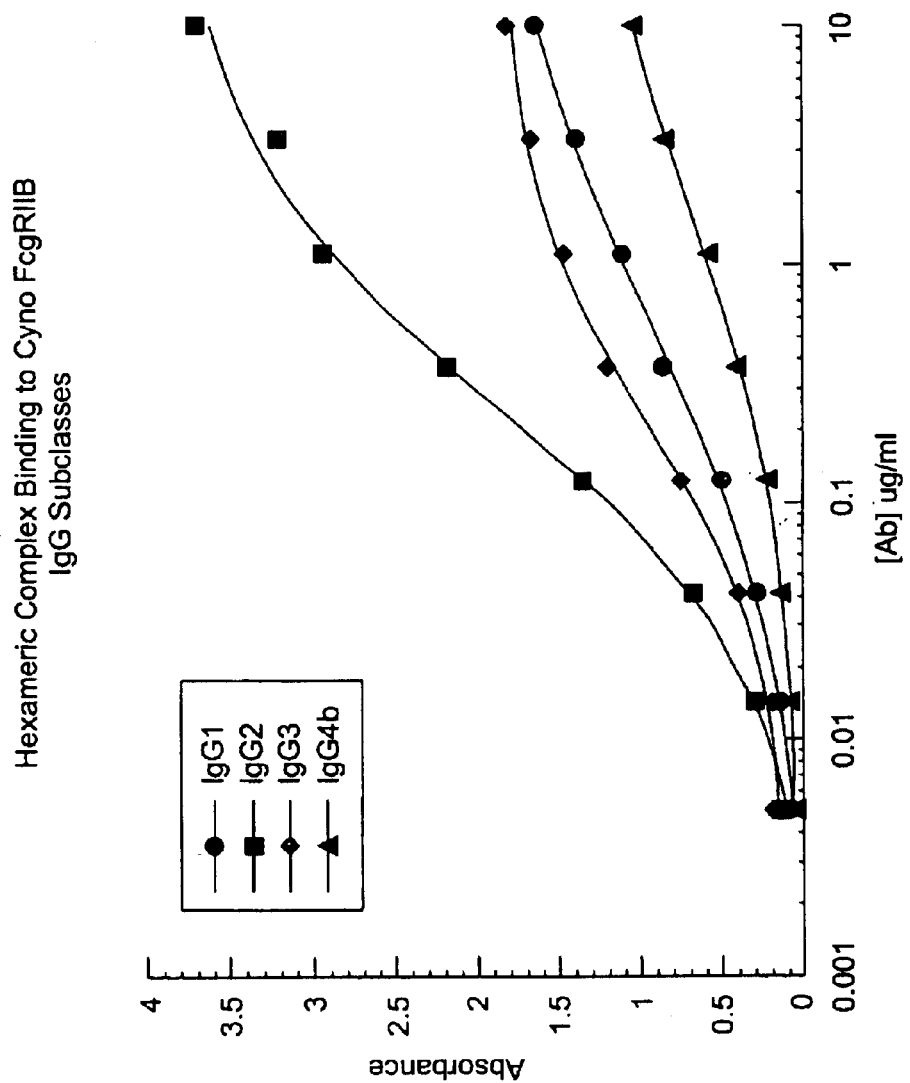

Table 17 illustrates the binding of hexameric complexes of the human IgG subclasses to human and cynomolgus FcγRIIB. The binding pattern between the IgG subclasses and human FcγRIIB is IgG3≧IgG1>IgG2>IgG4 and between the IgG subclasses and cynomolgus FcγRIIB is IgG2≧IgG3>IgG1>IgG4. This binding pattern was the same for both human (FIG. 3A) and cynomolgus (FIG. 3B) over a range of IgG concentrations.

This data illustrates that cynomolgus FcγRIIB has a stronger binding affinity for IgG2 than does human FcγRIIB.

TABLE 17

Binding of Hexameric Complexes of Human IgG Subclasses to Cynomolgus and Human FcγRIIB

| | Cynomolgus FcγRIIB | | | Human FcγRIIB |
|---|---|---|---|---|
| Subclass | ProtG[b] | anti-huIgG[c] | anti-kappa[d] | ProtG[d] |
| E27IgG1 | 1.00 | 1.00 | 1.00 | 1.00 |
| E27IgG2 | 1.89 ± 0.37 | 1.26 ± 0.15 | 2.73 ± 1.00 | 0.43 ± 0.10 |
| E27IgG3 | 1.25 ± 0.17 | 1.69 ± 0.20 | 2.99 ± 1.26 | 1.03 ± 0.13 |
| E27IgG4 | 0.48 ± 0.11 | 0.58 ± 0.16 | 0.64 ± 0.21 | 0.23 ± 0.08 |

[a]Detection reagents were HRP-conjugated Protein G (ProtG), HRP-conjugated murine anti-human IgG, heavy chain specific (anti-huIgG), or HRP-conjugated murine anti-human kappa light chain (anti-kappa). Values are the ratio of $OD_{490\ nm}$ (E27IgG subclass) to $OD_{490\ nm}$ (E27IgG1) at 0.37 µg/ml.
[b]Mean ± SD, n = 8.
[c]Mean ± SD, n = 5.
[d]Mean ± SD, n = 3.

Example 6

Cynomolgus FcγRIIIA and Human FcγRIIIA-V158 Exhibit Equivalent Binding to Human IgG Subclasses Materials and Methods The methods used to detect FcγRIIIA binding to human IgG subclasses was essentially as shown in Examples 3 and 4. As described previously, a human DNA sequence for FcγRIIA α-chain is known and readily obtainable by those of skill in the art. Data reported in Table 18 represents the mean±deviation relative to binding of human IgG1 at an IgG1 concentration of 0.370 µg/ml.

Results and Discussion

Figure 4A:
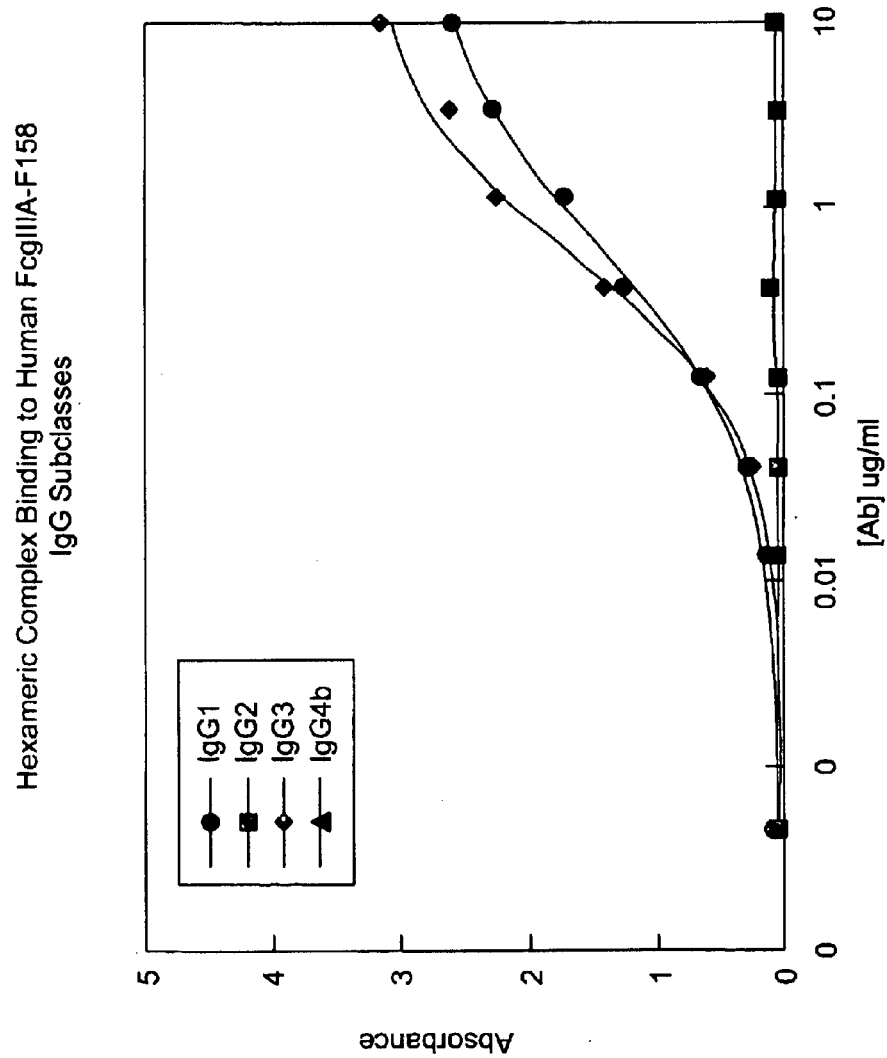
Figure 4B:
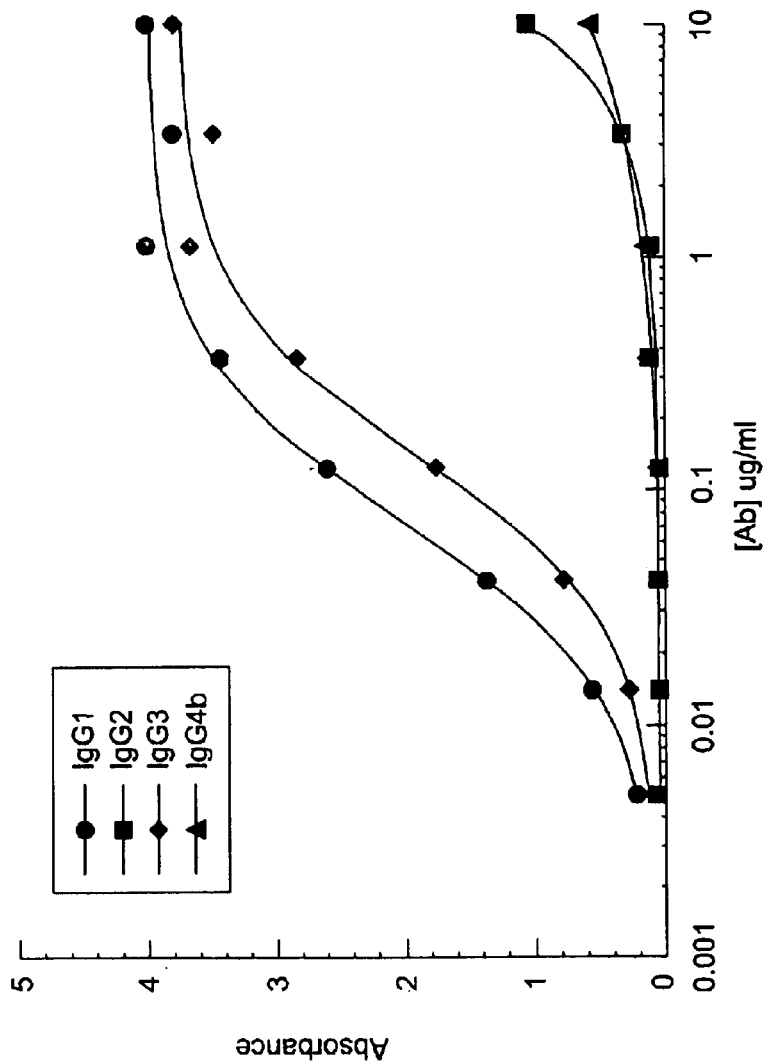
Figure 4C:
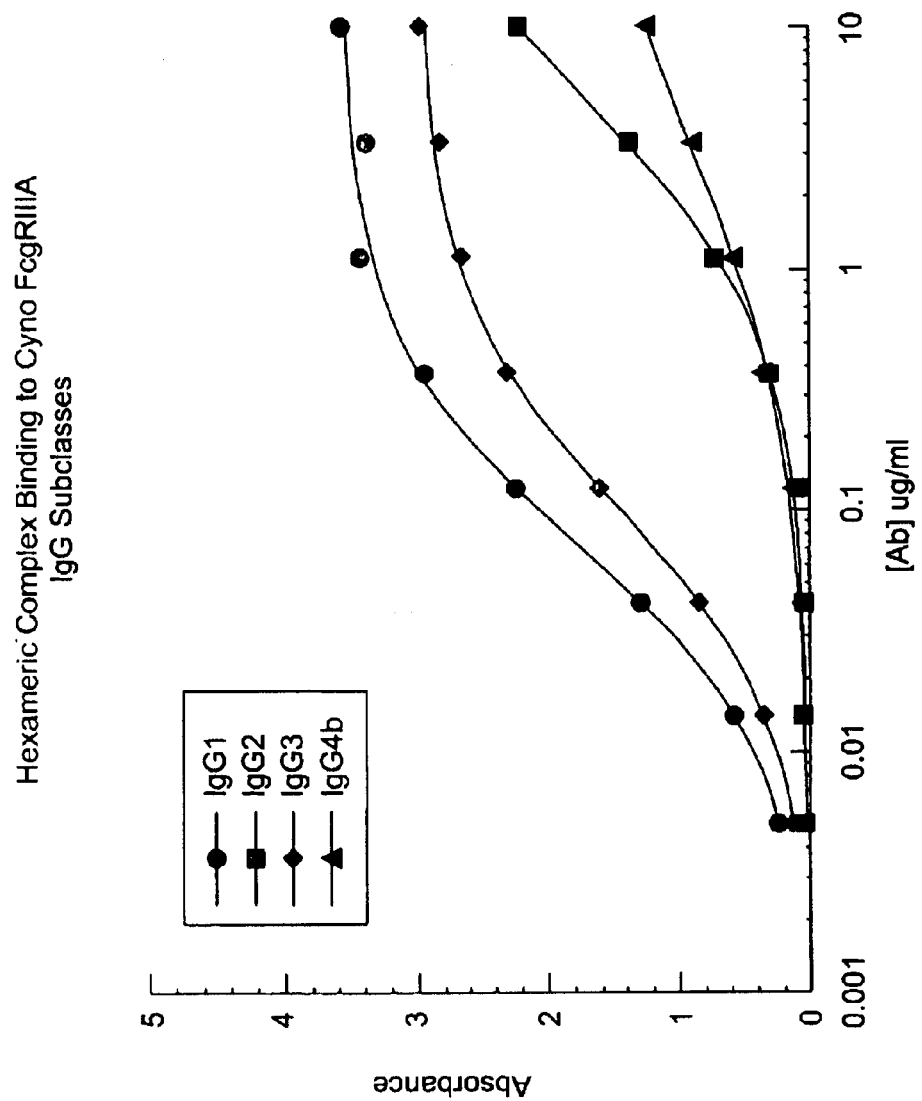

As illustrated in Table 18, cynomolgus FcγRIIIA and human FcγRIIIA-V158 both bind human IgG subclasses with essentially the same pattern, IgG1>IgG3>>IgG2≧IgG4, as compared to human FcγRIIIA-F158, which binds with the pattern, IgG3=IgG1>>>IgG2=IgG4. The human FcγRIIIA-F158-human IgG subclass binding data is in agreement with previous reports. Gessner et al, 1998, *Ann. Hematol.* 76:231–248; Deo et al., 1997, *Immunology Today* 18:127–135; Van de Winkel, 1993, *Immunology Today* 14:215–221. FIGS. 4A, 4B, and 4C illustrate the binding pattern for human FcγRIIIA-F158, human FcγRIIIA-V158, and cynomolgus FcγRIIIA, respectively, for increasing concentrations of each IgG subclass and indicate that the binding interactions are specific and concentration dependent and saturable.

The data illustrates that cynomolgus FcγRIIIA and human FcγRIIIA-V 158 have equivalent binding interactions with the human IgG subclasses, and in particular that cynomolgus FcγRIIIA has preferred binding to the IgG2 subclass as compared to the human FcγRIIIA.

TABLE 18

Binding of Hexameric Complexes of Human IgG Subclasses to Cynomolgus and Human FcγRIIIA

| Subclass | Cynomolgus[b] | Human(F158)[c] | Human(V158)[c] |
|---|---|---|---|
| E27IgG1 | 1.00 | 1.00 | 1.00 |
| E27IgG2 | 0.11 ± 0.02 | 0.06, 0.13 | 0.06, 0.03 |
| E27IgG3 | 0.82 ± 0.08 | 0.75, 0.82 | 0.79, 0.82 |
| E27IgG4 | 0.15 ± 0.04 | 0.06, 0.11 | 0.06, 0.04 |

[a]Detection reagent was HRP-conjugated Protein G. Values are the ratio of $OD_{490\ nm}$ (E27IgG subclass) to $OD_{490\ nm}$ (E27IgG1) at 0.37 µg/ml for cynomolgus FcγRIIIA and human FcγRIIIA(V158) and 1.11 µg/ml for human FcγRIIIA(F158).
[b]Mean ± SD, n = 4.
[c]Human(F158) and Human(V158) are polymorphic forms of human FcγRIIIA with phenylalanine or valine at receptor position 158.

Example 7

Cynomolgus FcγRIIA Binds Human IgG1 Variants S298A and S298A/E333A/K334A

Materials and Methods

Site-directed mutagenesis on E27 IgG1 was essentially as described in Shields et al., 2001, *J. Biol. Chem.*, 276:6591–6604. Briefly, site-directed mutagenesis was used to generate IgG1 variants in which a number of solvent-exposed residues in the CH2 and CH3 domains were individually altered to alanine. The alanine variants were D265A, S298A, S37A, R292A, D280A and S298A/E333A.

ELISA reactions were essentially as described in Examples 3–6, where IgG variants were incubated with the Fc receptors, rather than native IgG protein. Note that for the values provided in Table 19, human receptors are (Absorbance Variant/Absorbance Native IgG1) at 1 μg/ml and for cynomolgus receptors, values are (Absorbance Variant/Absorbance Native IgG1) at 0.370 μg/ml.

Results and Discussion

Figure 5:
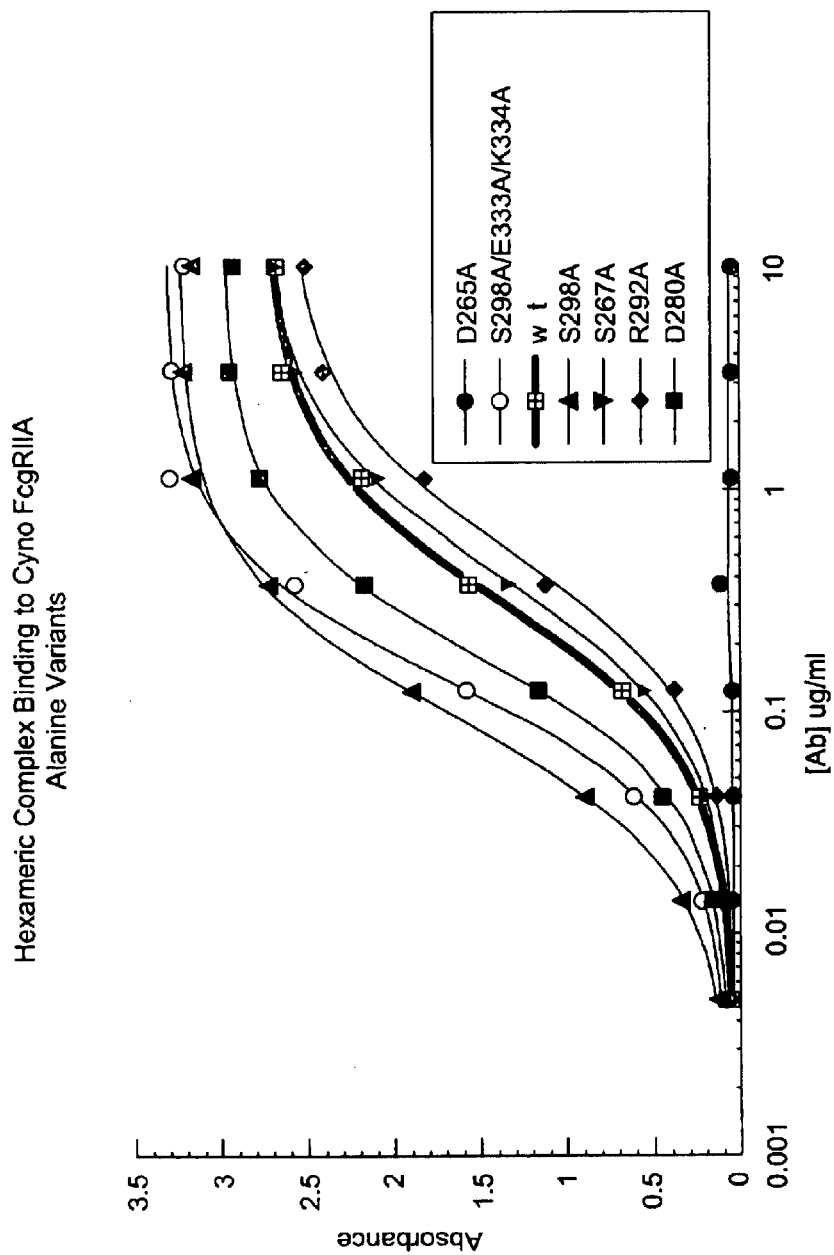
Figure 6:
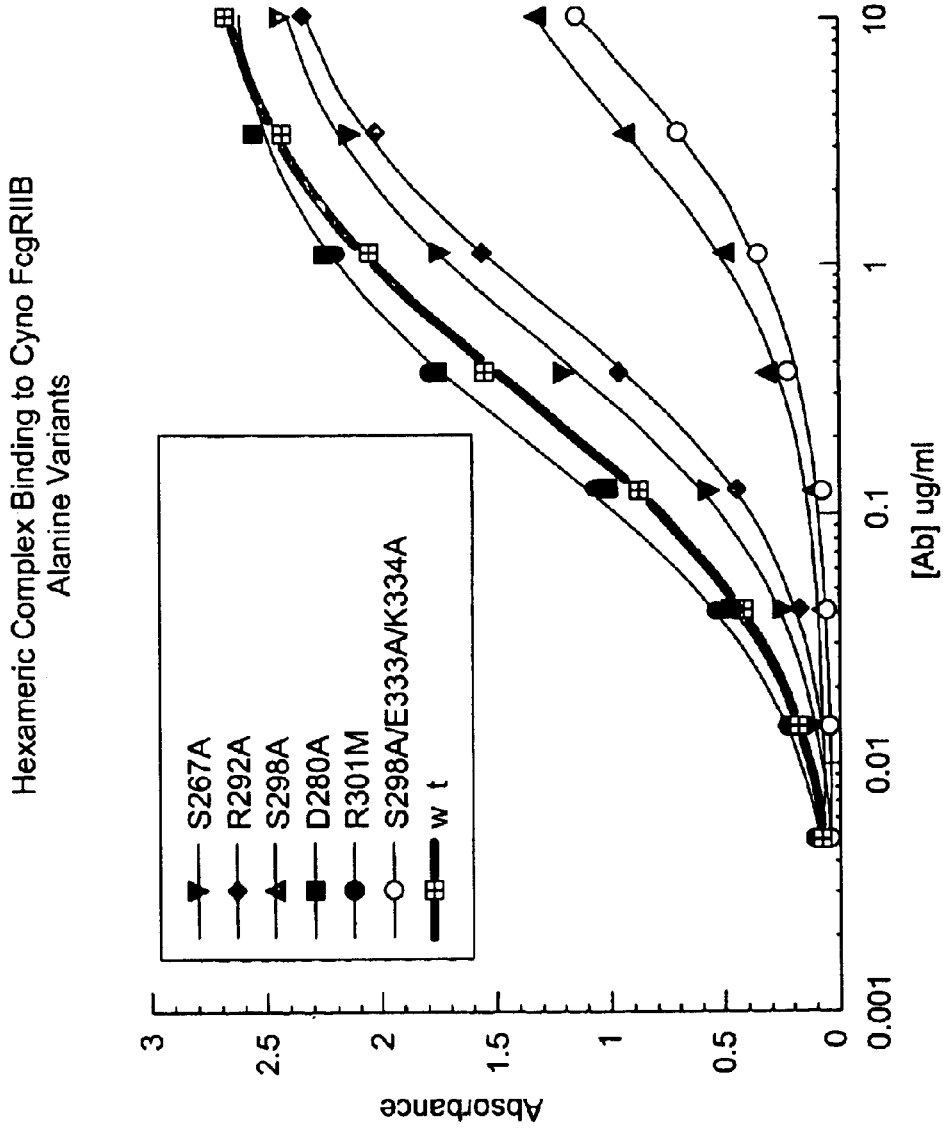
Figure 7:
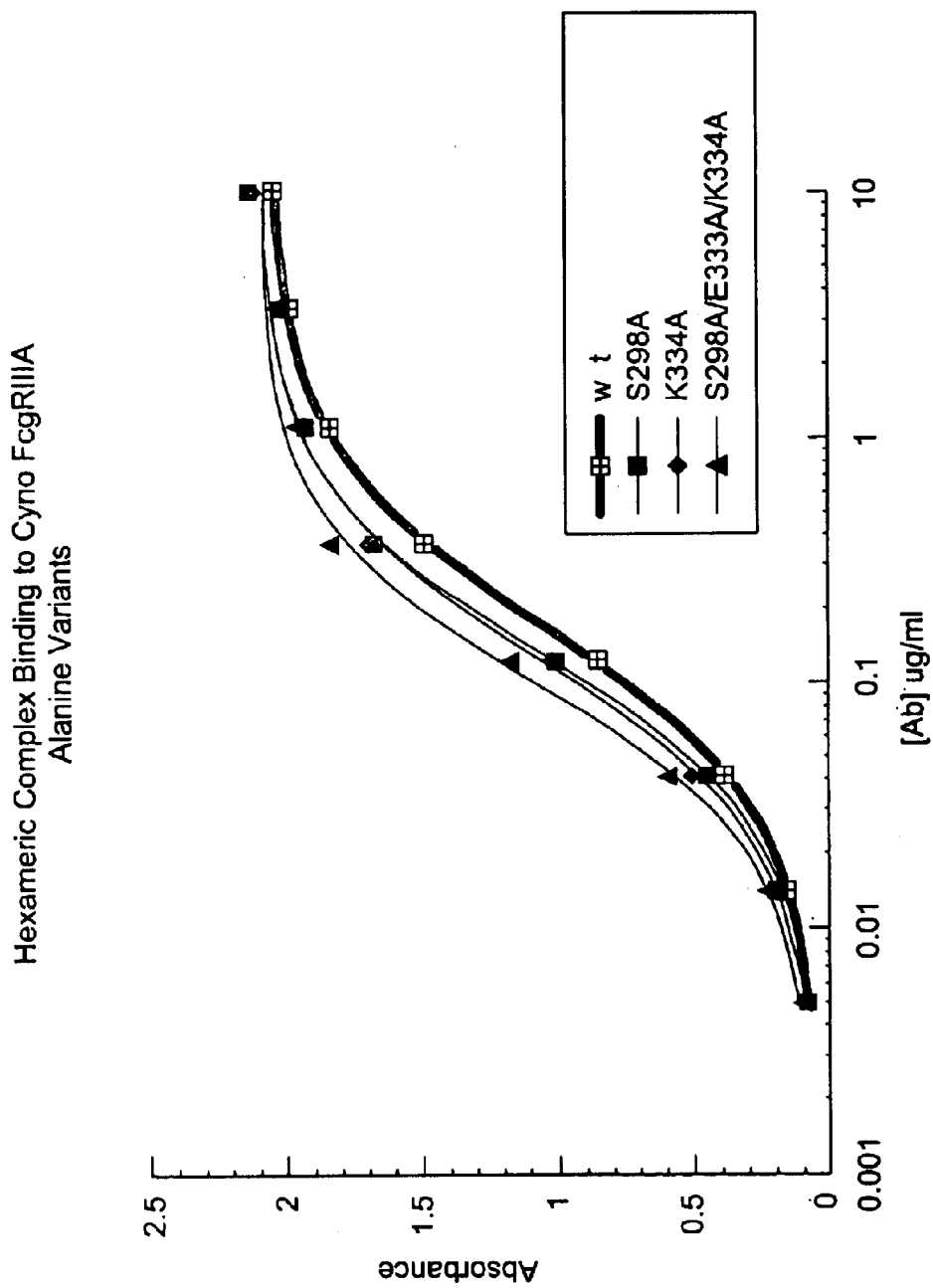

As illustrated by Table 19 and FIGS. 5–7, the binding pattern of all IgG variants to cynomolgus FcγRI was similar to that for human FcγRI. With regard to IgG variant binding to cynomolgus FcγRIIA, the pattern generally followed the same pattern for human polymorph FcγRIIA(H131). (FIG. 5). As above, this likely reflects the fact that the cynomolgus FcγRIIA has a histidine as residue 131. Note, however, that there were two notable exceptions, variant S298A and variant S298A/E333A/K334A had improved binding to the cynomolgus FcγRIIA as compared to native human IgG1, and these same variants bound poorly to human FcγRIIA.

Referring to Table 19 and FIG. 6, the pattern of variant IgG binding to cynomolgus FcγRIIB exhibited several differences from the binding pattern for human FcγRIIB. In particular, variants R255A, E255A, E258A, S37A, D280A, and R301A bound the cynomolgus FcγRIIB equivalently as they had native human IgG, whereas these same variants all exhibited improved binding to the human FcγRIIB when compared to native human IgG.

Referring to Table 19 and FIG. 7, the binding pattern of the variant IgG to cynomolgus FcγRIIIA followed the binding pattern established for human polymorph FcγRIIIA-V158, as compared to the binding pattern for human polymorph FcγRIIIA-F158. This likely reflects the fact that the cynomolgus FcγRIIIA has a similar amino acid residue, isoleucine, at position 158 as does human FcγRIIIA-V158 (compared to the phenylalanine located in FcγRIIIA-F 158).

Blocking the inhibitory signals (e.g., ITIM-containing FcγRIIB) mediated by Fc receptors, which counterbalance the activating signals (e.g., ITAM-containing FcγRI, FcγRIIA, and FcγRIIIA) mediated by Fc receptors, may provide for improved therapeutic efficacy of antibodies. An unexpected result shown in Table 19 is that variants having S298A showed improved binding to cynomolgus FcγRIIA, maintained native-like binding to cynomolgus FcγRI and FcγRIIIA, and showed significantly decreased binding to cynomolgus FcγRIIB. Two variants in particular, S298A and S298A/E333A/K334A may be used to selectively engage the activating ITAM-containing Fc receptors, while simultaneously not engaging the inhibitory ITIM-containing FcγRIIB.

TABLE 19

Binding of Human E27IgG1 Variants to Human and Cynomolgus FcγR

| Variant | FcγRI | FcγRIIA | FcγRIIB | FcγRIIIA |
|---|---|---|---|---|
| S239A | | | | |
| Human | 0.81 ± 0.09 | 0.73 ± 0.25 | 0.76 ± 0.36 | 0.26 ± 0.08 |
| Cynomolgus | N/A | 0.68 ± 0.04 | N/A | N/A |
| R255A | | | | |
| Human | 0.99 ± 0.12 | 1.30 ± 0.20 | 1.59 ± 0.42 | 0.98 ± 0.18 |
| Cynomolgus | 0.85 ± 0.15 | 1.09 ± 0.07 | 0.80 ± 0.06 | 0.91 ± 0.08 |
| E258A | | | | |
| Human | 1.18 ± 0.13 | 1.33 ± 0.22 | 1.65 ± 0.38 | 1.12 ± 0.12 |
| Cynomolgus | 0.91 ± 0.08 | 0.88 ± 0.05 | 0.99 ± 0.07 | 0.93 ± 0.11 |

TABLE 19-continued

Binding of Human E27IgG1 Variants to Human and Cynomolgus FcγR

| Variant | FcγRI | FcγRIIA | FcγRIIB | FcγRIIIA |
|---|---|---|---|---|
| D265A | | | | |
| Human | 0.16 ± 0.05 | 0.07 ± 0.01 | 0.13 ± 0.05 | 0.09 ± 0.06 |
| Cynomolgus | N/A | 0.05 ± 0.02 | 0.05 | 0.04 ± 0.01 |
| S37A | | | | |
| Human | 1.09 ± 0.08 | 1.52 ± .22(R) 1.10 ± .12(H) | 1.84 ± 0.43 | 1.05 ± 0.24 |
| Cynomolgus | 1.02 ± 0.09 | 1.23 ± 0.34 | 1.04 ± 0.30 | 0.88 ± 0.11 |
| H268A | | | | |
| Human | 1.10 ± 0.11 | 1.21 ± .14(R) 0.97 ± .15(H) | 1.44 ± 0.22 | 0.54 ± 0.12 |
| Cynomolgus | 1.02 ± 0.09 | 0.99 ± 0.07 | 1.20 | 0.86 ± 0.07 |
| D280A | | | | |
| Human | 1.04 ± 0.08 | 1.34 ± 0.14 | 1.60 ± 0.31 | 1.09 ± 0.20 |
| Cynomolgus | 0.97 ± 0.08 | 1.45 ± 0.18 | 1.20 ± 0.11 | 0.99 ± 0.04 |
| R292A | | | | |
| Human | 0.95 ± 0.05 | 0.27 ± 0.13 | 0.17 ± 0.07 | 0.89 ± 0.17 |
| Cynomolgus | 0.87 ± 0.08 | 0.80 ± 0.23 | 0.63 ± 0.06 | 0.90 ± 0.09 |
| E293A | | | | |
| Human | 1.11 ± 0.07 | 1.08 ± 0.19 | 1.07 ± 0.20 | 0.31 ± 0.13 |
| Cynomolgus | N/A | 0.92 ± 0.07 | N/A | N/A |
| S298A | | | | |
| Human | 1.11 ± 0.03 | 0.40 ± .15(R) 0.24 ± .08(H) | 0.23 ± 0.13 | 1.34 ± 0.20(F) 1.07 ± .07(V) |
| Cynomolgus | 1.06 ± 0.09 | 2.07 ± 0.30 | 0.20 ± 0.09 | 0.98 ± 0.13 |
| R301M | | | | |
| Human | 1.06 ± 0.12 | 1.29 ± 0.17 | 1.56 ± 0.12 | 0.48 ± 0.21 |
| Cynomolgus | 1.00 ± 0.09 | 1.62 ± 0.30 | 1.27 ± 0.20 | 0.85 ± 0.08 |
| P329A | | | | |
| Human | 0.48 ± 0.10 | 0.08 ± 0.02 | 0.12 ± 0.08 | 0.21 ± 0.03 |
| Cynomolgus | N/A | 0.21 ± 0.06 | N/A | N/A |
| E333A | | | | |
| Human | 0.98 ± 0.15 | 0.92 ± 0.12 | 0.76 ± 0.11 | 1.27 ± 0.17 |
| Cynomolgus | N/A | 0.67 ± 0.09 | N/A | N/A |
| K334A | | | | |
| Human | 1.06 ± 0.07 | 1.01 ± 0.15 | 0.90 ± 0.12 | 1.39 ± 0.19(F) 1.10 ± .07(V) |

TABLE 19-continued

Binding of Human E27IgG1 Variants to Human and Cynomolgus FcγR

| Variant | FcγRI | FcγRIIA | FcγRIIB | FcγRIIIA |
|---|---|---|---|---|
| Cynomolgus A339T | 1.08 ± 0.09 | 0.92 ± 0.15 | 0.66 ± 0.14 | 1.00 ± 0.15 |
| Human | 1.06 ± 0.04 | 1.09 ± 0.03 | 1.20 ± 0.03 | 1.34 ± 0.09 |
| Cynomolgus S298A/E333A/K334A | N/A | 1.05 ± 0.02 | N/A | N/A |
| Human | N/A | 0.35 ± 0.13 | 0.18 ± 0.08 | 1.51 ± 0.31(F) 1.11 ± .08(V) |
| Cynomolgus | 1.19 ± 0.08 | 1.99 ± 0.24 | 0.12 ± 0.04 | 1.08 ± 0.15 |

Example 8

Cynomolgus FcRn and Human FcRn Bind Human IgG Subclasses Equivalently

Materials and Methods

Human IgG2, IgG3, and IgG4 isotypes of E27 (IgG1) were constructed by subcloning the appropriate heavy chain Fc cDNA from a human spleen cDNA library into a pRK vector containing the E27 variable heavy domain. All IgG subclasses and variants were expressed using the same E27 κ light chain.

Following cotransfection of heavy and light chain plasmids into 293 cells, IgG1, IgG2, IgG4 and variants were purified by protein A chromatography. IgG3 was purified using protein G chromatography. All protein preparations were analyzed using a combination of SDS-polyacrylamide gel electrophoresis, ELISA, and spectroscopy.

Herceptin™ IgG1 was essentially constructed as described in Coussens et al., 1985, Science, 230:1132–39. Herceptin™ IgG1 is a recombinant DNA-derived monoclonal antibody having an IgG1 κ chain that contains a consensus amino acid framework with complementary-determining regions of a murine antibody (4D5) that binds HER2.

The cDNA for cynomologus FcRn was isolated by reverse transcriptase-PCR (GeneAmp, PerkinElmer Life Sciences) of oligo(dT)-primed RNA from cynomologus spleen cells using primers that generated a fragment encoding the α-chain extra-cellular domain as described in Example 1. The cDNA was subcloned into previously described pRK mammalian cell expression vectors, as described in Eaton et al., 1986, Biochemistry, 25:8343–8347. Two DNA sequences were identified and confirmed that differed at base 77, one sequence had base G, giving Ser 3 in the mature polypeptide, and the other had base A giving Aspargine 3 in the mature polypeptide. The cDNA for cynomolgus FcRn (S3) and FcRn (N3) were isolated essentially as described in Example 1.

The cynomolgus and human FcRn plasmids were transfected into human embryonic kidney cells by calcium phosphate precipitation (Gorman, C. M., Gies, D. R., and McCray, G, 1990, DNA Prot. Engineer. Tech., 2:3–10). Supernatants were collected 72 hours after conversion to serum-free $PSO_4$ medium supplemented with 10 mg/liter recombinant bovine insulin, 1 mg/liter human transferrin, and trace elements. Proteins were purified using nickel nitrothiacetic acid chromatography (Qiagen, Valencia, Calif.). Purified protein was analyzed through a combination of 4–20% SDS-polyacrylamide gel electrophoresis, ELISA, and amino acid analysis.

Standard enzyme-linked immunoabsorbent assays (ELISA) were performed in order to detect and quantify interactions between cynomolgus FcRn (S3), FcRn (N3) or human FcRn and human IgG1 (including herceptin IgG1), IgG2, IgG3, or IgG4 (table 20). ELISA plates (Nunc) were coated with 2 µg/ml streptavidin (Zymed Laboratories Inc., South San Francisco, Calif.) in 50 mM carbonate buffer, pH 9.6, at 4° C. overnight. Plates were blocked with PBS, 0.5% BSA, 10 ppm Proclin 300 (Supelco, Bellefonte, Pa.), pH 7.2 at 25° C. for 1 h. FcRn-Gly-$His_6$ was biotynylated using a standard protocol with biotin-X-NHS (Research Organics, Cleveland, Ohio) and bound to streptavidin coated plates at 2 µg/ml in PBS, 0.5 BSA, 0.05% polysorbate-20 (sample buffer), pH 7.2 at 25° C. for 1 h. Plates were then rinsed with sample buffer, pH 6.0. Eight serial 2-fold dilutions of E27 standard or variants in sample buffer at pH 6.0 were incubated for 2 h. Plates were rinsed with sample buffer pH 6.0 and bound IgG was detected with peroxidase-conjugated goat F(ab')$_2$ anti-human IgG F(ab')$_2$ (Jackson ImmunoResearch) in pH 6.0 sample buffer using 3,3',5,5'-tetramethlbenzidine (Kirkegaard & Perry Laboratories, Gaithersburg, Md.) as substrate. Absorbance at 450 nm was read on a $V_{max}$ plate reader (Molecular Devices).

The data shown in Table 20 was plotted as saturation binding curves.

Results and Discussion

Figure 8:
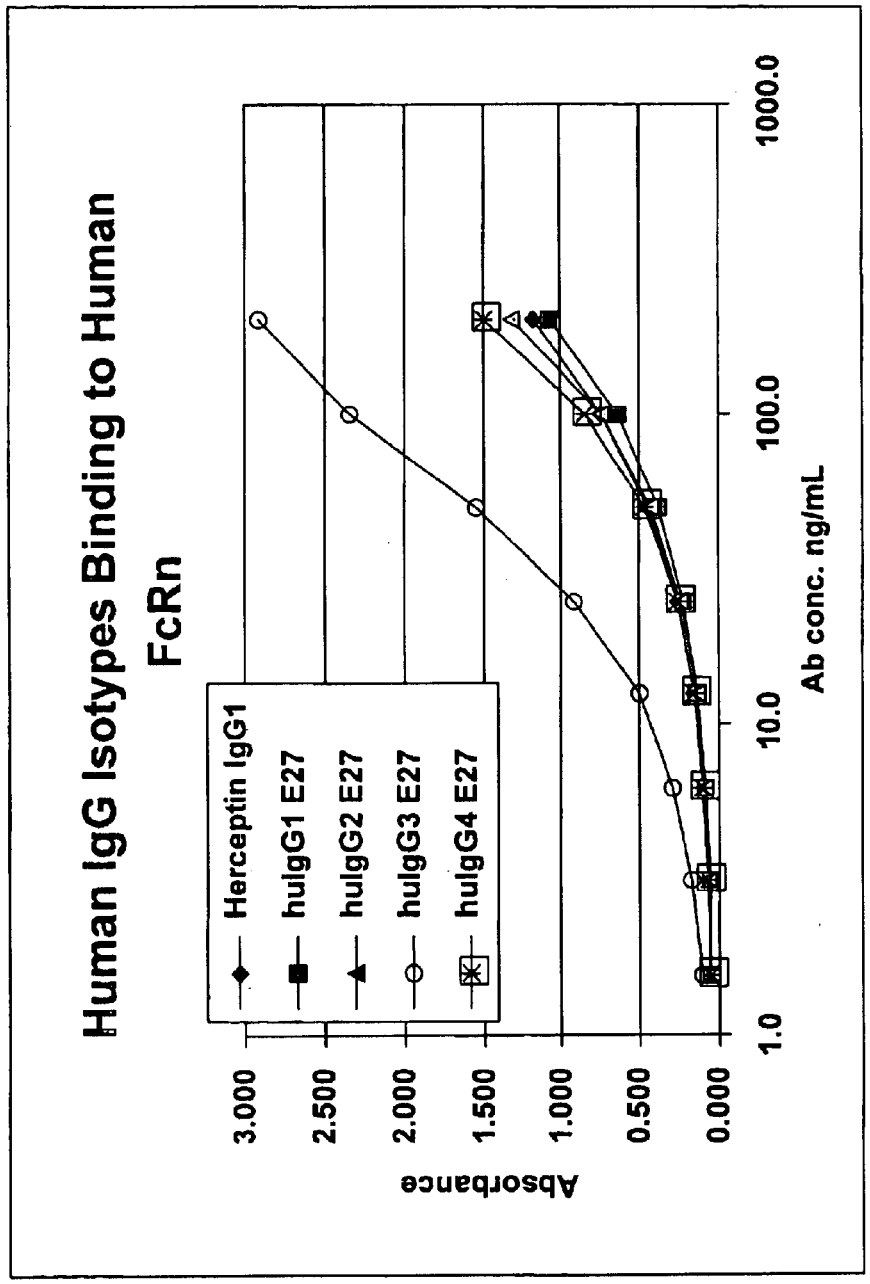
Figure 9:
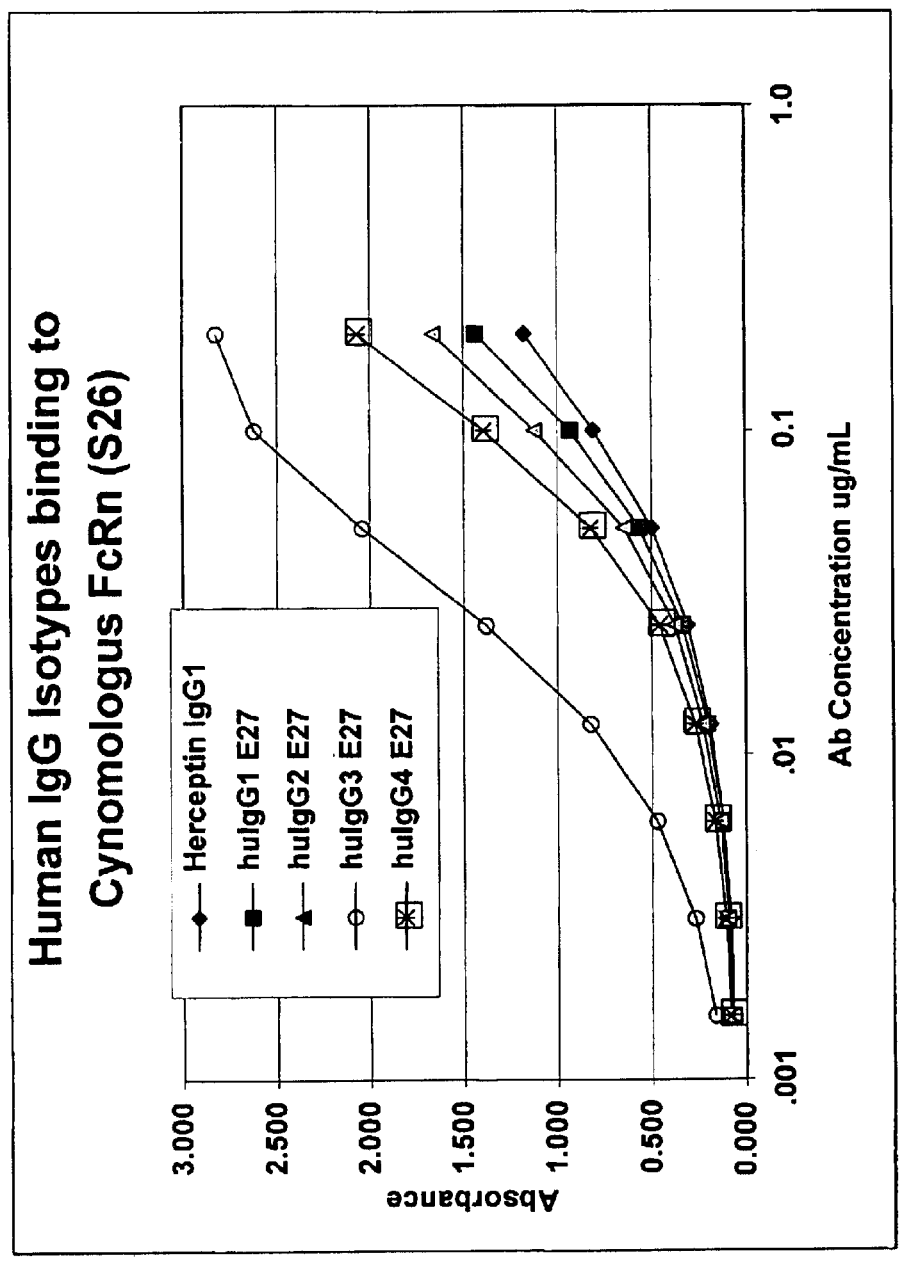
Figure 10:
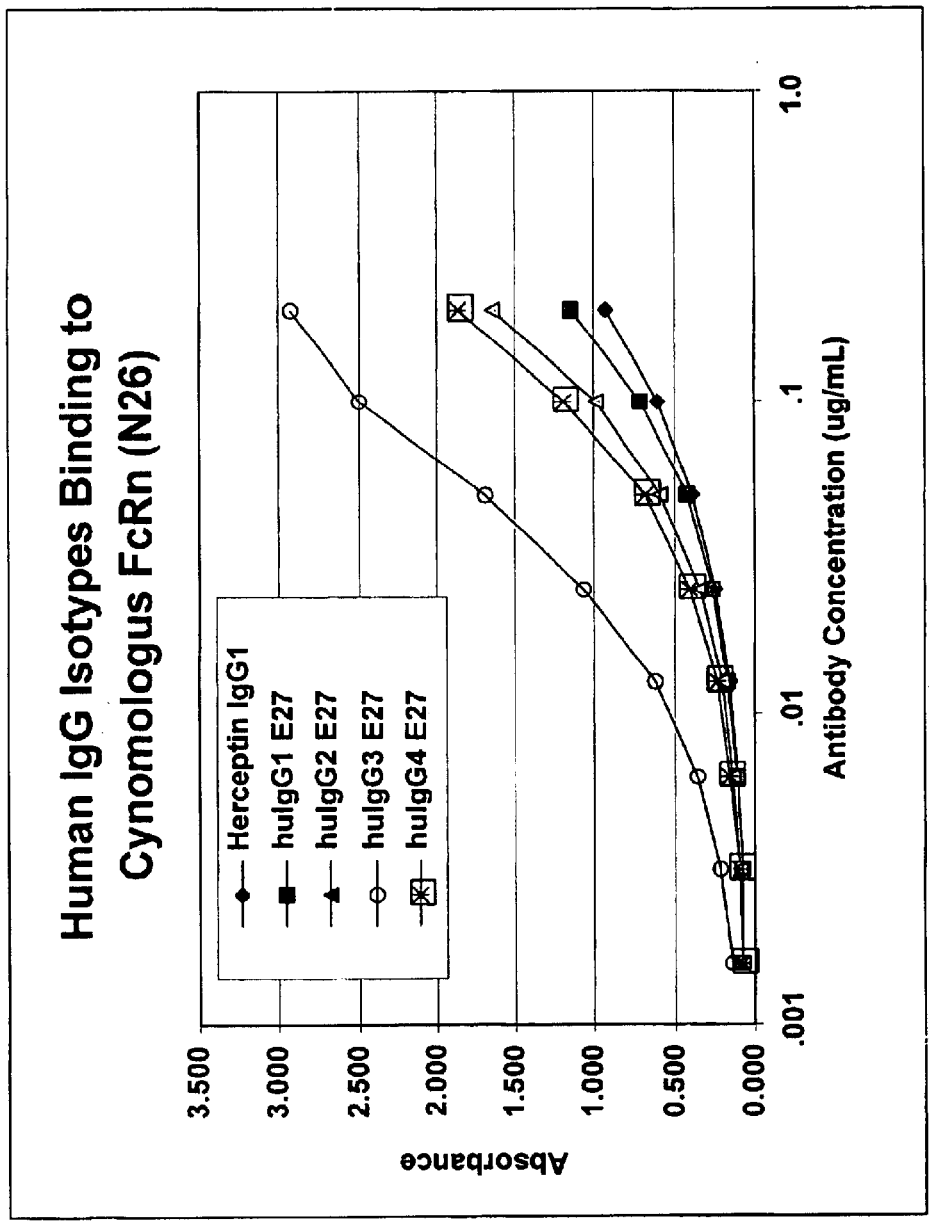

As illustrated in Table 20 and corresponding FIGS. 8-10, the pattern of binding of cynomolgus FcRn (S3), FcRn (N3) and human FcRn to the four human IgG subclasses was similar. In each case, human and cynomolgus FcRns showed the highest level of binding to IgG3 and the lowest level of binding to IgG1. In particular, the pattern for both human and cynomolgus receptor-IgG interaction was IgG3>>IgG4>IgG2>IgG1. Note that the data from the human FcRn-IgG binding interactions corresponds to data previously reported. A P West Jr. and P. J. Bjorkman Biochemistry 39:9698 (2000).

In addition, the data illustrates that the binding affinity of the human and cynomolgus FcRns is similar for IgG1, IgG2, and IgG3, and is slightly stronger for IgG4, as compared to the human FcRn for IgG4. As illustrated graphically in FIGS. 8-10, binding of the human and cynomolgus FcRns to the human IgG subclasses is concentration-dependent and saturable.

TABLE 20

Binding of Human IgG Subclasses to Human FcRn

| Subclass | Cyno S3[a] | Cyno N3[a] | Human[b] | Human[c] |
|---|---|---|---|---|
| E27IgG1 | 1.00, 1.00 | 1.00, 1.00 | 1.00 | 1.00 |
| E27IgG2 | 1.30, 1.15 | 1.49, 1.39 | 1.06 ± 0.10 | 0.93 ± 0.16 |
| E27IgG3 | 3.82, 3.59 | 4.34, 3.97 | 5.60 ± 1.31 | 1.55 ± 0.45 |
| E27IgG4 | 1.52, 1.44 | 1.59, 1.62 | 1.06 ± 0.23 | 0.95 ± 0.14 |

[a]Assay with NeutrAvidin coated on plate followed by FcRn-biotin, then sample and detection with HRP-conjugated goat anti-human F(ab')$_2$. Values are the ratio of $OD_{490\ nm}$ (E27IgG subclass) to $OD_{490\ nm}$ (E27IgG1) at [mAb] = 50 ng/ml for two assays. Cyno S3 and N3 differ only in the amino acid at position 3.

TABLE 20-continued

Binding of Human IgG Subclasses to Human FcRn

| Subclass | Cyno S3[a] | Cyno N3[a] | Human[b] | Human[c] |

[b]Assay with NeutrAvidin coated on plate followed by FcRn-biotin, then sample and detection with HRP-conjugated goat anti-human F(ab')$_2$. Values are the ratio of OD$_{490\ nm}$ (E27IgG subclass) to OD$_{490\ nm}$ (E27IgG1) at [mAb] = 50 ng/ml for five assays. A second, separate lot of E27IgG1 showed a ratio of 0.81 ± 0.03 (mean ± S.D., n = 3) compared to the E27IgG1 used as standard.
[c]Assay with human IgE coated on the plate followed by sample, then FcRn-biotin and detection with HRP-conjugated streptavidin. Values are the ratio of OD$_{490\ nm}$ (E27IgG subclass) to OD$_{490\ nm}$ (E27IgG1) at [mAb] = 50 ng/ml for four assays. A second, separate lot of E27IgG1 showed ratios of 0.92 and 0.88 compared to the E27IgG1 used as standard.

This data illustrates that cynomolgus FcRn can replace human FcRn in the detection of human IgG subclasses as human and cynomolgus FcRn reveal similar binding patterns of interaction with similar affinities for each IgG subclass.

It will be clear that the invention is well adapted to attain the ends and advantages mentioned as well as those inherent therein. While a presently preferred embodiment has been described for purposes of this disclosure, various changes and modifications may be made which are well within the scope of the invention. Numerous other changes may be made which will readily suggest themselves to those skilled in the art and which are encompassed in the spirit of the invention disclosed herein and as defined in the appended claims.

All publications cited herein are hereby incorporated by reference.

What is claimed is:

1. An isolated nucleic acid comprising a polynucleotide sequence that encodes a non-human primate Fc receptor polypeptide with an amino acid sequence of SEQ ID NO: 9 or a fragment corresponding to amino acids 1 to 269 of SEQ ID NO: 65.

2. An isolated nucleic acid of claim 1, wherein the polynucleotide sequence has a sequence of SEQ ID NO: 1.

3. An isolated nucleic acid encoding an Fc receptor polypeptide prepared according to the method comprising:
   a) amplifying a nucleic acid from a nonhuman primate cell with a primer set comprising a forward and a reverse primer, wherein the primer sets are selected from SEQ ID NO:31 and SEQ ID NO:32 or SEQ ID NO:33 and SEQ ID NO:34; and
   b) isolated the amplified nucleic acid.

4. An isolated nucleic acid of claim 1, wherein the polynucleotide encodes an extracellular fragment of the Fc receptor polypeptide with an amino acid sequence corresponding to amino acids 1 to 269 of SEQ ID NO:65.

5. A vector comprising a nucleic acid of claim 1.

6. A host cell comprising a vector of claim 5.

7. A host according to claim 6, wherein the cell is a mammalian cell.

8. A nucleic acid of claim 1, further comprising a polypeptide nucleotide sequence encoding a heterologous polypeptide operably linked to the nucleotide sequence encoding a Fc receptor polypeptide, wherein the heterologous polypeptide is selected from the group consisting of Gly/His$_6$ fused to glutathione S-transferase, 6-His tag, thioredoxin tag, hemaglutinin tag, Glylh156 tag, and OmpA signal sequence tag.

9. An isolated nucleic acid comprising a polynucleotide sequence that encodes a non-human primate Fc receptor polypeptide with an amino acid sequence of SEQ ID NO: 65 or a fragment corresponding t6o amino acids 1 to 269 of SEQ ID NO: 65.

10. An isolated nucleic acid of claim 9, wherein the polynucleotide sequence has a sequence of SEQ ID NO: 1.

11. A vector comprising a nucleic acid of claim 9.

12. A host cell comprising a vector of claim 11.

13. A host according to claim 12, wherein the cell is a mammalian cell.

14. A nucleic acid of claim 9, further comprising a polypeptide nucleotide sequence encoding a heterologous polypeptide operably linked to the nucleotide sequence encoding a Fc receptor polypeptide, wherein the heterologous polypeptide is selected from the group consisting of Gly/His$_6$ fused to glutathione S-transferase, 6-His tag, thioredoxin tag, hemaglutinin tag, Glyh156 tag, and OmpA signal sequence tag.

* * * * *

UNITED STATES PATENT AND TRADEMARK OFFICE
CERTIFICATE OF CORRECTION

PATENT NO. : 6,911,321 B2  
APPLICATION NO. : 10/027736  
DATED : June 28, 2005  
INVENTOR(S) : Presta et al.

It is certified that error appears in the above-identified patent and that said Letters Patent is hereby corrected as shown below:

Title page,
Item [56], References Cited, OTHER PUBLICATIONS,
"Kurucz, I. et al." reference, "functionally actie after" should read -- functionally active after --.
"Luckow, V. et al." reference, "1998)." should read -- 1988). --.
"Shields, R. et al." reference, "for FcγRI, FcγII, FcγRIII," should read -- for FcγRI, FcγRII, FcγRIII, --.

Column 2,
Line 18, "The γ-chain" should read -- The δ-chain --.

Column 3,
Line 60, "nucfeotides of the" should read -- nucletides of the --.

Column 142,
Line 53, "A host cell" should read -- An isolated host cell --.
Lines 56-57, "comprising a polypeptide nucletide sequence" should read -- comprising a nucleotide sequence --.
Line 66, "corresponding t6o amino" should read -- corresponding to amino --.

Column 143,
Line 3, "comprising a nucleic" should read -- comprising the nucleic --.
Line 4, "A host cell" should read -- An isolated host cell --.
Line 8, "polypeptide nucleotide sequence" should read -- nucleotide sequence --.

Signed and Sealed this

Twenty-seventh Day of June, 2006

JON W. DUDAS  
*Director of the United States Patent and Trademark Office*

SEQUENCE LISTING

<160> NUMBER OF SEQ ID NOS: 72

<210> SEQ ID NO 1
<211> LENGTH: 1074
<212> TYPE: DNA
<213> ORGANISM: Cynomolgus
<220> FEATURE:
<221> NAME/KEY: misc_feature
<222> LOCATION: (1)..(1074)
<223> OTHER INFORMATION: FcgammaRI alpha-chain

<400> SEQUENCE: 1

```
atgtggttct tgacagctct gctcctttgg gttccagttg atgggcaagt ggataccaca      60
aaggcagtga tcactttgca gcctccatgg gtcagcgtgt ccaagagga aactgtaacc      120 ttacagtgtg aggtgccccg tctgcctggg agcagctcca cacagtggtt tctcaatggc      180
acagccactc agacctcgac tcccagctac agaatcacct ctgccagtgt caaggacagt      240
ggtgaataca ggtgccagag aggtccctca gggcgaagtg accccataca gctggaaatc      300
cacagagact ggctactact gcaggtatcc agcagagtct tcacagaagg agaacctctg      360
gccttgaggt gtcatgcatg gaaggataag ctggtgtaca atgtgcttta ctatcaaaat      420
ggcaaagcct ttaagttttt ctaccggaat tctcaactca ccattctgaa aaccaacata      480
agtcacaacg gcgcctacca ctgctcaggc atgggaaagc atcgctacac atcagcagga      540
gtatctgtca ctgtgaaaga gctatttcca gctccagtgc tgaatgcatc cgtgacatcc      600
ccgctcctgg aggggaatct ggtcaccctg agctgtgaaa caaagttgct tctgcagagg      660
cctggtttgc agctttactt ctccttctac atgggcagca agaccctgcg aggcaggaac      720
acgtcctctg aataccaaat actaactgct agaagagaag actctgggtt ttactggtgc      780
gaggccacca cagaagacgg aaatgtcctt aagcgcagcc ctgagttgga gcttcaagtg      840
cttggcctcc agttaccaac tcctgtctgg cttcatgtcc ttttctatct ggtagtggga      900
ataatgtttt tagtgaacac tgttctctgg gtgacaatac gtaaagaact gaaaagaaag      960
aaaaagtgga atttagaaat atctttggat tctgctcatg agaagaaggt aacttccagc     1020
cttcaagaag acagacattt agaagaagag ctgaagagtc aggaacaaga ataa           1074
```

<210> SEQ ID NO 2
<211> LENGTH: 1128

```
<212> TYPE: DNA
<213> ORGANISM: Homo sapiens
<220> FEATURE:
<221> NAME/KEY: misc_feature
<222> LOCATION: (1)..(1128)
<223> OTHER INFORMATION: FcgammaRI alpha-chain

<400> SEQUENCE: 2
atgtggttct tgacaactct gctcctttgg gttccagttg atgggcaagt ggacaccaca      60
aaggcagtga tcactttgca gcctccatgg gtcagcgtgt tccaagagga aaccgtaacc     120
ttgcactgtg aggtgctcca tctgcctggg agcagctcta cacagtggtt tctcaatggc     180
acagccactc agacctcgac ccccagctac agaatcacct ctgccagtgt caatgacagt     240
ggtgaataca ggtgccagag aggtctctca gggcgaagtg acccataca gctgaaaatc      300
cacagaggct ggctactact gcaggtctcc agcagagtct tcacggaagg agaacctctg     360
gccttgaggt gtcatgcgtg gaaggataag ctggtgtaca atgtgcttta ctatcgaaat     420
ggcaaagcct ttaagttttt ccactggaat tctaacctca ccattctgaa aaccaacata     480
agtcacaatg gcacctacca ttgctcaggc atgggaaagc atcgctacac atcagcagga     540
atatctgtca ctgtgaaaga gctatttcca gctccagtgc tgaatgcatc tgtgacatcc     600
ccactcctgg aggggaatct ggtcacccta gctgtgaaa caaagttgct cttgcagagg      660
cctggtttgc agctttactt ctccttctac atgggcagca gaccctgcg aggcaggaac      720
acatcctctg aataccaaat actaactgct agaagagaag actctgggtt atactggtgc     780
gaggctgcca cagaggatgg aaatgtcctt aagcgcagcc ctgagttgga gcttcaagtg     840
cttggcctcc agttaccaac tcctgtctgg tttcatgtcc ttttctatct ggcagtggga     900
ataatgtttt tagtgaacac tgttctctgg gtgacaatac gtaaagaact gaaaagaaag     960
aaaaagtggg atttagaaat ctctttggat tctggtcatg agaagaaggt aatttccagc    1020
cttcaagaag acagacattt agaagaagag ctgaaatgtc aggaacaaaa agaagaacag    1080
ctgcaggaag gggtgcaccg gaaggagccc caggggccac gtagcag                  1128

<210> SEQ ID NO 3
<211> LENGTH: 933
<212> TYPE: DNA
<213> ORGANISM: Cynomolgus
<220> FEATURE:
<221> NAME/KEY: misc_feature
<222> LOCATION: (1)..(933)
<223> OTHER INFORMATION: FcgammaRIIA

<400> SEQUENCE: 3
atgtctcaga atgtatgtcc cggcaacctg tggctgcttc aaccattgac agttttgctg      60
ctgctggctt ctgcagacag tcaaactgct cccccgaagg ctgtgctgaa actcgagccc     120
ccgtggatca acgtgctccg ggaggactct gtgactctga cgtgcggggg cgctcacagc     180
cctgacagcg actccactca gtggttccac aatgggaatc gcatccccac ccacacacag     240
cccagctaca ggttcaaggc caacaacaat gatagcgggg agtacaggtg ccagactggc     300
cggaccagcc tcagcgaccc tgttcatctg actgtgcttt ctgagtggct ggcgcttcag     360
accccctcacc tggagttccg ggaggggaaa accatcatgc tgaggtgcca cagctggaag     420
gacaagcctc tgatcaaggt cacattcttc cagaatggaa tagccaagaa attttcccat     480
atggatccca atttctccat cccacaagca aaccacagtc acagtggtga ttaccactgc     540
acaggaaaca taggctacac accatactca tccaaacctg tgaccatcac tgtccaagtg     600
```

```
cccagcgtgg gcagctcttc accgatgggg atcattgtgg ctgtggtcac tgggattgct    660
gtagcggcca ttgttgctgc tgtagtggcc ttgatctact gcaggaaaaa gcggatttca    720
gccaattcca ctgatcctgt gaaggctgcc cgatttgagc cacttggacg tcaaacgatt    780
gccctcagaa agagacaact tgaagaaacc aacaatgact atgaaacagc cgacggcggc    840
tacatgactc tgaaccccag ggcacctact gatgatgata gaaacatcta cctgactctt    900
tctcccaacg actatgacaa cagtaataac taa                                 933
```

<210> SEQ ID NO 4
<211> LENGTH: 936
<212> TYPE: DNA
<213> ORGANISM: Homo sapiens
<220> FEATURE:
<221> NAME/KEY: misc_feature
<222> LOCATION: (1)..(936)
<223> OTHER INFORMATION: FcgammaRIIA

<400> SEQUENCE: 4

```
atgtctcaga atgtatgtcc cagaaacctg tggctgcttc aaccattgac agttttgctg    60
ctgctggctt ctgcagacag tcaagctgca gctcccccaa aggctgtgct gaaacttgag    120
cccccgtgga tcaacgtgct ccaggaggac tctgtgactc tgacatgcca ggggctcgc    180 agccctgaga gcgactccat tcagtggttc cacaatggga atctcattcc cacccacacg    240
cagcccagct acaggttcaa ggccaacaac aatgacagcg gggagtacac gtgccagact    300
ggccagacca gcctcagcga ccctgtgcat ctgactgtgc tttccgaatg ctggtgctc    360 cagaccctc acctggagtt ccaggaggga gaaaccatca tgctgaggtg ccacagctgg    420
aaggacaagc tctggtcaa ggtcacattc ttccagaatg aaaatcccc gaaattctcc    480 cgtttggatc ccaccttctc catcccacaa gcaaaccaca gtcacagtgg tgattaccac    540
tgcacaggaa acataggcta cacgctgttc tcatccaagc ctgtgaccat cactgtccaa    600
gtgcccagca tgggcagctc ttcaccaatg gggatcattg tggctgtggt cattgcgact    660
gctgtagcag ccattgttgc tgctgtagtg gccttgatct actgcaggaa aaagcggatt    720
tcagccaatt ccactgatcc tgtgaaggct gcccaatttg agccacctgg acgtcaaatg    780
attgccatca gaaagagaca acttgaagaa accaacaatg actatgaaac agctgacggc    840
ggctacatga ctctgaaccc caggcacct actgacgatg ataaaaacat ctacctgact    900
cttcctccca cgaccatgt caacagtaat aactaa                             936
```

<210> SEQ ID NO 5
<211> LENGTH: 885
<212> TYPE: DNA
<213> ORGANISM: Cynomolgus
<220> FEATURE:
<221> NAME/KEY: misc_feature
<222> LOCATION: (1)..(885)
<223> OTHER INFORMATION: FcgammaRIIB
<220> FEATURE:
<221> NAME/KEY: misc_feature
<222> LOCATION: (879)..(879)
<223> OTHER INFORMATION: n = a or g or c or t/u unknown or other

<400> SEQUENCE: 5

```
atgggaatcc tgtcattctt acctgtcctt gctactgaga gtgactgggc tgactgcaag    60
tcctcccagc cttggggcca catgcttctg tggacagctg tgctattcct ggctcctgtt    120
gctgggacac ctgcagctcc cccgaaggct gtgctgaaac tcgagccccc gtggatcaac    180
gtgctccggg aggactctgt gactctgacg tgcggggggcg ctcacagccc tgacagcgac    240
```

```
tccactcagt ggttccacaa tgggaatctc atccccaccc acacgcagcc cagctacagg      300
ttcaaggcca acaacaatga tagcggggag tacaggtgcc agactggccg gaccagcctc      360
agcgaccctt tcatctgac tgtgctttct gagtggctgg cgctccagac ccctcacctg       420
gagttccggg agggagaaac catcttgctg aggtgccaca gctggaagga caagcctctg      480
atcaaggtca cattcttcca gaatggaata tccaagaaat ttcccatat gaatcccaac       540 ttctccatcc cacaagcaaa ccacagtcac agtggtgatt accactgcac aggaaacata     600
ggctacacac catactcatc caaacctgtg accatcactg tccaagtgcc cagcatgggc      660
agctcttcac cgatagggat cattgtggct gtggtcactg ggattgctgt agcggccatt     720
gttgctgctg tagtggcctt gatctactgc aggaaaaagc ggatttcagc caatcccact     780
aatcctgacg aggctgacaa agttggggct gagaacacaa tcacctattc acttctcatg    840
catccggacg ctctggaaga gcctgatgac caaaaccgng tttag                     885
```

<210> SEQ ID NO 6
<211> LENGTH: 876
<212> TYPE: DNA
<213> ORGANISM: Homo sapiens
<220> FEATURE:
<221> NAME/KEY: misc_feature
<222> LOCATION: (1)..(876)
<223> OTHER INFORMATION: FcgammaRIIB

<400> SEQUENCE: 6

```
atgggaatcc tgtcattctt acctgtcctt gccactgaga gtgactgggc tgactgcaag       60 tcccccagc cttggggtca tatgcttctg tggacagctg tgctattcct ggctcctgtt       120
gctgggacac ctgcagctcc cccaaaggct gtgctgaaac tcgagcccca gtggatcaac     180
gtgctccagg aggactctgt gactctgaca tgccggggga ctcacagccc tgagagcgac     240
tccattcagt ggttccacaa tgggaatctc attcccaccc acacgcagcc cagctacagg     300
ttcaaggcca acaacaatga cagcggggag tacacgtgcc agactggcca gaccagcctc     360
agcgaccctt gcatctgac tgtgctttct gagtggctgg tgctccagac ccctcacctg     420
gagttccagg agggagaaac catcgtgctg aggtgccaca gctggaagga caagcctctg     480
gtcaaggtca cattcttcca gaatggaaaa tccaagaaat ttccccgttc ggatcccaac     540
ttctccatcc cacaagcaaa ccacagtcac agtggtgatt accactgcac aggaaacata     600
ggctacacgc tgtactcatc aagcctgtg accatcactg tccaagctcc agctcttca     660 ccgatgggga tcattgtggc tgtggtcact gggattgctg tagcggccat tgttgctgct    720
gtagtggcct tgatctactg caggaaaaag cggatttcag ccaatcccac taatcctgat     780
gaggctgaca agttggggc tgagaacaca atcacctatt cacttctcat gcacccggat    840
gctctggaag agcctgatga ccagaaccgt atttag                               876
```

<210> SEQ ID NO 7
<211> LENGTH: 765
<212> TYPE: DNA
<213> ORGANISM: Cynomolgus
<220> FEATURE:
<221> NAME/KEY: misc_feature
<222> LOCATION: (1)..(765)
<223> OTHER INFORMATION: FcgammaRIIIA alpha-chain

<400> SEQUENCE: 7

```
atgtggcagc tgctcctccc aactgctctg ctacttctag tttcagctgg catgcgggct       60
```

```
gaagatctcc caaaggctgt ggtgttcctg gagcctcaat ggtacagggt gctcgagaag      120
gaccgtgtga ctctgaagtg ccagggagcc tactcccctg aggacaattc cacacggtgg      180
tttcacaatg agagcctcat ctcaagccag acctcgagct acttcattgc tgctgccaga      240
gtcaacaaca gtggagagta caggtgccag acaagcctct ccacactcag tgacccggtg      300
cagctggaag tccatatcgg ctggctattg ctccaggccc ctcggtgggt gttcaaggag      360
gaagaatcta ttcacctgag gtgtcacagc tggaagaaca ctcttctgca taaggtcacg      420
tatttacaga atggcaaagg caggaagtat tttcatcaga attctgactt ctacattcca      480
aaagccacac tcaaagacag cggctcctac ttctgcaggg gacttattgg gagtaaaaat      540
gtatcttcag agactgtgaa catcaccatc actcaagatt ggcagtgtc atccatctca      600 tcattctttc cacctgggta ccaagtctct ttctgcctgg tgatggtact cctttttgca      660
gtggacacag gactatattt ctctatgaag aaaagcattc aagctcaac aagggactgg      720 gaggaccata aatttaaatg gagcaaggac cctcaagaca atga                       765

<210> SEQ ID NO 8
<211> LENGTH: 765
<212> TYPE: DNA
<213> ORGANISM: Homo sapiens
<220> FEATURE:
<221> NAME/KEY: misc_feature
<222> LOCATION: (1)..(765)
<223> OTHER INFORMATION: FcgammaRIIIA alpha-chain

<400> SEQUENCE: 8
atgtggcagc tgctcctccc aactgctctg ctacttctag tttcagctgg catgcggact       60
gaagatctcc caaaggctgt ggtgttcctg gagcctcaat ggtacagggt gctcgagaag      120
gacagtgtga ctctgaagtg ccagggagcc tactcccctg aggacaattc cacacagtgg      180
tttcacaatg agagcctcat ctcaagccag gcctcgagct acttcattga cgctgccaca      240
gtcgacgaca gtggagagta caggtgccag acaaacctct ccaccctcag tgacccggtg      300
cagctagaag tccatatcgg ctggctgttg ctccaggccc ctcggtgggt gttcaaggag      360
gaagacccta ttcacctgag gtgtcacagc tggaagaaca ctgctctgca taaggtcaca      420
tatttacaga atggcaaagg caggaagtat tttcatcata attctgactt ctacattcca      480
aaagccacac tcaaagacag cggctcctac ttctgcaggg ggcttttgg gagtaaaaat      540 gtgtcttcag agactgtgaa catcaccatc actcaaggtt tggcagtgtc aaccatctca      600
tcattctttc cacctgggta ccaagtctct ttctgcttgg tgatggtact cctttttgca      660
gtggacacag gactatattt ctctgtgaag acaaacattc gaagctcaac aagagactgg      720
aaggaccata aatttaaatg gagaaaggac cctcaagaca atga                       765

<210> SEQ ID NO 9
<211> LENGTH: 357
<212> TYPE: PRT
<213> ORGANISM: Cynomolgus
<220> FEATURE:
<221> NAME/KEY: MISC_FEATURE
<222> LOCATION: (1)..(357)
<223> OTHER INFORMATION: FcgammaRI <chain

<400> SEQUENCE: 9

Met Trp Phe Leu Thr Ala Leu Leu Leu Trp Val Pro Val Asp Gly Gln
1               5                  10                  15

Val Asp Thr Thr Lys Ala Val Ile Thr Leu Gln Pro Pro Trp Val Ser
            20                  25                  30
```

```
Val Phe Gln Glu Glu Thr Val Thr Leu Gln Cys Glu Val Pro Arg Leu
            35                  40                  45

Pro Gly Ser Ser Ser Thr Gln Trp Phe Leu Asn Gly Thr Ala Thr Gln
        50                  55                  60

Thr Ser Thr Pro Ser Tyr Arg Ile Thr Ser Ala Ser Val Lys Asp Ser
65                  70                  75                  80

Gly Glu Tyr Arg Cys Gln Arg Gly Pro Ser Gly Arg Ser Asp Pro Ile
                85                  90                  95

Gln Leu Glu Ile His Arg Asp Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Gln Asn Gly Lys Ala Phe
    130                 135                 140

Lys Phe Phe Tyr Arg Asn Ser Gln Leu Thr Ile Leu Lys Thr Asn Ile
145                 150                 155                 160

Ser His Asn Gly Ala Tyr His Cys Ser Gly Met Gly Lys His Arg Tyr
                165                 170                 175

Thr Ser Ala Gly Val Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Phe Tyr Trp Cys Glu Ala Thr Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Leu His Val Leu Phe Tyr Leu Val Val Gly Ile Met Phe Leu
    290                 295                 300

Val Asn Thr Val Leu Trp Val Thr Ile Arg Lys Glu Leu Lys Arg Lys
305                 310                 315                 320

Lys Lys Trp Asn Leu Glu Ile Ser Leu Asp Ser Ala His Glu Lys Lys
                325                 330                 335

Val Thr Ser Ser Leu Gln Glu Asp Arg His Leu Glu Glu Glu Leu Lys
            340                 345                 350

Ser Gln Glu Gln Glu
        355

<210> SEQ ID NO 10
<211> LENGTH: 374
<212> TYPE: PRT
<213> ORGANISM: Homo sapiens
<220> FEATURE:
<221> NAME/KEY: MISC_FEATURE
<222> LOCATION: (1)..(374)
<223> OTHER INFORMATION: FcgammaRI alpha-chain

<400> SEQUENCE: 10

Met Trp Phe Leu Thr Thr Leu Leu Leu Trp Val Pro Val Asp Gly Gln
1               5                   10                  15
```

```
Val Asp Thr Thr Lys Ala Val Ile Ser Leu Gln Pro Pro Trp Val Ser
         20                  25                  30

Val Phe Gln Glu Glu Thr Val Thr Leu His Cys Glu Val Leu His Leu
             35                  40                  45

Pro Gly Ser Ser Ser Thr Gln Trp Phe Leu Asn Gly Thr Ala Thr Gln
     50                  55                  60

Thr Ser Thr Pro Ser Tyr Arg Ile Thr Ser Ala Ser Val Asn Asp Ser
 65                  70                  75                  80

Gly Glu Tyr Arg Cys Gln Arg Gly Leu Ser Gly Arg Ser Asp Pro Ile
                 85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
            115                 120                 125

Asp Lys Leu Val Tyr Asn Val Leu Tyr Tyr Arg Asn Gly Lys Ala Phe
130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
            195                 200                 205

Thr Leu Ser Cys Glu Thr Lys Leu Leu Leu Gln Arg Pro Gly Leu Gln
210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
            275                 280                 285

Val Trp Phe His Val Leu Phe Tyr Leu Ala Val Gly Ile Met Phe Leu
            290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Thr Ser Ser Leu Gln Glu Asp Arg His Leu Glu Glu Glu Leu Lys
            340                 345                 350

Cys Gln Glu Gln Lys Glu Glu Gln Leu Gln Glu Gly Val His Arg Lys
            355                 360                 365

Glu Pro Gln Gly Ala Thr
    370

<210> SEQ ID NO 11
<211> LENGTH: 86
<212> TYPE: PRT
<213> ORGANISM: Cynomolgus
<220> FEATURE:
<221> NAME/KEY: MISC_FEATURE
<222> LOCATION: (1)..(86)
<223> OTHER INFORMATION: FcgammaRI/III gamma-chain
```

```
<400> SEQUENCE: 11

Met Ile Pro Ala Val Val Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
            35                  40                  45

Gln Val Arg Lys Ala Ala Ile Ala Ser Tyr Glu Lys Ser Asp Gly Val
        50                  55                  60

Tyr Thr Gly Leu Ser Thr Arg Asn Gln Glu Thr Tyr Glu Thr Leu Lys
65                  70                  75                  80

His Glu Lys Pro Pro Gln
                85

<210> SEQ ID NO 12
<211> LENGTH: 86
<212> TYPE: PRT
<213> ORGANISM: Homo sapiens
<220> FEATURE:
<221> NAME/KEY: MISC_FEATURE
<222> LOCATION: (1)..(86)
<223> OTHER INFORMATION: FcgammaRI/III gamma-chain

<400> SEQUENCE: 12

Met Ile Pro Ala Val Val Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
            35                  40                  45

Gln Val Arg Lys Ala Ala Ile Thr Ser Tyr Glu Lys Ser Asp Gly Val
        50                  55                  60

Tyr Thr Gly Leu Ser Thr Arg Asn Gln Glu Thr Tyr Glu Thr Leu Lys
65                  70                  75                  80

His Glu Lys Pro Pro Gln
                85

<210> SEQ ID NO 13
<211> LENGTH: 261
<212> TYPE: DNA
<213> ORGANISM: Cynomolgus
<220> FEATURE:
<221> NAME/KEY: misc_feature
<222> LOCATION: (1)..(261)
<223> OTHER INFORMATION: gamma chain

<400> SEQUENCE: 13
atgattccag cagtggtctt gctcttactc cttttggttg aacaagcagc ggccctggga      60
gagcctcagc tctgctatat cctggatgcc atcctgtttc tgtatggaat tgtcctcacc     120
ctcctctact gtcgactgaa gatccaagtg cgaaaggcag ctatagccag ctatgagaaa     180
tcagatggtg tttacacggg cctgagcacc aggaaccagg aaacttatga gactctgaag     240
catgagaaac caccacagta g                                               261

<210> SEQ ID NO 14
<211> LENGTH: 261
<212> TYPE: DNA
<213> ORGANISM: Homo sapiens
<220> FEATURE:
<221> NAME/KEY: misc_feature
```

-continued

```
<222> LOCATION: (1)..(261)
<223> OTHER INFORMATION: gamma chain

<400> SEQUENCE: 14
atgattccag cagtggtctt gctcttactc cttttggttg aacaagcagc ggccctggga      60
gagcctcagc tctgctatat cctggatgcc atcctgtttc tgtatggaat tgtcctcacc     120
ctcctctact gtcgactgaa gatccaagtg cgaaaggcag ctataaccag ctatgagaaa     180
tcagatggtg tttacacggg cctgagcacc aggaaccagg agacttacga gactctgaag     240
catgagaaac caccacagta g                                               261

<210> SEQ ID NO 15
<211> LENGTH: 310
<212> TYPE: PRT
<213> ORGANISM: Cynomolgus
<220> FEATURE:
<221> NAME/KEY: MISC_FEATURE
<222> LOCATION: (1)..(310)
<223> OTHER INFORMATION: FcgammaRIIA

<400> SEQUENCE: 15
```

Met Ser Gln Asn Val Cys Pro Gly Asn Leu Trp Leu Leu Gln Pro Leu
1               5                   10                  15

Thr Val Leu Leu Leu Ala Ser Ala Asp Ser Gln Thr Ala Pro Pro
            20                  25                  30

Lys Ala Val Leu Lys Leu Glu Pro Pro Trp Ile Asn Val Leu Arg Glu
        35                  40                  45

Asp Ser Val Thr Leu Thr Cys Gly Gly Ala His Ser Pro Asp Ser Asp
    50                  55                  60

Ser Thr Gln Trp Phe His Asn Gly Asn Arg Ile Pro Thr His Thr Gln
65                  70                  75                  80

Pro Ser Tyr Arg Phe Lys Ala Asn Asn Asn Asp Ser Gly Glu Tyr Arg
                85                  90                  95

Cys Gln Thr Gly Arg Thr Ser Leu Ser Asp Pro Val His Leu Thr Val
            100                 105                 110

Leu Ser Glu Trp Leu Ala Leu Gln Thr Pro His Leu Glu Phe Arg Glu
        115                 120                 125

Gly Glu Thr Ile Met Leu Arg Cys His Ser Trp Lys Asp Lys Pro Leu
    130                 135                 140

Ile Lys Val Thr Phe Phe Gln Asn Gly Ile Ala Lys Lys Phe Ser His
145                 150                 155                 160

Met Asp Pro Asn Phe Ser Ile Pro Gln Ala Asn His Ser His Ser Gly
                165                 170                 175

Asp Tyr His Cys Thr Gly Asn Ile Gly Tyr Thr Pro Tyr Ser Ser Lys
            180                 185                 190

Pro Val Thr Ile Thr Val Gln Val Pro Ser Val Gly Ser Ser Pro
        195                 200                 205

Met Gly Ile Ile Val Ala Val Thr Gly Ile Ala Val Ala Ala Ile
    210                 215                 220

Val Ala Ala Val Val Ala Leu Ile Tyr Cys Arg Lys Lys Arg Ile Ser
225                 230                 235                 240

Ala Asn Ser Thr Asp Pro Val Lys Ala Ala Arg Phe Glu Pro Leu Gly
                245                 250                 255

Arg Gln Thr Ile Ala Leu Arg Lys Arg Gln Leu Glu Glu Thr Asn Asn
            260                 265                 270

Asp Tyr Glu Thr Ala Asp Gly Gly Tyr Met Thr Leu Asn Pro Arg Ala

```
                    275                 280                 285
Pro Thr Asp Asp Arg Asn Ile Tyr Leu Thr Leu Ser Pro Asn Asp
    290                 295                 300

Tyr Asp Asn Ser Asn Asn
305                 310

<210> SEQ ID NO 16
<211> LENGTH: 317
<212> TYPE: PRT
<213> ORGANISM: Homo sapiens
<220> FEATURE:
<221> NAME/KEY: MISC_FEATURE
<222> LOCATION: (1)..(317)
<223> OTHER INFORMATION: FcgammaRIIA

<400> SEQUENCE: 16

Met Ala Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
                20                  25                  30

Ser Gln Ala Ala Ala Pro Pro Lys Ala Val Leu Lys Leu Glu Pro Pro
            35                  40                  45

Trp Ile Asn Val Leu Gln Glu Asp Ser Val Thr Leu Thr Cys Gln Gly
    50                  55                  60

Ala Arg Ser Pro Glu Ser Asp Ser Ile Gln Trp Phe His Asn Gly Asn
65                  70                  75                  80

Leu Ile Pro Thr His Thr Gln Pro Ser Tyr Arg Phe Lys Ala Asn Asn
                85                  90                  95

Asn Asp Ser Gly Glu Tyr Thr Cys Gln Thr Gly Gln Thr Ser Leu Ser
            100                 105                 110

Asp Pro Val His Leu Thr Val Leu Ser Glu Trp Leu Val Leu Gln Thr
        115                 120                 125

Pro His Leu Glu Phe Gln Glu Gly Glu Thr Ile Met Leu Arg Cys His
    130                 135                 140

Ser Trp Lys Asp Lys Pro Leu Val Lys Val Thr Phe Phe Gln Asn Gly
145                 150                 155                 160

Lys Ser Gln Lys Phe Ser Arg Leu Asp Pro Thr Phe Ser Ile Pro Gln
                165                 170                 175

Ala Asn His Ser His Ser Gly Asp Tyr His Cys Thr Gly Asn Ile Gly
            180                 185                 190

Tyr Thr Leu Phe Ser Ser Lys Pro Val Thr Ile Thr Val Gln Val Pro
        195                 200                 205

Ser Met Gly Ser Ser Ser Pro Met Gly Ile Ile Val Ala Val Val Ile
    210                 215                 220

Ala Thr Ala Val Ala Ala Ile Val Ala Ala Val Val Ala Leu Ile Tyr
225                 230                 235                 240

Cys Arg Lys Lys Arg Ile Ser Ala Asn Ser Thr Asp Pro Val Lys Ala
                245                 250                 255

Ala Gln Phe Glu Pro Pro Gly Arg Gln Met Ile Ala Ile Arg Lys Arg
            260                 265                 270

Gln Leu Glu Glu Thr Asn Asn Asp Tyr Glu Thr Ala Asp Gly Gly Tyr
        275                 280                 285

Met Thr Leu Asn Pro Arg Ala Pro Thr Asp Asp Lys Asn Ile Tyr
    290                 295                 300

Leu Thr Leu Pro Pro Asn Asp His Val Asn Ser Asn Asn
305                 310                 315
```

```
<210> SEQ ID NO 17
<211> LENGTH: 316
<212> TYPE: PRT
<213> ORGANISM: Chimp
<220> FEATURE:
<221> NAME/KEY: MISC_FEATURE
<222> LOCATION: (1)..(316)
<223> OTHER INFORMATION: FcgammaRIIA

<400> SEQUENCE: 17

Met Ala Met Glu Thr Gln Met Ser Gln Asn Val Cys Pro Arg Asn Leu
1               5                  10                  15

Trp Leu Leu Gln Pro Leu Thr Val Leu Leu Leu Leu Ala Ser Ala Asp
            20                  25                  30

Ser Gln Ala Ala Pro Pro Lys Ala Val Leu Lys Leu Glu Pro Pro Trp
        35                  40                  45

Ile Asn Val Leu Gln Glu Asp Ser Val Thr Leu Thr Cys Arg Gly Ala
50                  55                  60

Arg Ser Pro Glu Ser Asp Ser Ile Gln Trp Phe His Asn Gly Asn Leu
65                  70                  75                  80

Ile Pro Thr His Thr Gln Pro Ser Tyr Arg Phe Lys Ala Asn Asn Asn
                85                  90                  95

Asp Ser Gly Glu Tyr Thr Cys Gln Thr Gly Gln Thr Ser Leu Ser Asp
            100                 105                 110

Pro Val His Leu Thr Val Leu Ser Glu Trp Leu Val Leu Gln Thr Pro
        115                 120                 125

His Leu Glu Phe Gln Glu Gly Glu Thr Ile Val Leu Arg Cys His Ser
    130                 135                 140

Trp Lys Asp Lys Pro Leu Val Lys Val Thr Phe Phe Gln Asn Gly Lys
145                 150                 155                 160

Ser Gln Lys Phe Ser His Leu Asp Pro Asn Leu Ser Ile Pro Gln Ala
                165                 170                 175

Asn His Ser His Ser Gly Asp Tyr His Cys Thr Gly Asn Ile Gly Tyr
            180                 185                 190

Thr Leu Phe Ser Ser Lys Pro Val Thr Ile Thr Val Gln Ala Pro Ser
        195                 200                 205

Val Gly Ser Ser Ser Pro Val Gly Ile Ile Val Ala Val Val Ile Ala
    210                 215                 220

Thr Ala Val Ala Ala Ile Val Ala Ala Val Val Ala Leu Ile Tyr Cys
225                 230                 235                 240

Arg Lys Lys Arg Ile Ser Ala Asn Ser Thr Asp Pro Val Lys Ala Ala
                245                 250                 255

Gln Phe Glu Pro Pro Gly Arg Gln Met Ile Ala Ile Arg Lys Arg Gln
            260                 265                 270

Leu Glu Glu Thr Asn Asn Asp Tyr Glu Thr Ala Asp Gly Gly Tyr Met
        275                 280                 285

Thr Leu Asn Pro Arg Ala Pro Thr Asp Asp Lys Asn Ile Tyr Leu
    290                 295                 300

Thr Leu Pro Pro Asn Asp His Val Asn Ser Asn Asn
305                 310                 315

<210> SEQ ID NO 18
<211> LENGTH: 294
<212> TYPE: PRT
<213> ORGANISM: Cynomolgus
<220> FEATURE:
```

```
<221> NAME/KEY: MISC_FEATURE
<222> LOCATION: (1)..(294)
<223> OTHER INFORMATION: FcgammaRIIB

<400> SEQUENCE: 18
```

| | | | | | | | | | | | | | | |
|---|---|---|---|---|---|---|---|---|---|---|---|---|---|---|
| Met | Gly | Ile | Leu | Ser | Phe | Leu | Pro | Val | Leu | Ala | Thr | Glu | Ser | Asp | Trp |
| 1 | | | | 5 | | | | | 10 | | | | | 15 | |
| Ala | Asp | Cys | Lys | Ser | Ser | Gln | Pro | Trp | Gly | His | Met | Leu | Leu | Trp | Thr |
| | | | 20 | | | | | 25 | | | | | 30 | | |
| Ala | Val | Leu | Phe | Leu | Ala | Pro | Val | Ala | Gly | Thr | Pro | Ala | Ala | Pro | Pro |
| | | | 35 | | | | 40 | | | | | 45 | | | |
| Lys | Ala | Val | Leu | Lys | Leu | Glu | Pro | Pro | Trp | Ile | Asn | Val | Leu | Arg | Glu |
| | 50 | | | | | 55 | | | | | 60 | | | | |
| Asp | Ser | Val | Thr | Leu | Thr | Cys | Gly | Gly | Ala | His | Ser | Pro | Asp | Ser | Asp |
| 65 | | | | 70 | | | | | 75 | | | | | 80 | |
| Ser | Thr | Gln | Trp | Phe | His | Asn | Gly | Asn | Leu | Ile | Pro | Thr | His | Thr | Gln |
| | | | | 85 | | | | | 90 | | | | | 95 | |
| Pro | Ser | Tyr | Arg | Phe | Lys | Ala | Asn | Asn | Asn | Asp | Ser | Gly | Glu | Tyr | Arg |
| | | | 100 | | | | | 105 | | | | | 110 | | |
| Cys | Gln | Thr | Gly | Arg | Thr | Ser | Leu | Ser | Asp | Pro | Val | His | Leu | Thr | Val |
| | | | 115 | | | | | 120 | | | | | 125 | | |
| Leu | Ser | Glu | Trp | Leu | Ala | Leu | Gln | Thr | Pro | His | Leu | Glu | Phe | Arg | Glu |
| | 130 | | | | | 135 | | | | | 140 | | | | |
| Gly | Glu | Thr | Ile | Leu | Leu | Arg | Cys | His | Ser | Trp | Lys | Asp | Lys | Pro | Leu |
| 145 | | | | | 150 | | | | | 155 | | | | | 160 |
| Ile | Lys | Val | Thr | Phe | Phe | Gln | Asn | Gly | Ile | Ser | Lys | Lys | Phe | Ser | His |
| | | | | 165 | | | | | 170 | | | | | 175 | |
| Met | Asn | Pro | Asn | Phe | Ser | Ile | Pro | Gln | Ala | Asn | His | Ser | His | Ser | Gly |
| | | | 180 | | | | | 185 | | | | | 190 | | |
| Asp | Tyr | His | Cys | Thr | Gly | Asn | Ile | Gly | Tyr | Thr | Pro | Tyr | Ser | Ser | Lys |
| | | | 195 | | | | | 200 | | | | | 205 | | |
| Pro | Val | Thr | Ile | Thr | Val | Gln | Val | Pro | Ser | Met | Gly | Ser | Ser | Ser | Pro |
| | 210 | | | | | 215 | | | | | 220 | | | | |
| Ile | Gly | Ile | Ile | Val | Ala | Val | Val | Thr | Gly | Ile | Ala | Val | Ala | Ala | Ile |
| 225 | | | | | 230 | | | | | 235 | | | | | 240 |
| Val | Ala | Ala | Val | Val | Ala | Leu | Ile | Tyr | Cys | Arg | Lys | Lys | Arg | Ile | Ser |
| | | | | 245 | | | | | 250 | | | | | 255 | |
| Ala | Asn | Pro | Thr | Asn | Pro | Asp | Glu | Ala | Asp | Lys | Val | Gly | Ala | Glu | Asn |
| | | | 260 | | | | | 265 | | | | | 270 | | |
| Thr | Ile | Thr | Tyr | Ser | Leu | Leu | Met | His | Pro | Asp | Ala | Leu | Glu | Glu | Pro |
| | | | 275 | | | | | 280 | | | | | 285 | | |
| Asp | Asp | Gln | Asn | Arg | Val | | | | | | | | | | |
| | | | 290 | | | | | | | | | | | | |

```
<210> SEQ ID NO 19
<211> LENGTH: 291
<212> TYPE: PRT
<213> ORGANISM: Homo sapiens
<220> FEATURE:
<221> NAME/KEY: MISC_FEATURE
<222> LOCATION: (1)..(291)
<223> OTHER INFORMATION: FcgammaRIIB

<400> SEQUENCE: 19
```

| | | | | | | | | | | | | | | | |
|---|---|---|---|---|---|---|---|---|---|---|---|---|---|---|---|
| Met | Gly | Ile | Leu | Ser | Phe | Leu | Pro | Val | Leu | Ala | Thr | Glu | Ser | Asp | Trp |
| 1 | | | | 5 | | | | | 10 | | | | | 15 | |
| Ala | Asp | Cys | Lys | Ser | Pro | Gln | Pro | Trp | Gly | His | Met | Leu | Leu | Trp | Thr |

-continued

```
                20                  25                  30
Ala Val Leu Phe Leu Ala Pro Val Ala Gly Thr Pro Ala Pro Pro
            35                  40                  45
Lys Ala Val Leu Lys Leu Glu Pro Gln Trp Ile Asn Val Leu Gln Glu
50                      55                      60
Asp Ser Val Thr Leu Thr Cys Arg Gly Thr His Ser Pro Glu Ser Asp
65                      70                      75                      80
Ser Ile Gln Trp Phe His Asn Gly Asn Leu Ile Pro Thr His Thr Gln
                    85                      90                      95
Pro Ser Tyr Arg Phe Lys Ala Asn Asn Asn Asp Ser Gly Glu Tyr Thr
                100                     105                     110
Cys Gln Thr Gly Gln Thr Ser Leu Ser Asp Pro Val His Leu Thr Val
                115                     120                     125
Leu Ser Glu Trp Leu Val Leu Gln Thr Pro His Leu Glu Phe Gln Glu
                130                     135                 140
Gly Glu Thr Ile Val Leu Arg Cys His Ser Trp Lys Asp Lys Pro Leu
145                     150                     155                     160
Val Lys Val Thr Phe Phe Gln Asn Gly Lys Ser Lys Lys Phe Ser Arg
                    165                     170                     175
Ser Asp Pro Asn Phe Ser Ile Pro Gln Ala Asn His Ser His Ser Gly
                180                     185                     190
Asp Tyr His Cys Thr Gly Asn Ile Gly Tyr Thr Leu Tyr Ser Ser Lys
                195                     200                     205
Pro Val Thr Ile Thr Val Gln Ala Pro Ser Ser Pro Met Gly Ile
                210                     215                     220
Ile Val Ala Val Val Thr Gly Ile Ala Val Ala Ala Ile Val Ala Ala
225                     230                     235                     240
Val Val Ala Leu Ile Tyr Cys Arg Lys Lys Arg Ile Ser Ala Asn Pro
                    245                     250                     255
Thr Asn Pro Asp Glu Ala Asp Lys Val Gly Ala Glu Asn Thr Ile Thr
                260                     265                     270
Tyr Ser Leu Leu Met His Pro Asp Ala Leu Glu Glu Pro Asp Asp Gln
                275                     280                     285
Asn Arg Ile
    290
```

<210> SEQ ID NO 20
<211> LENGTH: 254
<212> TYPE: PRT
<213> ORGANISM: Cynomolgus
<220> FEATURE:
<221> NAME/KEY: MISC_FEATURE
<222> LOCATION: (1)..(254)
<223> OTHER INFORMATION: FcgammaRIIIA

<400> SEQUENCE: 20

```
Met Trp Gln Leu Leu Leu Pro Thr Ala Leu Leu Leu Val Ser Ala
1               5                   10                  15
Gly Met Arg Ala Glu Asp Leu Pro Lys Ala Val Val Phe Leu Glu Pro
                20                  25                  30
Gln Trp Tyr Arg Val Leu Glu Lys Asp Arg Val Thr Leu Lys Cys Gln
                35                  40                  45
Gly Ala Tyr Ser Pro Glu Asp Asn Ser Thr Arg Trp Phe His Asn Glu
            50                  55                      60
Ser Leu Ile Ser Ser Gln Thr Ser Ser Tyr Phe Ile Ala Ala Ala Arg
65                  70                      75                      80
```

-continued

```
Val Asn Asn Ser Gly Glu Tyr Arg Cys Gln Thr Ser Leu Ser Thr Leu
            85                  90                  95

Ser Asp Pro Val Gln Leu Glu Val His Ile Gly Trp Leu Leu Leu Gln
            100                 105                 110

Ala Pro Arg Trp Val Phe Lys Glu Glu Ser Ile His Leu Arg Cys
        115                 120                 125

His Ser Trp Lys Asn Thr Leu Leu His Lys Val Thr Tyr Leu Gln Asn
    130                 135                 140

Gly Lys Gly Arg Lys Tyr Phe His Gln Asn Ser Asp Phe Tyr Ile Pro
145                 150                 155                 160

Lys Ala Thr Leu Lys Asp Ser Gly Ser Tyr Phe Cys Arg Gly Leu Ile
                165                 170                 175

Gly Ser Lys Asn Val Ser Ser Glu Thr Val Asn Ile Thr Ile Thr Gln
                180                 185                 190

Asp Leu Ala Val Ser Ser Ile Ser Ser Phe Phe Pro Pro Gly Tyr Gln
                195                 200                 205

Val Ser Phe Cys Leu Val Met Val Leu Leu Phe Ala Val Asp Thr Gly
            210                 215                 220

Leu Tyr Phe Ser Met Lys Lys Ser Ile Pro Ser Ser Thr Arg Asp Trp
225                 230                 235                 240

Glu Asp His Lys Phe Lys Trp Ser Lys Asp Pro Gln Asp Lys
                245                 250

<210> SEQ ID NO 21
<211> LENGTH: 254
<212> TYPE: PRT
<213> ORGANISM: Homo sapiens
<220> FEATURE:
<221> NAME/KEY: MISC_FEATURE
<222> LOCATION: (1)..(254)
<223> OTHER INFORMATION: FcgammaRIIIA

<400> SEQUENCE: 21

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175
```

```
Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 22
<211> LENGTH: 933
<212> TYPE: DNA
<213> ORGANISM: Chimp
<220> FEATURE:
<221> NAME/KEY: misc_feature
<222> LOCATION: (1)..(933)
<223> OTHER INFORMATION: FcgammaRIIA

<400> SEQUENCE: 22
atgtctcaga atgtatgtcc cagaaacctg tggctgcttc aaccattgac agttttgctg      60
ctgctggctt ctgcagacag tcaagctgct cccccaaagg ctgtgctgaa acttgagccc     120
ccgtggatca acgtgctcca ggaggactct gtgactctga catgccgggg ggctcgcagc     180
cctgagagcg actccattca gtggttccac aatgggaatc tcatccccac ccacacgcag     240
cccagctaca ggttcaaggc caacaacaat gacagcgggg agtacacgtg ccagactggc     300
cagaccagcc tcagcgaccc tgtgcatctg actgtgcttt ccgaatggct ggtgctccag     360 accccctcacc tggagttcca ggagggagaa accatcgtgc tgaggtgcca cagctggaag     420
gacaagcctc tggtcaaggt cacattcttc cagaatggaa atcccagaa attctcccat     480 ttggatccca acctctccat cccacaagca accacagtc acagtggtga ttaccactgc     540
acaggaaaca taggctacac gctgttctca tccaagcctg tgaccatcac tgtccaagcg     600
cccagcgtgg gcagctcttc accagtgggg atcattgtgg ctgtggtcat tgcgactgct     660
gtagcagcca ttgttgctgc tgtagtggcc ttgatctact gcaggaaaaa gcggatttca     720
gccaattcca ctgatcctgt gaaggctgcc caatttgagc cacctggacg tcaaatgatt     780
gccatcagaa agagacaact tgaagaaacc aacaatgact atgaaacagc tgacggcggc     840
tacatgactc tgaaccccag ggcacctact gacgatgata aaaacatcta cctgactctt     900
cctcccaacg accatgtcaa cagtaataac taa                                   933

<210> SEQ ID NO 23
<211> LENGTH: 360
<212> TYPE: DNA
<213> ORGANISM: Cynomolgus
<220> FEATURE:
<221> NAME/KEY: misc_feature
<222> LOCATION: (1)..(360)
<223> OTHER INFORMATION: B-2 microglobulin

<400> SEQUENCE: 23
atgtctccct cagtggcctt agccgtgctg gcgctactct ctctttctgg cctggaggct      60
atccagcgta ctccaaagat tcaggtttac tcacgccatc caccagagaa tggaaagcca     120
aatttcctga attgctatgt gtctggattt catccatctg atattgaagt tgacttactg     180
aagaatggag agaaaatggg aaaagtggag cattcagact tgtctttcag caaagactgg     240
```

```
tctttctatc tcttgtacta cactgaattc accccaatg aaaaagatga gtatgcctgc      300
cgtgtgaacc atgtgacttt gtcagggccc aggacagtta agtgggatcg agacatgtaa    360
```

<210> SEQ ID NO 24
<211> LENGTH: 360
<212> TYPE: DNA
<213> ORGANISM: Homo sapiens
<220> FEATURE:
<221> NAME/KEY: misc_feature
<222> LOCATION: (1)..(360)
<223> OTHER INFORMATION: B-2 microglobulin

<400> SEQUENCE: 24

```
atgtctcgct ccgtggcctt agctgtgctc gcgctactct ctctttctgg cctggaggct     60
atccagcgta ctccaaagat tcaggtttac tcacgtcatc cagcagagaa tggaaagtca    120
aatttcctga attgctatgt gtctgggttt catccatccg acattgaagt tgacttactg    180
aagaatggag agagaattga aaagtggag cattcagact tgtctttcag caaggactgg    240
tctttctatc tcttgtacta cactgaattc accccactg aaaaagatga gtatgcctgc    300
cgtgtgaacc atgtgacttt gtcacagccc aagatagtta agtgggatcg agacatgtaa    360
```

<210> SEQ ID NO 25
<211> LENGTH: 119
<212> TYPE: PRT
<213> ORGANISM: Cynomolgus
<220> FEATURE:
<221> NAME/KEY: MISC_FEATURE
<222> LOCATION: (1)..(119)
<223> OTHER INFORMATION: Beta-2 microglobulin

<400> SEQUENCE: 25

```
Met Ser Pro Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Pro Glu Asn Gly Lys Pro Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Lys Met Gly Lys Val Glu His Ser Asp Leu Ser Phe Ser Lys Asp Trp
65                  70                  75                  80

Ser Phe Tyr Leu Leu Tyr Tyr Thr Glu Phe Thr Pro Asn Glu Lys Asp
                85                  90                  95

Glu Tyr Ala Cys Arg Val Asn His Val Thr Leu Ser Gly Pro Arg Thr
            100                 105                 110

Val Lys Trp Asp Arg Asp Met
        115
```

<210> SEQ ID NO 26
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: Beta-2 microglobulin

<400> SEQUENCE: 26

```
Met Ser Arg Ser Val Ala Leu Ala Val Leu Ala Leu Leu Ser Leu Ser
1               5                   10                  15
```

```
Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
            115
```

<210> SEQ ID NO 27
<211> LENGTH: 1098
<212> TYPE: DNA
<213> ORGANISM: Cynomolgus
<220> FEATURE:
<221> NAME/KEY: misc_feature
<222> LOCATION: (1)..(1098)
<223> OTHER INFORMATION: FcRn alpha-chain

<400> SEQUENCE: 27

```
atgagggtcc cgcggcctca gccctgggcg ctggggctcc tgctctttct cctgcccggg      60
agcctgggcg cagaaagcca cctctccctc ctgtaccacc tcaccgcggt gtcctcgccc     120
gccccgggga cgcctgcctt ctgggtgtcc ggctggctgg cccgcagca gtacctgagc      180
tacgacagcc tgaggggcca ggcggagccc tgtggagctt gggtctggga aaaccaagtg     240
tcctggtatt gggagaaaga gaccacagat ctgaggatca aggagaagct ctttctggaa     300
gctttcaaag ctttgggggg aaaaggcccc tacactctgc agggcctgct gggctgtgaa     360
ctgagccctg acaacacctc ggtgcccacc gccagttcg ccctgaacgg cgaggagttc     420
atgaatttcg acctcaagca gggcacctgg ggtggggact ggcccgaggc cctggctatc     480
agtcagcggt ggcagcagca ggacaaggcg ccaacaagg agctcacctt cctgctattc     540
tcctgcccac accggctgcg ggagcacctg gagaggggcc gtggaaacct ggagtggaag     600
gagcccccct ccatgcgcct gaaggcccga cccggcaacc tggcttttc cgtgcttacc     660
tgcagcgcct tctccttcta ccctccggaa ctgcaactgc ggttcctgcg gaatgggatg     720
gccgctggca ccggacaggg cgacttcggc cccaacagtg acggctcctt ccacgcctcg     780
tcgtcactaa cagtcaaaag tggcgatgag caccactact gctgcatcgt gcagcacgcg     840
gggctggcgc agcccctcag ggtggagctg gaaactccag ccaagtcctc ggtgctcgtg     900
gtgggaatcg tcatcggtgt cttgctactc acggcagcgg ctgtaggagg agctctgttg     960
tggagaagga tgaggagtgg gctgccagcc ccttggatct ccctccgtgg agatgacacc    1020
gggtccctcc tgcccacccc gggggaggcc caggatgctg attcgaagga tataaatgtg    1080
atcccagcca ctgcctga                                                  1098
```

<210> SEQ ID NO 28
<211> LENGTH: 1098
<212> TYPE: DNA
<213> ORGANISM: Homo sapiens
<220> FEATURE:
<221> NAME/KEY: misc_feature
<222> LOCATION: (1)..(1098)

-continued

<223> OTHER INFORMATION: FcRn alpha-chain

<400> SEQUENCE: 28

```
atggggtcc  cgcggcctca  gccctgggcg  ctggggctcc  tgctctttct  ccttcctggg      60
agcctgggcg  cagaaagcca  cctctcccctc  ctgtaccacc  ttaccgcggt  gtcctcgcct    120
gccccgggga  ctcctgcctt  ctgggtgtcc  ggctggctgg  gcccgcagca  gtacctgagc    180
tacaatagcc  tgcggggcga  ggcggagccc  tgtggagctt  gggtctggga  aaaccaggtg    240
tcctggtatt  gggagaaaga  gaccacagat  ctgaggatca  aggagaagct  ctttctggaa    300
gctttcaaag  ctttggggg  aaaaggtccc  tacactctgc  agggcctgct  gggctgtgaa    360
ctgggccctg  acaacacctc  ggtgcccacc  gccaagttcg  ccctgaacgg  cgaggagttc    420
atgaatttcg  acctcaagca  gggcacctgg  ggtggggact  ggcccgaggc  cctggctatc    480
agtcagcggt  ggcagcagca  ggacaaggcg  gccaacaagg  agctcacctt  cctgctattc    540
tcctgcccgc  accgctgcg  ggagcacctg  gagaggggcc  gcggaaacct  ggagtggaag    600
gagccccct  ccatgcgcct  gaaggcccga  cccagcagcc  ctggcttttc  cgtgcttacc    660
tgcagcgcct  tctccttcta  ccctccggag  ctgcaactcc  ggttcctgcg  gaatgggctg    720
gccgctggca  ccggccaggg  tgacttcggc  cccaacagtg  acggatcctt  ccacgcctcg    780
tcgtcactaa  cagtcaaaag  tggcgatgag  caccactact  gctgcattgt  gcagcacgcg    840
gggctggcgc  agcccctcag  ggtggagctg  gaatctccag  ccaagtcctc  cgtgctcgtg    900
gtgggaatcg  tcatcggtgt  cttgctactc  acggcagcgg  ctgtaggagg  agctctgttg    960
tggagaagga  tgaggagtgg  gctgccagcc  ccttggatct  cccttcgtgg  agacgacacc   1020
gggtcctcc  tgcccacccc  aggggaggcc  caggatgctg  atttgaagga  tgtaaatgtg   1080
attccagcca  ccgcctga                                                    1098
```

<210> SEQ ID NO 29
<211> LENGTH: 365
<212> TYPE: PRT
<213> ORGANISM: Cynomolgus
<220> FEATURE:
<221> NAME/KEY: MISC_FEATURE
<222> LOCATION: (1)..(365)
<223> OTHER INFORMATION: FcRn (S3)

<400> SEQUENCE: 29

```
Met Arg Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
            20                  25                  30

His Leu Thr Ala Val Ser Ser Pro Ala Pro Gly Thr Pro Ala Phe Trp
        35                  40                  45

Val Ser Gly Trp Leu Gly Pro Gln Gln Tyr Leu Ser Tyr Asp Ser Leu
    50                  55                  60

Arg Gly Gln Ala Glu Pro Cys Gly Ala Trp Val Trp Glu Asn Gln Val
65                  70                  75                  80

Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Gly Lys Gly Pro Tyr Thr
            100                 105                 110

Leu Gln Gly Leu Leu Gly Cys Glu Leu Ser Pro Asp Asn Thr Ser Val
        115                 120                 125

Pro Thr Ala Lys Phe Ala Leu Asn Gly Glu Glu Phe Met Asn Phe Asp
```

-continued

```
                130                 135                 140
Leu Lys Gln Gly Thr Trp Gly Gly Asp Trp Pro Glu Ala Leu Ala Ile
145                 150                 155                 160

Ser Gln Arg Trp Gln Gln Gln Asp Lys Ala Ala Asn Lys Glu Leu Thr
                165                 170                 175

Phe Leu Leu Phe Ser Cys Pro His Arg Leu Arg Glu His Leu Glu Arg
                180                 185                 190

Gly Arg Gly Asn Leu Glu Trp Lys Glu Pro Pro Ser Met Arg Leu Lys
                195                 200                 205

Ala Arg Pro Gly Asn Pro Gly Phe Ser Val Leu Thr Cys Ser Ala Phe
                210                 215                 220

Ser Phe Tyr Pro Pro Glu Leu Gln Leu Arg Phe Leu Arg Asn Gly Met
225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
                260                 265                 270

Tyr Cys Cys Ile Val Gln His Ala Gly Leu Ala Gln Pro Leu Arg Val
                275                 280                 285

Glu Leu Glu Thr Pro Ala Lys Ser Ser Val Leu Val Val Gly Ile Val
                290                 295                 300

Ile Gly Val Leu Leu Leu Thr Ala Ala Ala Val Gly Gly Ala Leu Leu
305                 310                 315                 320

Trp Arg Arg Met Arg Ser Gly Leu Pro Ala Pro Trp Ile Ser Leu Arg
                325                 330                 335

Gly Asp Asp Thr Gly Ser Leu Leu Pro Thr Pro Gly Glu Ala Gln Asp
                340                 345                 350

Ala Asp Ser Lys Asp Ile Asn Val Ile Pro Ala Thr Ala
                355                 360                 365

<210> SEQ ID NO 30
<211> LENGTH: 365
<212> TYPE: PRT
<213> ORGANISM: Homo sapiens
<220> FEATURE:
<221> NAME/KEY: MISC_FEATURE
<222> LOCATION: (1)..(365)
<223> OTHER INFORMATION: FcRn alpha-chain

<400> SEQUENCE: 30

Met Gly Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
                20                  25                  30

His Leu Thr Ala Val Ser Ser Pro Ala Pro Gly Thr Pro Ala Phe Trp
                35                  40                  45

Val Ser Gly Trp Leu Gly Pro Gln Gln Tyr Leu Ser Tyr Asn Ser Leu
                50                  55                  60

Arg Gly Glu Ala Glu Pro Cys Gly Ala Trp Val Trp Glu Asn Gln Val
65                  70                  75                  80

Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Gly Lys Gly Pro Tyr Thr
                100                 105                 110

Leu Gln Gly Leu Leu Gly Cys Glu Leu Gly Pro Asp Asn Thr Ser Val
                115                 120                 125
```

```
Pro Thr Ala Lys Phe Ala Leu Asn Gly Glu Glu Phe Met Asn Phe Asp
    130                 135                 140
Leu Lys Gln Gly Thr Trp Gly Asp Trp Pro Glu Ala Leu Ala Ile
145                 150                 155                 160
Ser Gln Arg Trp Gln Gln Asp Lys Ala Ala Asn Lys Glu Leu Thr
                165                 170                 175
Phe Leu Leu Phe Ser Cys Pro His Arg Leu Arg Glu His Leu Glu Arg
                180                 185                 190
Gly Arg Gly Asn Leu Glu Trp Lys Glu Pro Pro Ser Met Arg Leu Lys
            195                 200                 205
Ala Arg Pro Ser Ser Pro Gly Phe Ser Val Leu Thr Cys Ser Ala Phe
    210                 215                 220
Ser Phe Tyr Pro Pro Glu Leu Gln Leu Arg Phe Leu Arg Asn Gly Leu
225                 230                 235                 240
Ala Ala Gly Thr Gly Gln Gly Asp Phe Gly Pro Asn Ser Asp Gly Ser
                245                 250                 255
Phe His Ala Ser Ser Ser Leu Thr Val Lys Ser Gly Asp Glu His His
                260                 265                 270
Tyr Cys Cys Ile Val Gln His Ala Gly Leu Ala Gln Pro Leu Arg Val
            275                 280                 285
Glu Leu Glu Ser Pro Ala Lys Ser Ser Val Leu Val Gly Ile Val
    290                 295                 300
Ile Gly Val Leu Leu Leu Thr Ala Ala Ala Val Gly Gly Ala Leu Leu
305                 310                 315                 320
Trp Arg Arg Met Arg Ser Gly Leu Pro Ala Pro Trp Ile Ser Leu Arg
                325                 330                 335
Gly Asp Asp Thr Gly Val Leu Leu Pro Thr Pro Gly Glu Ala Gln Asp
                340                 345                 350
Ala Asp Leu Lys Asp Val Asn Val Ile Pro Ala Thr Ala
            355                 360                 365

<210> SEQ ID NO 31
<211> LENGTH: 33
<212> TYPE: DNA
<213> ORGANISM: Cynomolgus
<220> FEATURE:
<221> NAME/KEY: misc_feature
<222> LOCATION: (1)..(33)
<223> OTHER INFORMATION: FcgammaRI - forward primer

<400> SEQUENCE: 31
caggtcaatc tctagactcc caccagcttg gag                              33

<210> SEQ ID NO 32
<211> LENGTH: 33
<212> TYPE: DNA
<213> ORGANISM: Cynomolgus
<220> FEATURE:
<221> NAME/KEY: misc_feature
<222> LOCATION: (1)..(33)
<223> OTHER INFORMATION: FcgammaRI - reverse primer

<400> SEQUENCE: 32
ggtcaactat aagcttggac ggtccagatc gat                              33

<210> SEQ ID NO 33
<211> LENGTH: 34
<212> TYPE: DNA
<213> ORGANISM: Cynomolgus
```

```
<220> FEATURE:
<221> NAME/KEY: misc_feature
<222> LOCATION: (1)..(34)
<223> OTHER INFORMATION: FcgammaRI-H6-GST - forward primer

<400> SEQUENCE: 33
caggtcaatc atcgatatgt ggttcttgac agct                               34

<210> SEQ ID NO 34
<211> LENGTH: 51
<212> TYPE: DNA
<213> ORGANISM: Cynomolgus
<220> FEATURE:
<221> NAME/KEY: misc_feature
<222> LOCATION: (1)..(51)
<223> OTHER INFORMATION: FcgammaRI-H6-GST - reverse primer

<400> SEQUENCE: 34
ggtcaactat gctagcatgg tgatgatggt ggtgccagac aggagttggt a            51

<210> SEQ ID NO 35
<211> LENGTH: 36
<212> TYPE: DNA
<213> ORGANISM: Cynomolgus
<220> FEATURE:
<221> NAME/KEY: misc_feature
<222> LOCATION: (1)..(36)
<223> OTHER INFORMATION: FcgammaRIIB - forward primer

<400> SEQUENCE: 35
caggtcaatc tctagaatgg gaatcctgtc attctt                             36

<210> SEQ ID NO 36
<211> LENGTH: 34
<212> TYPE: DNA
<213> ORGANISM: Cynomolgus
<220> FEATURE:
<221> NAME/KEY: misc_feature
<222> LOCATION: (1)..(34)
<223> OTHER INFORMATION: FcgammaRIIB - reverse primer

<400> SEQUENCE: 36
ggtcaactat aagcttctaa atacggttct ggtc                               34

<210> SEQ ID NO 37
<211> LENGTH: 33
<212> TYPE: DNA
<213> ORGANISM: Cynomolgus
<220> FEATURE:
<221> NAME/KEY: misc_feature
<222> LOCATION: (1)..(33)
<223> OTHER INFORMATION: FcgammaRIIB-H6-GST - forward primer

<400> SEQUENCE: 37
caggtcaatc atcgatatgc ttctgtggac agc                                33

<210> SEQ ID NO 38
<211> LENGTH: 34
<212> TYPE: DNA
<213> ORGANISM: Cynomolgus
<220> FEATURE:
<221> NAME/KEY: misc_feature
<222> LOCATION: (1)..(34)
<223> OTHER INFORMATION: FcgammaRIIB-H6-GST - reverse primer

<400> SEQUENCE: 38
ggtcaactat ggtgacctat cggtgaagag ctgc                               34
```

```
<210> SEQ ID NO 39
<211> LENGTH: 33
<212> TYPE: DNA
<213> ORGANISM: Cynomolgus
<220> FEATURE:
<221> NAME/KEY: misc_feature
<222> LOCATION: (1)..(33)
<223> OTHER INFORMATION: FcgammaRIIIA - forward primer

<400> SEQUENCE: 39
caggtcaatc tctagaatgt ggcagctgct cct                            33

<210> SEQ ID NO 40
<211> LENGTH: 33
<212> TYPE: DNA
<213> ORGANISM: Cynomolgus
<220> FEATURE:
<221> NAME/KEY: misc_feature
<222> LOCATION: (1)..(33)
<223> OTHER INFORMATION: FcgammaRIIIA - reverse primer

<400> SEQUENCE: 40
tcaactataa gcttatgttc agagatgctg ctg                            33

<210> SEQ ID NO 41
<211> LENGTH: 33
<212> TYPE: DNA
<213> ORGANISM: Cynomolgus
<220> FEATURE:
<221> NAME/KEY: misc_feature
<222> LOCATION: (1)..(33)
<223> OTHER INFORMATION: FcgammaRIIIA-H6-GST - forward primer

<400> SEQUENCE: 41
caggtcaatc tctagaatgt ggcagctgct cct                            33

<210> SEQ ID NO 42
<211> LENGTH: 35
<212> TYPE: DNA
<213> ORGANISM: Cynomolgus
<220> FEATURE:
<221> NAME/KEY: misc_feature
<222> LOCATION: (1)..(35)
<223> OTHER INFORMATION: FcgammaRIIIA-H6-GST - reverse primer

<400> SEQUENCE: 42
ggtcaactat ggtcaccttg gtacccaggt ggaaa                          35

<210> SEQ ID NO 43
<211> LENGTH: 45
<212> TYPE: DNA
<213> ORGANISM: Cynomolgus
<220> FEATURE:
<221> NAME/KEY: misc_feature
<222> LOCATION: (1)..(45)
<223> OTHER INFORMATION: Fc gamma - forward primer

<400> SEQUENCE: 43
caggtcaatc atcgatgaat tcccaccatg attccagcag tggtc               45

<210> SEQ ID NO 44
<211> LENGTH: 35
<212> TYPE: DNA
<213> ORGANISM: Cynomolgus
<220> FEATURE:
<221> NAME/KEY: misc_feature
<222> LOCATION: (1)..(35)
<223> OTHER INFORMATION: Fc gamma - reverse primer
```

<400> SEQUENCE: 44
ggtcaactat aagcttctac tgtggtggtt tctca                             35

<210> SEQ ID NO 45
<211> LENGTH: 32
<212> TYPE: DNA
<213> ORGANISM: Cynomolgus
<220> FEATURE:
<221> NAME/KEY: misc_feature
<222> LOCATION: (1)..(32)
<223> OTHER INFORMATION: B-2 microglobulin - forward primer

<400> SEQUENCE: 45
caggtcaatc atcgattcgg gccgagatgt ct                               32

<210> SEQ ID NO 46
<211> LENGTH: 34
<212> TYPE: DNA
<213> ORGANISM: Cynomolgus
<220> FEATURE:
<221> NAME/KEY: misc_feature
<222> LOCATION: (1)..(34)
<223> OTHER INFORMATION: B-2 microglobulin - reverse primer

<400> SEQUENCE: 46
ggtcaactat tctagattac atgtctcgat ccca                             34

<210> SEQ ID NO 47
<211> LENGTH: 35
<212> TYPE: DNA
<213> ORGANISM: Cynomolgus
<220> FEATURE:
<221> NAME/KEY: misc_feature
<222> LOCATION: (1)..(35)
<223> OTHER INFORMATION: FcgammaRIIA - forward primer

<400> SEQUENCE: 47
caggtcaatc tctagaatgt ctcagaatgt atgtc                            35

<210> SEQ ID NO 48
<211> LENGTH: 37
<212> TYPE: DNA
<213> ORGANISM: Cynomolgus
<220> FEATURE:
<221> NAME/KEY: misc_feature
<222> LOCATION: (1)..(37)
<223> OTHER INFORMATION: FcgammaRIIA - reverse primer

<400> SEQUENCE: 48
ggtcaactat aagcttttag ttattactgt tgtcata                          37

<210> SEQ ID NO 49
<211> LENGTH: 35
<212> TYPE: DNA
<213> ORGANISM: Cynomolgus
<220> FEATURE:
<221> NAME/KEY: misc_feature
<222> LOCATION: (1)..(35)
<223> OTHER INFORMATION: FcgammaRIIA-H6-GST - forward primer

<400> SEQUENCE: 49
caggtcaatc atcgatatgt ctcagaatgt atgtc                            35

<210> SEQ ID NO 50
<211> LENGTH: 34
<212> TYPE: DNA

```
<213> ORGANISM: Cynomolgus
<220> FEATURE:
<221> NAME/KEY: misc_feature
<222> LOCATION: (1)..(34)
<223> OTHER INFORMATION: FcgammaRIIA-H6-GST - reverse primer

<400> SEQUENCE: 50
ggtcaactat ggtgacccat cggtgaagag ctgc                             34

<210> SEQ ID NO 51
<211> LENGTH: 32
<212> TYPE: DNA
<213> ORGANISM: Cynomolgus
<220> FEATURE:
<221> NAME/KEY: misc_feature
<222> LOCATION: (1)..(32)
<223> OTHER INFORMATION: FcRn - forward primer

<400> SEQUENCE: 51
caggtcaatc atcgataggt cgtcctctca gc                               32

<210> SEQ ID NO 52
<211> LENGTH: 32
<212> TYPE: DNA
<213> ORGANISM: Cynomolgus
<220> FEATURE:
<221> NAME/KEY: misc_feature
<222> LOCATION: (1)..(32)
<223> OTHER INFORMATION: FcRn - reverse primer

<400> SEQUENCE: 52
ggtcaactat gaattctcgg aatggcggat gg                               32

<210> SEQ ID NO 53
<211> LENGTH: 32
<212> TYPE: DNA
<213> ORGANISM: Cynomolgus
<220> FEATURE:
<221> NAME/KEY: misc_feature
<222> LOCATION: (1)..(32)
<223> OTHER INFORMATION: FcRn-H6 - forward primer

<400> SEQUENCE: 53
caggtcaatc atcgataggt cgtcctctca gc                               32

<210> SEQ ID NO 54
<211> LENGTH: 55
<212> TYPE: DNA
<213> ORGANISM: Cynomolgus
<220> FEATURE:
<221> NAME/KEY: misc_feature
<222> LOCATION: (1)..(55)
<223> OTHER INFORMATION: FcRn-H6 - reverse primer

<400> SEQUENCE: 54
ggtcaactat gaattcatgg tgatgatggt ggtgcgagga cttggctgga gtttc       55

<210> SEQ ID NO 55
<211> LENGTH: 33
<212> TYPE: DNA
<213> ORGANISM: Artificial Sequence
<220> FEATURE:
<223> OTHER INFORMATION: PCR primer OF1

<400> SEQUENCE: 55
caggtcaatc tctagacagt ggttccacaa tgg                              33
```

```
<210> SEQ ID NO 56
<211> LENGTH: 35
<212> TYPE: DNA
<213> ORGANISM: artificial sequence
<220> FEATURE:
<223> OTHER INFORMATION: PCR primer OR1

<400> SEQUENCE: 56
ggtcaactat aagcttaaga gtcaggtaga tgttt                            35

<210> SEQ ID NO 57
<211> LENGTH: 37
<212> TYPE: DNA
<213> ORGANISM: artificial sequence
<220> FEATURE:
<223> OTHER INFORMATION: PCR primer OF2

<400> SEQUENCE: 57
caggtcaatc tctagaatac ataaccttat gtatcat                          37

<210> SEQ ID NO 58
<211> LENGTH: 37
<212> TYPE: DNA
<213> ORGANISM: artificial sequence
<220> FEATURE:
<223> OTHER INFORMATION: PCR primer OF3

<400> SEQUENCE: 58
caggtcaatc tctagatata gaataacatc cactttg                          37

<210> SEQ ID NO 59
<211> LENGTH: 32
<212> TYPE: DNA
<213> ORGANISM: artificial sequence
<220> FEATURE:
<223> OTHER INFORMATION: PCR primer OR2

<400> SEQUENCE: 59
ggtcaactat aagcttcaga gtcatgtagc cg                               32

<210> SEQ ID NO 60
<211> LENGTH: 35
<212> TYPE: DNA
<213> ORGANISM: artificial sequence
<220> FEATURE:
<223> OTHER INFORMATION: PCR primer OF4

<400> SEQUENCE: 60
caggtcaatc tctagaattc cactgatcct gtgaa                            35

<210> SEQ ID NO 61
<211> LENGTH: 37
<212> TYPE: DNA
<213> ORGANISM: artificial sequence
<220> FEATURE:
<223> OTHER INFORMATION: PCT primer OR3

<400> SEQUENCE: 61
ggtcaactat aagcttgctt tatttgtgaa atttgtg                          37

<210> SEQ ID NO 62
<211> LENGTH: 35
<212> TYPE: DNA
<213> ORGANISM: artificial sequence
<220> FEATURE:
<223> OTHER INFORMATION: PCR primer OF5
```

-continued

```
<400> SEQUENCE: 62
caggtcaatc tctagaactt ggacgtcaaa cgatt                                35

<210> SEQ ID NO 63
<211> LENGTH: 35
<212> TYPE: DNA
<213> ORGANISM: artificial sequence
<220> FEATURE:
<223> OTHER INFORMATION: PCR primer OR4

<400> SEQUENCE: 63
ggtcaactat aagcttctgc aataaacaag ttggg                                35

<210> SEQ ID NO 64
<211> LENGTH: 365
<212> TYPE: PRT
<213> ORGANISM: Cynomolgus
<220> FEATURE:
<221> NAME/KEY: MISC_FEATURE
<222> LOCATION: (1)..(365)
<223> OTHER INFORMATION: FcRn (N3)

<400> SEQUENCE: 64
```

Met Arg Val Pro Arg Pro Gln Pro Trp Ala Leu Gly Leu Leu Leu Phe
1               5                   10                  15

Leu Leu Pro Gly Ser Leu Gly Ala Glu Asn His Leu Ser Leu Leu Tyr
            20                  25                  30

His Leu Thr Ala Val Ser Ser Pro Ala Pro Gly Thr Pro Ala Phe Trp
        35                  40                  45

Val Ser Gly Trp Leu Gly Pro Gln Gln Tyr Leu Ser Tyr Asp Ser Leu
    50                  55                  60

Arg Gly Gln Ala Glu Pro Cys Gly Ala Trp Val Trp Glu Asn Gln Val
65                  70                  75                  80

Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Gly Lys Gly Pro Tyr Thr
            100                 105                 110

Leu Gln Gly Leu Leu Gly Cys Glu Leu Ser Pro Asp Asn Thr Ser Val
        115                 120                 125

Pro Thr Ala Lys Phe Ala Leu Asn Gly Glu Glu Phe Met Asn Phe Asp
    130                 135                 140

Leu Lys Gln Gly Thr Trp Gly Gly Asp Trp Pro Glu Ala Leu Ala Ile
145                 150                 155                 160

Ser Gln Arg Trp Gln Gln Gln Asp Lys Ala Ala Asn Lys Glu Leu Thr
                165                 170                 175

Phe Leu Leu Phe Ser Cys Pro His Arg Leu Arg Glu His Leu Glu Arg
            180                 185                 190

Gly Arg Gly Asn Leu Glu Trp Lys Glu Pro Pro Ser Met Arg Leu Lys
        195                 200                 205

Ala Arg Pro Gly Asn Pro Gly Phe Ser Val Leu Thr Cys Ser Ala Phe
    210                 215                 220

Ser Phe Tyr Pro Pro Glu Leu Gln Leu Arg Phe Leu Arg Asn Gly Met
225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
            260                 265                 270

```
Tyr Cys Cys Ile Val Gln His Ala Gly Leu Ala Gln Pro Leu Arg Val
        275                 280                 285

Glu Leu Glu Thr Pro Ala Lys Ser Ser Val Leu Val Val Gly Ile Val
        290                 295                 300

Ile Gly Val Leu Leu Thr Ala Ala Val Gly Gly Ala Leu Leu
305                 310                 315                 320

Trp Arg Arg Met Arg Ser Gly Leu Pro Ala Pro Trp Ile Ser Leu Arg
                325                 330                 335

Gly Asp Asp Thr Gly Ser Leu Leu Pro Thr Pro Gly Glu Ala Gln Asp
                340                 345                 350

Ala Asp Ser Lys Asp Ile Asn Val Ile Pro Ala Thr Ala
        355                 360                 365

<210> SEQ ID NO 65
<211> LENGTH: 336
<212> TYPE: PRT
<213> ORGANISM: Cynomolgus
<220> FEATURE:
<221> NAME/KEY: MISC_FEATURE
<222> LOCATION: (1)..(336)
<223> OTHER INFORMATION: FcgammaRI alpha-chain

<400> SEQUENCE: 65

Ala Val Ile Thr Leu Gln Pro Pro Trp Val Ser Val Phe Gln Glu Glu
1               5                   10                  15

Thr Val Thr Leu Gln Cys Glu Val Pro Arg Leu Pro Gly Ser Ser Ser
            20                  25                  30

Thr Gln Trp Phe Leu Asn Gly Thr Ala Thr Gln Thr Ser Thr Pro Ser
        35                  40                  45

Tyr Arg Ile Thr Ser Ala Ser Val Lys Asp Ser Gly Glu Tyr Arg Cys
    50                  55                  60

Gln Arg Gly Pro Ser Gly Arg Ser Asp Pro Ile Gln Leu Glu Ile His
65                  70                  75                  80

Arg Asp Trp Leu Leu Leu Gln Val Ser Ser Arg Val Phe Thr Glu Gly
                85                  90                  95

Glu Pro Leu Ala Leu Arg Cys His Ala Trp Lys Asp Lys Leu Val Tyr
            100                 105                 110

Asn Val Leu Tyr Tyr Gln Asn Gly Lys Ala Phe Lys Phe Phe Tyr Arg
        115                 120                 125

Asn Ser Gln Leu Thr Ile Leu Lys Thr Asn Ile Ser His Asn Gly Ala
    130                 135                 140

Tyr His Cys Ser Gly Met Gly Lys His Arg Tyr Thr Ser Ala Gly Val
145                 150                 155                 160

Ser Val Thr Val Lys Glu Leu Phe Pro Ala Pro Val Leu Asn Ala Ser
                165                 170                 175

Val Thr Ser Pro Leu Leu Glu Gly Asn Leu Val Thr Leu Ser Cys Glu
            180                 185                 190

Thr Lys Leu Leu Leu Gln Arg Pro Gly Leu Gln Leu Tyr Phe Ser Phe
        195                 200                 205

Tyr Met Gly Ser Lys Thr Leu Arg Gly Arg Asn Thr Ser Ser Glu Tyr
    210                 215                 220

Gln Ile Leu Thr Ala Arg Arg Glu Asp Ser Gly Phe Tyr Trp Cys Glu
225                 230                 235                 240

Ala Thr Thr Glu Asp Gly Asn Val Leu Lys Arg Ser Pro Glu Leu Glu
                245                 250                 255

Leu Gln Val Leu Gly Leu Gln Leu Pro Thr Pro Val Trp Leu His Val
```

```
                     260                 265                 270
Leu Phe Tyr Leu Val Val Gly Ile Met Phe Leu Val Asn Thr Val Leu
                275                 280                 285

Trp Val Thr Ile Arg Lys Glu Leu Lys Arg Lys Lys Lys Trp Asn Leu
            290                 295                 300

Glu Ile Ser Leu Asp Ser Ala His Glu Lys Lys Val Thr Ser Ser Leu
305                 310                 315                 320

Gln Glu Asp Arg His Leu Glu Glu Glu Leu Lys Ser Gln Glu Gln Glu
                    325                 330                 335

<210> SEQ ID NO 66
<211> LENGTH: 282
<212> TYPE: PRT
<213> ORGANISM: Cynomolgus
<220> FEATURE:
<221> NAME/KEY: MISC_FEATURE
<222> LOCATION: (1)..(282)
<223> OTHER INFORMATION: FcgammaRIIA

<400> SEQUENCE: 66

Thr Ala Pro Pro Lys Ala Val Leu Lys Leu Glu Pro Pro Trp Ile Asn
1               5                   10                  15

Val Leu Arg Glu Asp Ser Val Thr Leu Thr Cys Gly Gly Ala His Ser
            20                  25                  30

Pro Asp Ser Asp Ser Thr Gln Trp Phe His Asn Gly Asn Arg Ile Pro
        35                  40                  45

Thr His Thr Gln Pro Ser Tyr Arg Phe Lys Ala Asn Asn Asn Asp Ser
    50                  55                  60

Gly Glu Tyr Arg Cys Gln Thr Gly Arg Thr Ser Leu Ser Asp Pro Val
65                  70                  75                  80

His Leu Thr Val Leu Ser Glu Trp Leu Ala Leu Gln Thr Pro His Leu
                85                  90                  95

Glu Phe Arg Glu Gly Glu Thr Ile Met Leu Arg Cys His Ser Trp Lys
            100                 105                 110

Asp Lys Pro Leu Ile Lys Val Thr Phe Phe Gln Asn Gly Ile Ala Lys
        115                 120                 125

Lys Phe Ser His Met Asp Pro Asn Phe Ser Ile Pro Gln Ala Asn His
    130                 135                 140

Ser His Ser Gly Asp Tyr His Cys Thr Gly Asn Ile Gly Tyr Thr Pro
145                 150                 155                 160

Tyr Ser Ser Lys Pro Val Thr Ile Thr Val Gln Val Pro Ser Val Gly
                165                 170                 175

Ser Ser Ser Pro Met Gly Ile Ile Val Ala Val Val Thr Gly Ile Ala
            180                 185                 190

Val Ala Ala Ile Val Ala Ala Val Val Ala Leu Ile Tyr Cys Arg Lys
        195                 200                 205

Lys Arg Ile Ser Ala Asn Ser Thr Asp Pro Val Lys Ala Ala Arg Phe
    210                 215                 220

Glu Pro Leu Gly Arg Gln Thr Ile Ala Leu Arg Lys Arg Gln Leu Glu
225                 230                 235                 240

Glu Thr Asn Asn Asp Tyr Glu Thr Ala Asp Gly Gly Tyr Met Thr Leu
                245                 250                 255

Asn Pro Arg Ala Pro Thr Asp Asp Arg Asn Ile Tyr Leu Thr Leu
            260                 265                 270

Ser Pro Asn Asp Tyr Asp Asn Ser Asn
        275                 280
```

```
<210> SEQ ID NO 67
<211> LENGTH: 281
<212> TYPE: PRT
<213> ORGANISM: Chimp
<220> FEATURE:
<221> NAME/KEY: MISC_FEATURE
<222> LOCATION: (1)..(281)
<223> OTHER INFORMATION: FcgammaRIIA

<400> SEQUENCE: 67

Ala Pro Pro Lys Ala Val Leu Lys Leu Glu Pro Pro Trp Ile Asn Val
1               5                   10                  15

Leu Gln Glu Asp Ser Val Thr Leu Thr Cys Arg Gly Ala Arg Ser Pro
            20                  25                  30

Glu Ser Asp Ser Ile Gln Trp Phe His Asn Gly Asn Leu Ile Pro Thr
        35                  40                  45

His Thr Gln Pro Ser Tyr Arg Phe Lys Ala Asn Asn Asn Asp Ser Gly
    50                  55                  60

Glu Tyr Thr Cys Gln Thr Gly Gln Thr Ser Leu Ser Asp Pro Val His
65                  70                  75                  80

Leu Thr Val Leu Ser Glu Trp Leu Val Leu Gln Thr Pro His Leu Glu
                85                  90                  95

Phe Gln Glu Gly Glu Thr Ile Val Leu Arg Cys His Ser Trp Lys Asp
            100                 105                 110

Lys Pro Leu Val Lys Val Thr Phe Phe Gln Asn Gly Lys Ser Gln Lys
        115                 120                 125

Phe Ser His Leu Asp Pro Asn Leu Ser Ile Pro Gln Ala Asn His Ser
    130                 135                 140

His Ser Gly Asp Tyr His Cys Thr Gly Asn Ile Gly Tyr Thr Leu Phe
145                 150                 155                 160

Ser Ser Lys Pro Val Thr Ile Thr Val Gln Ala Pro Ser Val Gly Ser
                165                 170                 175

Ser Ser Pro Val Gly Ile Ile Val Ala Val Val Ile Ala Thr Ala Val
            180                 185                 190

Ala Ala Ile Val Ala Ala Val Val Ala Leu Ile Tyr Cys Arg Lys Lys
        195                 200                 205

Arg Ile Ser Ala Asn Ser Thr Asp Pro Val Lys Ala Ala Gln Phe Glu
    210                 215                 220

Pro Pro Gly Arg Gln Met Ile Ala Ile Arg Lys Arg Gln Leu Glu Glu
225                 230                 235                 240

Thr Asn Asn Asp Tyr Glu Thr Ala Asp Gly Gly Tyr Met Thr Leu Asn
                245                 250                 255

Pro Arg Ala Pro Thr Asp Asp Asp Lys Asn Ile Tyr Leu Thr Leu Pro
            260                 265                 270

Pro Asn Asp His Val Asn Ser Asn Asn
    275                 280

<210> SEQ ID NO 68
<211> LENGTH: 252
<212> TYPE: PRT
<213> ORGANISM: Cynomolgus
<220> FEATURE:
<221> NAME/KEY: MISC_FEATURE
<222> LOCATION: (1)..(252)
<223> OTHER INFORMATION: FcgammaaRIIB

<400> SEQUENCE: 68
```

```
Thr Pro Ala Ala Pro Pro Lys Ala Val Leu Lys Leu Glu Pro Pro Trp
  1               5                  10                  15

Ile Asn Val Leu Arg Glu Asp Ser Val Thr Leu Thr Cys Gly Gly Ala
                 20                  25                  30

His Ser Pro Asp Ser Asp Ser Thr Gln Trp Phe His Asn Gly Asn Leu
             35                  40                  45

Ile Pro Thr His Thr Gln Pro Ser Tyr Arg Phe Lys Ala Asn Asn Asn
     50                  55                  60

Asp Ser Gly Glu Tyr Arg Cys Gln Thr Gly Arg Thr Ser Leu Ser Asp
 65                  70                  75                  80

Pro Val His Leu Thr Val Leu Ser Glu Trp Leu Ala Leu Gln Thr Pro
                 85                  90                  95

His Leu Glu Phe Arg Glu Gly Glu Thr Ile Leu Leu Arg Cys His Ser
                100                 105                 110

Trp Lys Asp Lys Pro Leu Ile Lys Val Thr Phe Phe Gln Asn Gly Ile
            115                 120                 125

Ser Lys Lys Phe Ser His Met Asn Pro Asn Phe Ser Ile Pro Gln Ala
130                 135                 140

Asn His Ser His Ser Gly Asp Tyr His Cys Thr Gly Asn Ile Gly Tyr
145                 150                 155                 160

Thr Pro Tyr Ser Ser Lys Pro Val Thr Ile Thr Val Gln Val Pro Ser
                165                 170                 175

Met Gly Ser Ser Ser Pro Ile Gly Ile Ile Val Ala Val Val Thr Gly
                180                 185                 190

Ile Ala Val Ala Ala Ile Val Ala Ala Val Val Ala Leu Ile Tyr Cys
                195                 200                 205

Arg Lys Lys Arg Ile Ser Ala Asn Pro Thr Asn Pro Asp Glu Ala Asp
    210                 215                 220

Lys Val Gly Ala Glu Asn Thr Ile Thr Tyr Ser Leu Leu Met His Pro
225                 230                 235                 240

Asp Ala Leu Glu Glu Pro Asp Asp Gln Asn Arg Val
                245                 250

<210> SEQ ID NO 69
<211> LENGTH: 234
<212> TYPE: PRT
<213> ORGANISM: Cynomolgus
<220> FEATURE:
<221> NAME/KEY: MISC_FEATURE
<222> LOCATION: (1)..(234)
<223> OTHER INFORMATION: FcgammaRIIIA - Alpha chain

<400> SEQUENCE: 69

Glu Asp Leu Pro Lys Ala Val Val Phe Leu Glu Pro Gln Trp Tyr Arg
  1               5                  10                  15

Val Leu Glu Lys Asp Arg Val Thr Leu Lys Cys Gln Gly Ala Tyr Ser
                 20                  25                  30

Pro Glu Asp Asn Ser Thr Arg Trp Phe His Asn Glu Ser Leu Ile Ser
             35                  40                  45

Ser Gln Thr Ser Ser Tyr Phe Ile Ala Ala Arg Val Asn Asn Ser
     50                  55                  60

Gly Glu Tyr Arg Cys Gln Thr Ser Leu Ser Thr Leu Ser Asp Pro Val
 65                  70                  75                  80

Gln Leu Glu Val His Ile Gly Trp Leu Leu Leu Gln Ala Pro Arg Trp
                 85                  90                  95

Val Phe Lys Glu Glu Glu Ser Ile His Leu Arg Cys His Ser Trp Lys
```

```
                100             105             110
Asn Thr Leu Leu His Lys Val Thr Tyr Leu Gln Asn Gly Lys Gly Arg
            115                 120                 125

Lys Tyr Phe His Gln Asn Ser Asp Phe Tyr Ile Pro Lys Ala Thr Leu
        130                 135                 140

Lys Asp Ser Gly Ser Tyr Phe Cys Arg Gly Leu Ile Gly Ser Lys Asn
145                 150                 155                 160

Val Ser Ser Glu Thr Val Asn Ile Thr Ile Thr Gln Asp Leu Ala Val
                165                 170                 175

Ser Ser Ile Ser Ser Phe Phe Pro Pro Gly Tyr Gln Val Ser Phe Cys
            180                 185                 190

Leu Val Met Val Leu Leu Phe Ala Val Asp Thr Gly Leu Tyr Phe Ser
            195                 200                 205

Met Lys Lys Ser Ile Pro Ser Ser Thr Arg Asp Trp Glu Asp His Lys
            210                 215                 220

Phe Lys Trp Ser Lys Asp Pro Gln Asp Lys
225                 230
```

```
<210> SEQ ID NO 70
<211> LENGTH: 99
<212> TYPE: PRT
<213> ORGANISM: Cynomolgus
<220> FEATURE:
<221> NAME/KEY: MISC_FEATURE
<222> LOCATION: (1)..(99)
<223> OTHER INFORMATION: Beta-2 microglobulin

<400> SEQUENCE: 70
```

```
Ile Gln Arg Thr Pro Lys Ile Gln Val Tyr Ser Arg His Pro Pro Glu
1               5                   10                  15

Asn Gly Lys Pro Asn Phe Leu Asn Cys Tyr Val Ser Gly Phe His Pro
            20                  25                  30

Ser Asp Ile Glu Val Asp Leu Leu Lys Asn Gly Glu Lys Met Gly Lys
            35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Asn Glu Lys Asp Glu Tyr Ala Cys
65                  70                  75                  80

Arg Val Asn His Val Thr Leu Ser Gly Pro Arg Thr Val Lys Trp Asp
                85                  90                  95

Arg Asp Met
```

```
<210> SEQ ID NO 71
<211> LENGTH: 342
<212> TYPE: PRT
<213> ORGANISM: Cynomolgus
<220> FEATURE:
<221> NAME/KEY: MISC_FEATURE
<222> LOCATION: (1)..(342)
<223> OTHER INFORMATION: FcgammaRn alpha-chain (S3)

<400> SEQUENCE: 71
```

```
Ala Glu Ser His Leu Ser Leu Leu Tyr His Leu Thr Ala Val Ser Ser
1               5                   10                  15

Pro Ala Pro Gly Thr Pro Ala Phe Trp Val Ser Gly Trp Leu Gly Pro
            20                  25                  30

Gln Gln Tyr Leu Ser Tyr Asp Ser Leu Arg Gly Gln Ala Glu Pro Cys
            35                  40                  45
```

-continued

```
Gly Ala Trp Val Trp Glu Asn Gln Val Ser Trp Tyr Trp Glu Lys Glu
    50                  55                  60

Thr Thr Asp Leu Arg Ile Lys Glu Lys Leu Phe Leu Glu Ala Phe Lys
65                  70                  75                  80

Ala Leu Gly Gly Lys Gly Pro Tyr Thr Leu Gln Gly Leu Leu Gly Cys
                85                  90                  95

Glu Leu Ser Pro Asp Asn Thr Ser Val Pro Thr Ala Lys Phe Ala Leu
            100                 105                 110

Asn Gly Glu Glu Phe Met Asn Phe Asp Leu Lys Gln Gly Thr Trp Gly
        115                 120                 125

Gly Asp Trp Pro Glu Ala Leu Ala Ile Ser Gln Arg Trp Gln Gln Gln
    130                 135                 140

Asp Lys Ala Ala Asn Lys Glu Leu Thr Phe Leu Leu Phe Ser Cys Pro
145                 150                 155                 160

His Arg Leu Arg Glu His Leu Glu Arg Gly Arg Gly Asn Leu Glu Trp
                165                 170                 175

Lys Glu Pro Pro Ser Met Arg Leu Lys Ala Arg Pro Gly Asn Pro Gly
            180                 185                 190

Phe Ser Val Leu Thr Cys Ser Ala Phe Ser Phe Tyr Pro Pro Glu Leu
        195                 200                 205

Gln Leu Arg Phe Leu Arg Asn Gly Met Ala Ala Gly Thr Gly Gln Gly
    210                 215                 220

Asp Phe Gly Pro Asn Ser Asp Gly Ser Phe His Ala Ser Ser Ser Leu
225                 230                 235                 240

Thr Val Lys Ser Gly Asp Glu His His Tyr Cys Cys Ile Val Gln His
                245                 250                 255

Ala Gly Leu Ala Gln Pro Leu Arg Val Glu Leu Glu Thr Pro Ala Lys
            260                 265                 270

Ser Ser Val Leu Val Val Gly Ile Val Ile Gly Val Leu Leu Leu Thr
        275                 280                 285

Ala Ala Ala Val Gly Gly Ala Leu Leu Trp Arg Arg Met Arg Ser Gly
    290                 295                 300

Leu Pro Ala Pro Trp Ile Ser Leu Arg Gly Asp Asp Thr Gly Ser Leu
305                 310                 315                 320

Leu Pro Thr Pro Gly Glu Ala Gln Asp Ala Asp Ser Lys Asp Ile Asn
                325                 330                 335

Val Ile Pro Ala Thr Ala
            340

<210> SEQ ID NO 72
<211> LENGTH: 342
<212> TYPE: PRT
<213> ORGANISM: Cynomolgus
<220> FEATURE:
<221> NAME/KEY: MISC_FEATURE
<222> LOCATION: (1)..(342)
<223> OTHER INFORMATION: FcgammaRn alpha-chain (N3)

<400> SEQUENCE: 72

Ala Glu Asn His Leu Ser Leu Leu Tyr His Leu Thr Ala Val Ser Ser
1               5                   10                  15

Pro Ala Pro Gly Thr Pro Ala Phe Trp Val Ser Gly Trp Leu Gly Pro
            20                  25                  30

Gln Gln Tyr Leu Ser Tyr Asp Ser Leu Arg Gly Gln Ala Glu Pro Cys
        35                  40                  45

Gly Ala Trp Val Trp Glu Asn Gln Val Ser Trp Tyr Trp Glu Lys Glu
```

-continued

```
              50                      55                      60
Thr Thr Asp Leu Arg Ile Lys Glu Lys Leu Phe Leu Glu Ala Phe Lys
65                   70                  75                  80

Ala Leu Gly Gly Lys Gly Pro Tyr Thr Leu Gln Gly Leu Leu Gly Cys
                85                  90                  95

Glu Leu Ser Pro Asp Asn Thr Ser Val Pro Thr Ala Lys Phe Ala Leu
               100                 105                 110

Asn Gly Glu Glu Phe Met Asn Phe Asp Leu Lys Gln Gly Thr Trp Gly
           115                 120                 125

Gly Asp Trp Pro Glu Ala Leu Ala Ile Ser Gln Arg Trp Gln Gln Gln
        130                 135                 140

Asp Lys Ala Ala Asn Lys Glu Leu Thr Phe Leu Leu Phe Ser Cys Pro
145                 150                 155                 160

His Arg Leu Arg Glu His Leu Glu Arg Gly Arg Gly Asn Leu Glu Trp
               165                 170                 175

Lys Glu Pro Pro Ser Met Arg Leu Lys Ala Arg Pro Gly Asn Pro Gly
           180                 185                 190

Phe Ser Val Leu Thr Cys Ser Ala Phe Ser Phe Tyr Pro Pro Glu Leu
           195                 200                 205

Gln Leu Arg Phe Leu Arg Asn Gly Met Ala Ala Gly Thr Gly Gln Gly
       210                 215                 220

Asp Phe Gly Pro Asn Ser Asp Gly Ser Phe His Ala Ser Ser Ser Leu
225                 230                 235                 240

Thr Val Lys Ser Gly Asp Glu His His Tyr Cys Cys Ile Val Gln His
               245                 250                 255

Ala Gly Leu Ala Gln Pro Leu Arg Val Glu Leu Glu Thr Pro Ala Lys
           260                 265                 270

Ser Ser Val Leu Val Val Gly Ile Val Ile Gly Val Leu Leu Leu Thr
           275                 280                 285

Ala Ala Ala Val Gly Gly Ala Leu Leu Trp Arg Arg Met Arg Ser Gly
       290                 295                 300

Leu Pro Ala Pro Trp Ile Ser Leu Arg Gly Asp Asp Thr Gly Ser Leu
305                 310                 315                 320

Leu Pro Thr Pro Gly Glu Ala Gln Asp Ala Asp Ser Lys Asp Ile Asn
               325                 330                 335

Val Ile Pro Ala Thr Ala
               340
```